US008222378B2

(12) United States Patent
Masure

(10) Patent No.: US 8,222,378 B2
(45) Date of Patent: *Jul. 17, 2012

(54) NEUROTROPHIC GROWTH FACTOR, ENOVIN

(75) Inventor: Stefan Leo Jozef Masure, Brasschaat (BE)

(73) Assignee: Janssen Pharmaceutica N.V. (BE)

( * ) Notice: Subject to any disclaimer, the term of this patent is extended or adjusted under 35 U.S.C. 154(b) by 900 days.

This patent is subject to a terminal disclaimer.

(21) Appl. No.: 11/381,871

(22) Filed: May 5, 2006

(65) Prior Publication Data

US 2008/0206277 A1 Aug. 28, 2008

Related U.S. Application Data

(63) Continuation of application No. 09/357,349, filed on Jul. 14, 1999, now Pat. No. 7,067,473, which is a continuation-in-part of application No. 09/327,668, filed on Jun. 8, 1999, now abandoned, and a continuation-in-part of application No. 09/248,772, filed on Feb. 12, 1999, now abandoned.

(30) Foreign Application Priority Data

Jul. 14, 1998 (GB) .................................. 9815283.8

(51) Int. Cl.
*C07K 14/475* (2006.01)
(52) U.S. Cl. ........................................................ 530/399
(58) Field of Classification Search ........................ None
See application file for complete search history.

(56) References Cited

U.S. PATENT DOCUMENTS

| | | | |
|---|---|---|---|
| 5,194,596 | A | 3/1993 | Tischer et al. |
| 5,350,836 | A | 9/1994 | Kopchick et al. |
| 5,739,307 | A | 4/1998 | Johnson et al. |
| 5,747,655 | A | 5/1998 | Johnson et al. |
| 6,284,540 | B1 | 9/2001 | Milbrandt et al. |
| 6,593,133 | B1 | 7/2003 | Johansen et al. |
| 6,734,284 | B1 | 5/2004 | Johansen et al. |
| 7,067,473 | B1 | 6/2006 | Masure |
| 2004/0043927 | A1 | 3/2004 | Baker et al. |
| 2004/0142418 | A1 | 7/2004 | Sah et al. |
| 2005/0233359 | A1 | 10/2005 | Masure |
| 2006/0122135 | A1 | 6/2006 | Geerts et al. |

FOREIGN PATENT DOCUMENTS

| | | |
|---|---|---|
| DK | 1998 00904 | 7/1998 |
| WO | WO 97/19693 | 6/1997 |
| WO | WO 99/49039 | 9/1999 |
| WO | WO 00/01815 | 1/2000 |
| WO | WO-00/04050 A2 | 1/2000 |
| WO | WO-00/17360 A1 | 3/2000 |
| WO | WO-00/18799 A1 | 4/2000 |
| WO | WO-00/34475 A2 | 6/2000 |

OTHER PUBLICATIONS

Rudinger, In "Peptide Hormones" (ed. J.A. Parsons) University Park Press, Baltimore, pp. 1-7 (1976).*
Skolnick, et al. (2000) Trends in Bioscience 18(1): 34-39.
Altschul, et. al., "Basic Local Alignment Search Tool," Journal of Molecular Biology 215: 403-410 (1990).
Angrist, et al. (Nov. 1996) "Germline mutations in glial cell line-derived neurotrophic factor (GDNF) and RET in a Hirschsprung disease patient," Nature Genetics 14: 341-344.
Barr (Jul. 12, 1991) Mammalian subtilisins: The long-sought dibasic processing endoproteases, Cell 66: 1-3.
Beck, et al. (Jan. 26, 1995) "Mesencephalic dopaminergic neurons protected by GDNF from axotomy-induced degeneration in the adult brain," Nature 373: 339-341.
Bilang-Bleuel, et. al. (Aug. 1997) "Intrastriatal injection of an adenoviral vector expressing glial-cell-line-derived neurotrophic factor prevents dopaminergic neuron degeneration and behavioral impairment in a rat model of Parkinson disease," Proc. Natl. Acad. Sci. 94: 8818-8823.
Buj-Bello, A. et. al., "Neurturin responsiveness requires a GPI-linked receptor and the Ret receptor tyrosine kinase," Nature 387: 721-724 (1997).
Buj-Bello, A. et. al., "GDNF is an Age-Specific Survival Factor for Sensory and Autonomic Neurons," Neuron 15: 821-828 (1995).
Burgess, et al. (Nov. 1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue." Journal of Cell Biology 111: 2129-2138.
Campbell and Meyer (Oct. 5, 2006) "Mechanisms of Neuropathic Pain." Neuron 52(1): 77-92.
Choi-Lundberg, et. al. (1997) "Dopaminergic Neurons Protected from Degeneration by GDNF Gene Therapy," Science 275: 838-841.
Creedon, D.J. et. al. (1997) "Neurturin shares receptors and signal transduction pathways with glial cell line-derived neurotrophic factor in sympathetic neurons," Proc. Natl. Acad. Sci. 94: 7018-7023.
Davies, A.M. et. al., "Nomenclature of GPI-Linked Receptors for the GDNF Ligand Family," Neuron vol. 19, 485 (1997).
Durbec, et al. (Jun. 27, 1996) "GDNF signaling through the Ret receptor tyrosine kinase," Nature 381: 789-793.
Edery, P. et. al., (Jan. 27, 1994) "Mutations of the RET proto-oncogene in Hirschsprung's disease," Nature 367: 378-380.
Gash, D.M., "Functional recovery in parkinsonian monkeys treated with GDNF," Nature 380: 252-255 (1996).
Gustafsson (Sep. 2000) "New insights in oestrogen receptor (EF) research—the ERβ." Eur. J. Cancer 36(Suppl. 4): S16.
Hakim, MD, A., "Ischemic penumbra, The therapeutic window," Neurology 51, Supplement 3, S44-S46 (1998).
Henderson, et al., (1994) "GDNF: a potent survival factor for motoneurons present in peripheral nerve and muscle," Science 266: 1062-1064.
Heng, H.H.Q & Tsu, L-C, "Modes of DAPI banding and simultaneous in situ," Chromosoma 102: 325-332, (1993).
Heuckeroth, R. et. al., Neurturin, a Novel Neurotrophic Factor, is Localized to Mouse Chromosome 17 and Human Chromosome 19p. 13.3, Genomics 44: 137-140 (1997).

(Continued)

*Primary Examiner* — Robert C Hayes
(74) *Attorney, Agent, or Firm* — Patton Boggs LLP

(57) ABSTRACT

There is disclosed an isolated nucleic acid molecule encoding a human neurotrophic growth factor designated enovin and having the amino acid sequence illustrated in FIG. 1, 21, 23 or 24 or encoding a functional equivalent, derivative or biprecursor of said growth factor. The growth factor preferably comprises the amino acid sequence from position 27 to 139 of the sequence illustrated in FIG. 1, or a functional equivalent, derivative or bioprecursor thereof. The nucleic acid molecule encoding enovin can be used to transform a host cell, tissue or organism by including it in an appropriate vector. The host cell, tissue or organism and the vector also form part of the invention.

5 Claims, 28 Drawing Sheets

OTHER PUBLICATIONS

Jing S. et al., "GDNF-induced Activation of the Ret Protein Tyrosine Kinase is Mediated by GDNFR-α, a Novel Receptor for GDNF," Cell 85: 1113-1124 (1996).

Jing, S. et. al., "GFRα-2 and GFRα-3 Are Two New Receptors for Ligands of the GDNF Family," The Journal of Biological Chemistry vol. 272, No. 52, Issue of Dec. 26, 33111-33117, (1997).

Kellow and Bennett (Oct. 1996) "Functional Disorders of the Small Intestine." Semin. Gastrointest. Dis. 7(4): 208-216.

Kingsley, D., "The TGF-β superfamily: new members, new receptors, and new genetic tests of function in different organisms," Cold Spring Harbor Laboratory Press, Genes & Development 8: 133-146, (1994).

Klein, R. et al. (1997) "A GPI-linked protein that interacts with Ret to form a candidate neurturin receptor," Nature vol. 387: 717-721 (1997) and correction in Nature vol. 392: 210.

Kotzbauer, et al. "Neurturin, a relative of glial-cell-line-derived neurotrophic factor," Nature 384, 467-470 (1996).

Lin, et al. (1993) "GDNF: A Glial Cell Line-Derived Neurotrophic Factor for Midbrain Dopaminergic Neurons." Science 260: 1130-1132.

Mandel, R.J. et. al., "Midbrain injection of recombinant adeno-associated virus encoding rat glial cell line-derived neurotrophic factor protects nigral neurons in a progressive 6-hydroxydopamine-induced degeneration model of Parkinson's disease in rats," Proc. Natl. Acad. Sci. 94: 14083-14088 (1997).

Martucciello, et al. (Jan. 1998) "GNDF Deficit in Hirschsprung's Disease." Journal of Pediatatric Surgery 33(1): 99-102.

Masure, et.al, "Molecular cloning, expression and tissue distribution of glial-cell-line-derived neurotrophic factor family receptor," Eur. J. Biochem 251: 622-630 (1998).

Matsushita, N. et. al., "Cloning and structural organization of the gene encoding the mouse glial cell line-derived neurotrophic factor, GDNF," Gene 203: 149-157 (1997).

Milbrandt, J. et. al. (1998) "Persephin, a Novel Neurotrophic Factor Related to GDNF and Neurturin," Neuron vol. 20: 245-253.

Mita, S. et. al. (1989) "Detection of "Deleted" Mitochondrial Genomes in Cytochrome-c Oxidase-Deficient Muscle Fibers of a Patient with Kearns-Sayre Syndrome," Proc. Natl. Acad. Sci. 86: 9509-9513.

Mogyoros, et al. (1998) "Strength-duration properties of sensory and motor axons in amyotrophic lateral sclerosis." Brain 121: 851-859.

Moore, et al. (Jul. 4, 1996) "Renal and neuronal abnormalities in mice lacking GDNF," Nature 382: 76-79.

Mount, H.T.J. et. al., "Glial Cell Line-Derived Neurotrophic Factor Promotes the Survival and Morphologic Differentiation of Purkinje Cells," Proc. Natl. Acad. Sci. 92: 9092-9096 (1995).

Nagy, Z.S. et. al., "The Cell Division Cycle and the Pathophysiology of Alzheimer's Disease," NeuroScience Vo. 87, No. 4, pp. 731-739 (1998).

Naveilhan, et. al., "Expression and regulation of GFRalpha 3, a glial cell line-derived neurotrophic factor family receptor," Proc. Natl. Acad. Sci. 95: 1295-1300 (1998).

Nuydens, R. et. al., "Bcl-2 protects neuronal cells against taxol-induced apoptosis by inducing multi-nucleation," Apoptosis 5: 335-343 (2000).

Oppenheim, et al. (Jan. 26, 1995) "Developing motor neurons rescued from programmed and axotomy-induced cell death by GDNF," Nature 373: 344-346.

Pawson and Nash (Apr. 18, 2003) "Assembly of Cell Regulatory Systems Through Protein Interaction Domains." Science 300: 445-452.

Pichel, J.G. et. al., "Defects in enteric innervation and kidney development in mice lacking GDNF," Nature vol. 382: 73-76 (1996).

Pons, et al. (Jun. 28, 1991) "Massive Cortical Reorganization after Sensory Deafferentation in Adult Macaques." Science 252: 1857-1860.

Ramachandran, et al. (Nov. 1992) "Perceptual Correlates of Massive Cortical Reorganization." Science 258: 1159-1160.

Ramachandran (Nov. 1993) "Behavioral and magnetoencephalographic correlates of plasticity in the adult human brain." Proc. Natl. Acad. Sci. USA 90: 10413-10420.

Rico, et al. (Jan. 1998) "Characterization of the Immunostimulatory Properties of Leishmania infantum HSP70 by Fusion to the Escherichia coli Maltose-Binding Protein in Normal and nu/nu BALB/c Mice." Infection and Immunity 66(1): 347-352.

Romeo, et al. "Point mutations affecting the tyrosine kinase domain of the RET proto-oncogene in Hirschsprung's disease," Nature 367: 377-378 (1994).

Saarma and Sariola "Other Neurotrophic Factors: Glial Cell Line-Derived Neurotrophic Factor (GDNF)." Microscopy Research and Techniques 45 (1999): 292-302.

Sanchez, et al. (Jul. 4, 1996) "Renal agenesis and the absence of enteric neurons in mice lacking GDNF," Nature 382: 70-73.

Sanicola, et. al. (1997) "Glial cell line-derived neurotrophic factor-dependent RET activation can be mediated by two different cell-surface accessory proteins," Proc. Natl. Acad. Sci. 94: 6238-6243.

Sherman, et al. (1984) "Chronic Phantom and Stump Pain among American Veterans: Results on a Survey." Pain 18: 83-95.

Smirnova, et. al., "Thrombin Is an Extracellular Signal that Activates Intracellular Death Protease Pathways inducing Apoptosis in Model Motor Neurons," Thrombin and Neuronal Apoptosis: 64-80 (1998).

Srinivasan, et. al., "Serum from Patients with Type 2 Diabetes with Neuropathy Induces Complement-independent, Calcium-dependent Apoptosis in Cultured Neuronal Cells," The American Society for Clinical Investigation, Inc., vol. 102, No. 7: 1454-1462, (1998).

Steger, C., "An unbiased detector of curviliniear structures," IEEE Transactions on pattern analysis and machine 20: 113-125 (1998).

Suvanto, et. al., "Cloning, mRNA distribution and chromosomal localisation of the gene for glial cell line-derived neurotrophic factor receptor β, a homologue to GDNFR-α," Human Molecular Genetics vol. 6, No. 8: 1267-1273, (1997).

Tomac, et al. "Protection and repair of the nigrostriatal dopaminergic system by GDNF in vivo," Nature 373: 335-339 (1995).

Treanor, et al. (Jul. 4, 1996) "Characterization of a multicomponent receptor for GDNF," Nature 382: 80-83.

Trupp, et al. (Jul. 1995) "Peripheral Expression and Biological Activities of GDNF, a New Neurotrophic Factor for Avian and Mammalian Peripheral Neurons." The Journal of Cell Biology 130(1): 137-148.

Trupp (1996) "Functional receptor for GDNF encoded by the c-ret proto-oncogene," Nature 381: 785-788.

Wang and Wang (2003) "Animal and Cellular Modles of Chronic Pain." Advanced Drug Delivery Reviews (2003) 55:949-965.

White, et al. (Oct. 2005) Chemokines: Integrators of Pain and Inflammation Nat Rev. Drug Discovery 4: 834-844.

Widenfalk, et. al., "Neurturin and Glial Cell Line-Derived Neurotrophic Factor Receptor-β (GDNFR-β), Novel Proteins Related to GDNF and GDNFR-α with Specific Cellular Patterns of Expression Suggesting Roles in the Developing and Adult Nervous System and in Peripheral Organs," The Journal of NeuroScience vol. 17(21): 8506-8519 (1997).

Widenfalk, et. al., GFRα3, a protein related to GFRα-1, is expressed in developing peripheral neurons and ensheathing cells, European Journal of Neuroscience , vol. 10.: 1508-1517, (1998).

Wellington, et al. (1997) "Toward understanding the Molecular Pathology of Huntington's Disease," Brain Pathology 7(3):979-1002.

Worby et. al., "Glial Cell Line-derived Neurotrophic Factor Signals through the RET Receptor and Activates Mitogen-activated Protein Kinsase," The Journal of Biological Chemistry vol. 271(39): 23619-23622, (1996).

Worby, et. al. (1998) "Identification and Characterization of GFRα-3, a Novel Co-receptor Belonging to the Glial Cell Line-derived Neurotrophic Receptor of Family," The Journal of Biological Chemistry 273(6): 3502-3508.

Yan (1995) "In vivo neurotrophic effects of GDNF on neonatal and adult facial motor neurons," Nature 373: 341-344.

Notice of Opposition to European Patent (including grounds) filed by Biogen on Jul. 23, 2007 in the European Patent Office, EP1097167.

Notice of Opposition to European Patent (including grounds) filed by NsGene A/S on Jul. 24, 2007 in the European Patent Office, EP1097167.

Patentee's Observations on the Opposition filed by Janssen Pharmaceutica NV on May 21, 2008 in the European Patent Office, EP1097167.

In the U.S. Patent and Trademark Office, Notice of Allowance in re: U.S. Appl. No. 09/357,349, dated Feb. 23, 2006, 3 pages.

In the U.S. Patent and Trademark Office, Notice of Allowance in re: U.S. Appl. No. 09/357,349, dated Feb. 7, 2006, 7 pages.

In the U.S. Patent and Trademark Office, Final Office Action in re: U.S. Appl. No. 09/357,349, dated May 20, 2005, 14 pages.

In the U.S. Patent and Trademark Office, Office Action in re: U.S. Appl. No. 09/357,349, dated May 17, 2004, 8 pages.

In the U.S. Patent and Trademark Office, Final Office Action in re: U.S. Appl. No. 09/357,349, dated Mar. 26, 2003, 5 pages.

In the U.S. Patent and Trademark Office, Office Action in re: U.S. Appl. No. 09/357,349, dated Oct. 4, 2001, 11 pages.

In the U.S. Patent and Trademark Office, Restriction/Election Requirement in re: U.S. Appl. No. 09/357,349, dated Jun. 19, 2001, 4 pages.

In the U.S. Patent and Trademark Office, Restriction/Election Requirement in re: U.S. Appl. No. 09/357,349, dated Oct. 2, 2000, 10 pages.

In the U.S. Patent and Trademark Office, Office Action in re: U.S. Appl. No. 12/974,625, dated Nov. 21, 2011, 10 pages.

Baloh et al. "GFRα3 is an orphan member of the GDNF/neurturin/persephin receptor family," *Proc. Natl. Acad. Sci. USA*, May 1998: 95, pp. 5801-5806.

Baloh et al., "TrnR2, a Novel Receptor That Mediates Neurturin and GDNF Signaling through Ret," *Neuron*, May 1997: 18, pp. 793-802.

Baloh et al., *Neuron*, 1998: 21, pp. 1291-1302.

Choh, *PNAS*, 1990: 77(6), pp. 3122-3214.

GenBank Accession No. AC005038, "Homo sapiens BAC clone RP11-486I22 from 1, complete sequence," May 9, 2001.

GFRα Nomenclature Committe, "Nomenclature of GPI-Linked Receptors for the GDNF Ligand Family," *Neuron*, Sep. 1997: 19, pp. 485.

Heng et al., "High resolution mapping of mammalian genes by in situ hybridization to free chromatin," *Proc. Natl. Acad. Sci. USA*, Oct. 1992: 89, pp. 9509-9513.

Jobling et al., "Analysis of structure and function of the B subunit of cholera toxin by the use of site—directed mutagenesis," *Mol. Micro.*, 1991: 5(7), pp. 1755-67 (Abstract).

Marsden et al., "The Causes of Parkinson's Disease Are Being Unraveled and Rational Neuroprotective Therapy Is Close to Reality," *Annals of Neurology; American Neurological Association*, 1998: 44(3, 1), pp. S189-196.

Masure et al., "Enovin, a member of the glial cell-line-derived neurotrophic factor (GDNF) family with growth promoting activity on neuronal cells. Existence and tissue-specific expression of different splice variants,." *Eur. J. Biochem.*, 1999: 266(3), pp. 892-902.

Naveilhan et al., "Expression and regulation of GFRα3, a glial cell line-derived neurotrophic factor family receptor," *Proc. Natl. Acad. Sci. USA*, Feb. 1998: 95, pp. 1295-1300.

Vukicevic et al., "Induction of nephrogenic mesenchyme by osteogenic protein 1 (bone morphogenetic protein 7)," *PNAS USA*, 1996: 93, pp. 9021-9026.

* cited by examiner

```
        P   P   Q   P   S   R   P   A   P   P   P   P   A   P   P   S      16
       cgccgccgcagccttctcggcccgcgccccgccgcctgcaccccatct                     50

A   L   P   R   G   G   R   A   A   R   A   G   G   P   G   S   R   33
       gctcttccccgcggggccgcgcggcgcgggctgggggcccgggcagccg                    100

A   R   A   A   G   A   R   G   C   R   L   R   S   Q   L   V     49
       cgctcgggcagcggggccgcggggctgccgcctgcgctcgcagctggtgc                   150

P   V   R   A   L   G   L   G   H   R   S   D   E   L   V   R   P   66
       cggtgcgcgcgctcggcctgggccaccgctccgacgagctggtgcgtttc                   200

R   F   C   S   G   S   C   R   R   A   R   S   P   H   D   L   S 83
       cgcttctgcagcggctcctgccgccgcgcgcgctctccacacgacctcag                   250

L   A   S   L   L   G   A   G   A   L   R   P   P   P   G   S     99
       cctggccagcctactgggcgccggggccctgcgaccgccccgggctccc                    300

R   P   V   S   Q   P   C   C   R   P   T   R   Y   E   A   V   S   116
       ggcccgtcagccagccctgctgccgacccacgcgctacgaagcggtctcc                   350

P   M   D   V   N   S   T   W   R   T   V   D   R   L   S   A   T 133
       ttcatggacgtcaacagcacctggagaaccgtggaccgcctctccgccac                   400

A   C   G   C   L   G   * SEQ ID NO: 4                             139
       cgcctgcggctgcctgggctgagggctcgctccagggctttgcagactgg                   450 accccttaccggtggccttcctgc  SEQ ID NO: 2                                474
```

FIG. 1

```
              SEQ ID NO: 16                    *                                   *
hGDNF :  SPDKQMAVLPRRERNRQAAAANPENSRGKGRRGQRGKNRGQVITAIHLNVTDLGLGHETKEELIFRYCSG   : 70
                                              SEQ ID NO: 19
hNTN  :  ---------------------------------ARLGARPCGLRELEVRVSELGLGYASDETVLFRYCAG   : 37
                                              SEQ ID NO: 22
hPSP  :  -----------------------------------ALSGPCQLWSLTLSVAELGLGYASEEKVIFRYCAG   : 35
                                 SEQ ID NO: 25
hEVN  :  -------------------------AGGPGSRARAAGARGCRLRSQLVPVRALGLGHRSDELVRFRFCSG   : 45

*       SEQ ID NO: 17            **    SEQ ID NO: 18          * *
hGDNF :  SCDA-SETTYDKILKNLSRNRRLVS----DKVGQACCRPIAFDDDLSFLDDNLVYHILRKHSAKRCGCI-   :134
                   SEQ ID NO: 20                    SEQ ID NO: 21
hNTN  :  AGEA-AARVYDLGLRRLRQRRRLRR---ESVRAQPCCRPTAYEDEVSFLDAHSRYHTVHELSAREQAGV-   :102
                                              SEQ ID NO: 23          SEQ ID NO: 24
hPSP  :  SCPRG-ERTQHGLALARLQGQG--------BAHGGPCCRPTRF-TDAELLDRHRWQRLPQLSAAACGCGG  : 96
                  SEQ ID NO: 26                              SEQ ID NO: 27
hEVN  :  SCRR-SRSPHDLSLASLLGAGALRPPPGSEPVSQPCCRPTRE-AVSFMDVNSTWRTVDRLSATACGCLG   :113
```

| | 1 | 2 | 3 | 4 | 5 | 6 | 7 | 8 |
|---|---|---|---|---|---|---|---|---|
| A | whole brain | amygdala | caudate nucleus | cere-bellum | cerebral cortex | frontal lobe | hippo-campus | medulla oblongata |
| B | occipital lobe | putamen | substantia nigra | temporal lobe | thalamus | sub-thalamic nucleus | spinal cord | |
| C | heart | aorta | skeletal muscle | colon | bladder | uterus | prostate | stomach |
| D | testis | ovary | pancreas | pituitary gland | adrenal gland | thyroid gland | salivary gland | mammary gland |
| E | kidney | liver | small intestine | spleen | thymus | peripheral leukocyte | lymph node | bone marrow |
| F | appendix | lung | trachea | placenta | | | | |
| G | fetal brain | fetal heart | fetal kidney | fetal liver | fetal spleen | fetal thymus | fetal lung | |
| H | yeast total RNA 100 ng | yeast tRNA 100 ng | E. coli rRNA 100 ng | E. coli DNA 100 ng | Poly r(A) 100 ng | human C₀t 1 DNA 100 ng | human DNA 100 ng | human DNA 500 ng |

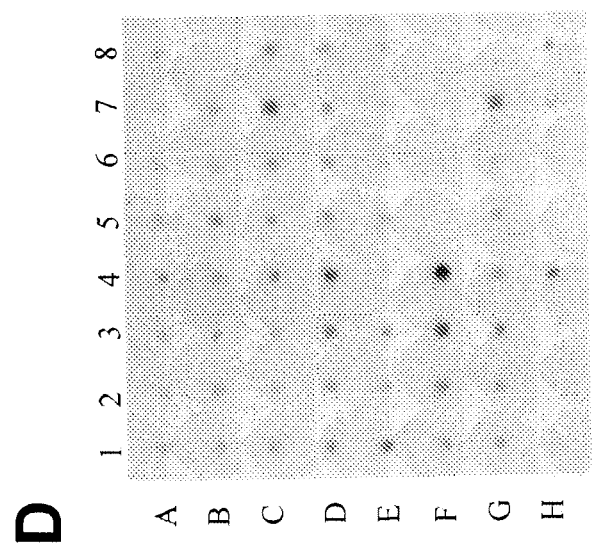

```
                                          M  E  L  G  L  G  G  L  S  T  L   11
   1 CTGATGGGCGCTCCTGGTGTTGATAGAGATGGAACTTGGACTTGGAGGCCTCTCCACGCT
                                    (5'-1)
     S  H  C  P  W  P  R  R  Q      SEQ ID NO: 28                           20
  61 GTCCCACTGCCCCTGGCCTAGGCGGCAGGTGAGTGGTTCTCCCAGTGACTCCTACCTGGT

121 ACTGAGGAAAGGCGGCTTGACTGGTGAGGAGAGCAGGGCTTGGCTTGGGCAGCGGTTAG

181 GTGTGGGAGGGAAAATGGTCAGGGAGGGACCAGGTGAATGGGAGGAGGAGCGGGACTTCT

241 CTGAATGGTCGGTGCACTCAGGTGATTCCTCCCCTGGGCTCCCAGAGGCAGCAAACCCAT

301 TATACTGGAACCTAGGCCCTTCCTGAGTTTCCCCTCCACACAGCTAGGAGCCCATGCCCG

361 GCCTGATCTCAGCCCGAGGACAGCCCCTCCTTGAGGTCCTTCCTCCCCAAGCCCACCTGG
                       (3'-1)                    (3'-2)
                              A  P  L  G  L  S  A  Q  P  A  L  W  P         33
 421 GTGCCCTCTTTCTCCCTGAGGCTCCACTTGGTCTCTCCGCGCAGCCTGCCCTGTGGCCCA

T  L  A  A  L  A  L  L  S  S  V  A  E  A  S  L  G  S  A  P            53
 481 CCCTGGCCGCTCTGGCTCTGCTGAGCAGCGTCGCAGAGGCCTCCCTGGGCTCCGGGCCCC

R  S  P  A  P  R  E  G  P  P  P  V  L  A  S  P  A  G  H  L            73
 541 GCAGCCCTGCCCCCCGCGAAGGCCCCCCGCCTGTCCTGGCGTCCCCCGCCGGCCACCTGC
            (5'-2)
     P  |  SEQ ID NO: 29                                                    74
 601 CGGGTAGGTGAGAGGGCGAGGGGGCGGGGCGGGGCTGGCCCGGGACACCGCGCGTGACTG
            (3'-3)
             G  R  T  A  R  W  C  S  G  R  A  R  R  P  P                   90
 661 GGTCTCATTCCAGGGGGACGCACGGCCCGCTGGTGCAGTGGAAGAGCCCGGCGGCCGCCG

P  Q  P  S  R  P  A  P  P  P  P  A  P  P  S  A  L  P  R  G           110
 721 CCGCAGCCTTCTCGGCCCGCGCCCCCGCCGCCTGCACCCCCATCTGCTCTTCCCCGCGGG
                                        → mature enovin
     G  R  A  A  R | A  G  G  P  G  S  R  A  R  A  A  G  A  R  G          130
 781 GGCCGCGCGGCGCGGGCTGGGGGCCCGGGCAGCCGCGCTCGGGCAGCGGGGGCGCGGGGC C  R  L  R  S  Q  L  V  P  V  R  A  L  G  L  H  R  S  D             150
 841 TGCCGCCTGCGCTCGCAGCTGGTGCCGGTGCGCGCGCTCGGCCTGGGCCACCGCTCCGAC
                                 (3'-4)
     E  L  V  R  F  R  F  C  S  G  S  C  R  R  A  R  S  P  H  D           170
 901 GAGCTGGTGCGTTTCCGCTTCTGCAGCGGCTCCTGCCGCCGCGCGCGCTCTCCACACGAC L  S  L  A  S  L  L  G  A  G  A  L  R  P  P  P  G  S  R  P           190
 961 CTCAGCCTGGCCAGCCTACTGGGCGCCGGGGCCCTGCGACCGCCCCCGGGCTCCCGGCCC V  S  Q  P  C  C  R  P  T  R  Y  E  A  V  S  F  M  D  V  N           210
1021 GTCAGCCAGCCCTGCTGCCGACCCACGCGCTACGAAGCGGTCTCCTTCATGGACGTCAAC
                                                          SEQ ID NO: 30
     S  T  W  R  T  V  D  R  L  S  A  T  A  C  G  C  L  G  *             228
1081 AGCACCTGGAGAACCGTGGACCGCCTCTCCGCCACCGCCTGCGGCTGCCTGGGCTGAGGG

1141 CTCGCTCCAGGGCTTTGCAGACTGGACCCTTACCGGTGGCTCTTCCTG SEQ ID NO: 8
```

FIG. 21

```
  1  MELGLGGLST LSHCPWPRRQ APLGLSAQPA LWPTLAALAL LSSVAEASLG

51  SAPRSPAPRE GPPPVLASPA GHLPGGRTAR WCSGRARRPP PQPSRPAPPP

101  PAPPSALPRG GRAARAGGPG SRARAAGARG CRLRSQLVPV RALGLGHRSD

151  ELVRFRFCSG.SCRRARSPHD LSLASLLGAG ALRPPPGSRP VSQPCCRPTR

201  YEAVSFMDVN STWRTVDRLS ATACGCLG  SEQ ID NO: 9
```

FIG. 23

```
  1  MELGLGGLST  LSHCPWPRRQ  PALWPTLAAL  ALLSSVAEAS  LGSAPRSPAP

51  REGPPPVLAS  PAGHLPGGRT  ARWCSGRARR  PPPQPSRPAP  PPPAPPSALP

101  RGGRAARAGG  PGSRARAAGA  RGCRLRSQLV  PVRALGLGHR  SDELVRFRFC

151  SGSCRRARSP  HDLSLASLLG  AGALRPPPGS  RPVSQPCCRP  TRYEAVSFMD

201  VNSTWRTVDR  LSATACGCLG  SEQ ID NO: 10
```

FIG. 24

SEQUENCE LISTING

```
<160> NUMBER OF SEQ ID NOS: 49

<210> SEQ ID NO 1
<211> LENGTH: 339
<212> TYPE: DNA
<213> ORGANISM: Homo sapiens

<400> SEQUENCE: 1
gctgggggcc cgggcagccg cgctcgggca gcggggggcgc ggggctgccg cctgcgctcg      60
cagctggtgc cggtgcgcgc gctcggcctg ggccaccgct ccgacgagct ggtgcgtttc     120
cgcttctgca gcggctcctg ccgccgcgcg cgctctccac acgacctcag cctggccagc     180
ctactgggcg ccggggccct gcgaccgccc ccgggctccc ggcccgtcag ccagccctgc     240
tgccgaccca cgcgctacga agcggtctcc ttcatggacg tcaacagcac ctggagaacc     300
gtggaccgcc tctccgccac cgcctgcggc tgcctgggc                            339

<210> SEQ ID NO 2
```

<211> LENGTH: 474
<212> TYPE: DNA
<213> ORGANISM: Homo sapiens

<400> SEQUENCE: 2

```
cgccgccgca gccttctcgg cccgcgcccc cgccgcctgc accccatctg ctcttcccc      60
gcggggggccg cgcggcgcgg gctggggggcc cgggcagccg cgctcgggca gcggggggcgc  120
ggggctgccg cctgcgctcg cagctggtgc cgtgcgcgc gctcggcctg gccaccgct      180
ccgacgagct ggtgcgtttc cgcttctgca gcggctcctg ccgccgcgcg cgctctccac   240
acgacctcag cctggccagc ctactgggcg cggggggccct gcgaccgccc cgggctcccc   300
ggcccgtcag ccagccctgc tgccgaccca cgcgctacga agcggtctcc ttcatggacg   360
tcaacagcac ctggagaacc gtggaccgcc tctccgccac cgcctgcggc tgcctgggct   420
gagggctcgc tccagggctt tgcagactgg acccttaccg gtggctcttc ctgc         474
```

<210> SEQ ID NO 3
<211> LENGTH: 113
<212> TYPE: PRT
<213> ORGANISM: Homo sapiens

<400> SEQUENCE: 3

```
Ala Gly Gly Pro Gly Ser Arg Ala Arg Ala Ala Gly Ala Arg Gly Cys
1               5                   10                  15

Arg Leu Arg Ser Gln Leu Val Pro Val Arg Ala Leu Gly Leu Gly His
                20                  25                  30

Arg Ser Asp Glu Leu Val Arg Phe Arg Phe Cys Ser Gly Ser Cys Arg
            35                  40                  45

Arg Ala Arg Ser Pro His Asp Leu Ser Leu Ala Ser Leu Leu Gly Ala
        50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
                100                 105                 110

Gly
```

<210> SEQ ID NO 4
<211> LENGTH: 139
<212> TYPE: PRT
<213> ORGANISM: Homo sapiens

<400> SEQUENCE: 4

```
Pro Pro Gln Pro Ser Arg Pro Ala Pro Pro Ala Pro Pro Ser
1               5                   10                  15

Ala Leu Pro Arg Gly Gly Arg Ala Ala Arg Ala Gly Pro Gly Ser
                20                  25                  30

Arg Ala Arg Ala Ala Gly Ala Arg Gly Cys Arg Leu Arg Ser Gln Leu
            35                  40                  45

Val Pro Val Arg Ala Leu Gly Leu Gly His Arg Ser Asp Glu Leu Val
        50                  55                  60

Arg Phe Arg Phe Cys Ser Gly Ser Cys Arg Arg Ala Arg Ser Pro His
65                  70                  75                  80

Asp Leu Ser Leu Ala Ser Leu Leu Gly Ala Gly Ala Leu Arg Pro Pro
                85                  90                  95

Pro Gly Ser Arg Pro Val Ser Gln Pro Cys Cys Arg Pro Thr Arg Tyr
```

Glu Ala Val Ser Phe Met Asp Val Asn Ser Thr Trp Arg Thr Val Asp
            115                 120                 125

Arg Leu Ser Ala Thr Ala Cys Gly Cys Leu Gly
            130                 135

<210> SEQ ID NO 5
<211> LENGTH: 819
<212> TYPE: DNA
<213> ORGANISM: Homo sapiens

<400> SEQUENCE: 5
gagtttcccc tccacacagc taggagccca tgcccggcct gatctcagcc cgaggacagc      60
ccctccttga ggtccttcct ccccaagccc acctgggtgc cctctttctc cctgaggctc     120
cacttggtct ctccgcgcag cctgccctgt ggcccaccct ggccgctctg ctctgctga     180
gcagcgtcgc agaggcctcc ctgggctccg cgccccgcag ccctgccccc gcgaaggcc     240
ccccgcctgt cctggcgtcc ccgccggcc acctgccggg taggtgagag ggcgaggggg     300
cggggcgggg ctggcccggg acaccgcgcg tgactgggtc tcattccagg gggacgcacg     360
gcccgctggt gcagtggaag agcccggcgg ccgccgccgc agccttctcg gcccgcgccc     420
ccgccgcctg cacccccatc tgctcttccc cgcgggggcc gcgcggcgcg ggctggggc     480
ccgggcagcc gcgctcgggc agcggggggcg cggggctgcc gcctgcgctc gcagctggtg     540
ccggtgcgcg cgctcggcct gggccaccgc tccgacgagc tggtgcgttt ccgcttctgc     600
agcggctcct gccgccgcgc gcgctctcca cacgacctca gcctggccag cctactgggc     660
gccggggccc tgcgaccgcc ccgggctcc cggcccgtca gccagccctg ctgccgaccc     720
acgcgctacg aagcggtctc cttcatggac gtcaacagca cctggagaac cgtggaccgc     780
ctctccgcca ccgcctgcgg ctgcctgggc tgagggctc                           819

<210> SEQ ID NO 6
<211> LENGTH: 85
<212> TYPE: PRT
<213> ORGANISM: Homo sapiens

<400> SEQUENCE: 6

Met Pro Gly Leu Ile Ser Ala Arg Gly Gln Pro Leu Leu Glu Val Leu
1               5                   10                  15

Pro Pro Gln Ala His Leu Gly Ala Leu Phe Leu Pro Glu Ala Pro Leu
            20                  25                  30

Gly Leu Ser Ala Gln Pro Ala Leu Trp Pro Thr Leu Ala Ala Leu Ala
        35                  40                  45

Leu Leu Ser Ser Val Ala Glu Ala Ser Leu Gly Ser Ala Pro Arg Ser
    50                  55                  60

Pro Ala Pro Arg Glu Gly Pro Pro Val Leu Ala Ser Pro Ala Gly
65                  70                  75                  80

His Leu Pro Gly Arg
            85

<210> SEQ ID NO 7
<211> LENGTH: 159
<212> TYPE: PRT
<213> ORGANISM: Homo sapiens

<400> SEQUENCE: 7

Leu Gly Leu Ile Pro Gly Gly Arg Thr Ala Arg Trp Cys Ser Gly Arg
1               5                   10                  15

Ala Arg Arg Pro Pro Gln Pro Ser Arg Pro Ala Pro Pro Pro
            20                  25                  30

Ala Pro Pro Ser Ala Leu Pro Arg Gly Gly Arg Ala Ala Arg Ala Gly
        35                  40                  45

Gly Pro Gly Ser Arg Ala Arg Ala Ala Gly Ala Arg Gly Cys Arg Leu
        50                  55                  60

Arg Ser Gln Leu Val Pro Val Arg Ala Leu Gly Leu Gly His Arg Ser
65                  70                  75                  80

Asp Glu Leu Val Arg Phe Arg Phe Cys Ser Gly Ser Cys Arg Arg Ala
                85                  90                  95

Arg Ser Pro His Asp Leu Ser Leu Ala Ser Leu Leu Gly Ala Gly Ala
            100                 105                 110

Leu Arg Pro Pro Pro Gly Ser Arg Pro Val Ser Gln Pro Cys Cys Arg
            115                 120                 125

Pro Thr Arg Tyr Glu Ala Val Ser Phe Met Asp Val Asn Ser Thr Trp
        130                 135                 140

Arg Thr Val Asp Arg Leu Ser Ala Thr Ala Cys Gly Cys Leu Gly
145                 150                 155

<210> SEQ ID NO 8
<211> LENGTH: 1188
<212> TYPE: DNA
<213> ORGANISM: Homo sapiens

<400> SEQUENCE: 8
ctgatgggcg ctcctggtgt tgatagagat ggaacttgga cttggaggcc tctccacgct      60
gtcccactgc ccctggccta ggcggcaggt gagtggttct cccagtgact cctacctggt     120
actgaggaaa ggcggcttga ctggtgaggg agagcagggc ttggcttggg cagcggttag     180
gtgtgggagg gaaaatggtc agggagggac caggtgaatg ggaggaggag cgggacttct     240
ctgaatggtc ggtgcactca ggtgattcct ccctgggct cccagaggca gcaaacccat     300
tatactggaa cctaggccct tcctgagttt ccctccaca cagctaggag cccatgcccg     360
gcctgatctc agcccgagga cagccctcc ttgaggtcct cctcccaa gcccacctgg     420
gtgccctctt tctccctgag ctccacttg tctctccgc gcagcctgcc ctgtggccca     480
ccctggccgc tctggctctg ctgagcagcg tcgcagaggc ctccctgggc tccgcgcccc     540
gcagccctgc ccccgcgaa ggccccccgc ctgtcctggc gtcccccgcc ggccacctgc     600
cgggtaggtg agagggcgag ggggcgggc ggggctggcc cgggacaccg cgcgtgactg     660
ggtctcattc caggggacg cacggcccgc tggtgcagtg aagagcccg gcggccgccg     720
ccgcagcctt tcggcccgc gccccgcg cctgcacccc catctgctct ccccgcggg     780
ggccgcgcgg cgcgggctgg gggcccgggc agccgcgctc gggcagcggg ggcgcggggc     840
tgccgcctgc gctcgcagct ggtgccggtg cgcgcgctcg gcctgggcca ccgctccgac     900
gagctggtgc gtttccgctt ctgcagcggc tcctgccgcc gcgcgcgctc tccacacgac     960
ctcagcctgg ccagcctact gggcgccggg gcctgcgac cgcccccggg ctcccggccc    1020
gtcagccagc cctgctgccg acccacgcgc tacgaagcgg tctccttcat ggacgtcaac    1080
agcacctgga gaaccgtgga ccgctctctc gccaccgcct gcggctgcct gggctgaggg    1140
ctcgctccag ggctttgcag actggaccct taccggtggc tcttcctg                1188

<210> SEQ ID NO 9
<211> LENGTH: 228
<212> TYPE: PRT

<213> ORGANISM: Homo sapiens

<400> SEQUENCE: 9

```
Met Glu Leu Gly Leu Gly Gly Leu Ser Thr Leu Ser His Cys Pro Trp
1               5                   10                  15

Pro Arg Arg Gln Ala Pro Leu Gly Leu Ser Ala Gln Pro Ala Leu Trp
            20                  25                  30

Pro Thr Leu Ala Ala Leu Ala Leu Leu Ser Ser Val Ala Glu Ala Ser
        35                  40                  45

Leu Gly Ser Ala Pro Arg Ser Pro Ala Pro Arg Glu Gly Pro Pro
    50                  55                  60

Val Leu Ala Ser Pro Ala Gly His Leu Pro Gly Gly Arg Thr Ala Arg
65                  70                  75                  80

Trp Cys Ser Gly Arg Ala Arg Arg Pro Pro Gln Pro Ser Arg Pro
                85                  90                  95

Ala Pro Pro Pro Ala Pro Pro Ser Ala Leu Pro Arg Gly Gly Arg
                100                 105                 110

Ala Ala Arg Ala Gly Gly Pro Gly Ser Arg Ala Arg Ala Ala Gly Ala
            115                 120                 125

Arg Gly Cys Arg Leu Arg Ser Gln Leu Val Pro Val Arg Ala Leu Gly
    130                 135                 140

Leu Gly His Arg Ser Asp Glu Leu Val Arg Phe Arg Phe Cys Ser Gly
145                 150                 155                 160

Ser Cys Arg Arg Ala Arg Ser Pro His Asp Leu Ser Leu Ala Ser Leu
                165                 170                 175

Leu Gly Ala Gly Ala Leu Arg Pro Pro Gly Ser Arg Pro Val Ser
            180                 185                 190

Gln Pro Cys Cys Arg Pro Thr Arg Tyr Glu Ala Val Ser Phe Met Asp
        195                 200                 205

Val Asn Ser Thr Trp Arg Thr Val Asp Arg Leu Ser Ala Thr Ala Cys
210                 215                 220

Gly Cys Leu Gly
225
```

<210> SEQ ID NO 10
<211> LENGTH: 220
<212> TYPE: PRT
<213> ORGANISM: Homo sapiens

<400> SEQUENCE: 10

```
Met Glu Leu Gly Leu Gly Gly Leu Ser Thr Leu Ser His Cys Pro Trp
1               5                   10                  15

Pro Arg Arg Gln Pro Ala Leu Trp Pro Thr Leu Ala Ala Leu Ala Leu
            20                  25                  30

Leu Ser Ser Val Ala Glu Ala Ser Leu Gly Ser Ala Pro Arg Ser Pro
        35                  40                  45

Ala Pro Arg Glu Gly Pro Pro Val Leu Ala Ser Pro Ala Gly His
    50                  55                  60

Leu Pro Gly Gly Arg Thr Ala Arg Trp Cys Ser Gly Arg Ala Arg Arg
65                  70                  75                  80

Pro Pro Gln Pro Ser Arg Pro Ala Pro Pro Pro Ala Pro Pro
            85                  90                  95

Ser Ala Leu Pro Arg Gly Gly Arg Ala Ala Arg Ala Gly Gly Pro Gly
            100                 105                 110

Ser Arg Ala Arg Ala Ala Gly Ala Arg Gly Cys Arg Leu Arg Ser Gln
        115                 120                 125
```

```
Leu Val Pro Val Arg Ala Leu Gly Leu Gly His Arg Ser Asp Glu Leu
    130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
            180                 185                 190

Tyr Glu Ala Val Ser Phe Met Asp Val Asn Ser Thr Trp Arg Thr Val
        195                 200                 205

Asp Arg Leu Ser Ala Thr Ala Cys Gly Cys Leu Gly
    210                 215                 220

<210> SEQ ID NO 11
<211> LENGTH: 766
<212> TYPE: DNA
<213> ORGANISM: Homo sapiens

<400> SEQUENCE: 11
ctgatgggcg ctcctggtgt tgatagagat ggaacttgga cttggaggcc tctccacgct        60
gtcccactgc ccctggccta ggcggcaggc tccacttggt ctctccgcgc agcctgccct       120
gtggcccacc ctggccgctc tggctctgct gagcagcgtc gcagaggcct ccctgggctc       180
cgcgccccgc agccctgccc cccgcgaagg ccccccgcct gtcctggcgt ccccgccgg        240 ccacctgccg gggggacgca cggcccgctg gtgcagtgga agagcccggc ggccgccgcc       300
gcagccttct cggcccgcgc ccccgccgcc tgcacccccca tctgctcttc cccgcggggg       360
ccgcgcggcg cgggctgggg gcccgggcag ccgcgctcgg gcagcggggg cgcggggctg       420
ccgcctgcgc tcgcagctgg tgccggtgcg cgcgctcggc ctgggccacc gctccgacga       480
gctggtgcgt ttccgcttct gcagcggctc ctgccgccgc gcgcgctctc cacacgacct       540
cagcctggcc agcctactgg gcgccggggc cctgcgaccg ccccgggct cccggcccgt        600 cagccagccc tgctgccgac ccacgcgcta cgaagcggtc tccttcatgg acgtcaacag       660
cacctggaga accgtggacc gcctctccgc caccgcctgc ggctgcctgg gctgagggct       720
cgctccaggg ctttgcagac tggaccctta ccggtggctc ttcctg                      766

<210> SEQ ID NO 12
<211> LENGTH: 742
<212> TYPE: DNA
<213> ORGANISM: Homo sapiens

<400> SEQUENCE: 12
ctgatgggcg ctcctggtgt tgatagagat ggaacttgga cttggaggcc tctccacgct        60
gtcccactgc ccctggccta ggcggcagcc tgccctgtgg cccacccctgg ccgctctggc       120 tctgctgagc agcgtcgcag aggcctccct gggctccgcg ccccgcagcc ctgccccccg       180
cgaaggcccc ccgcctgtcc tggcgtcccc gccggccac ctgccggggg acgcacggc         240 ccgctggtgc agtggaagag cccggcggcc gccgccgcag ccttctcggc ccgcgccccc       300
gccgcctgca ccccccatctg ctcttccccg cggggccgc gcggcgcggg ctggggccc        360 gggcagccgc gctcgggcag cggggcgcg ggctgccgc ctgcgctcgc agctggtgcc        420
ggtgcgcgcg ctcggcctgg ccaccgctc cgacgagctg gtgcgtttcc gcttctgcag       480
cggctcctgc cgccgcgcgc gctctccaca cgacctcagc ctggccagcc tactgggcgc       540
cggggccctg cgaccgcccc cgggctcccg gcccgtcagc cagccctgct gccgacccac       600
```

```
gcgctacgaa gcggtctcct tcatggacgt caacagcacc tggagaaccg tggaccgcct    660
ctccgccacc gcctgcggct gcctgggctg agggctcgct ccagggcttt gcagactgga    720
cccttaccgg tggctcttcc tg                                             742
```

```
<210> SEQ ID NO 13
<211> LENGTH: 603
<212> TYPE: DNA
<213> ORGANISM: Homo sapiens

<400> SEQUENCE: 13
ctgatgggcg ctcctggtgt tgatagagat ggaacttgga cttggaggcc tctccacgct     60
gtcccactgc ccctggccta ggcggcaggg ggacgcacgg cccgctggtg cagtggaaga    120
gcccggcggc cgccgccgca gccttctcgg cccgcgcccc cgccgcctgc accccatct    180 gctcttcccc gcggggccg cgcggcgcg gctgggggcc cgggcagccg cgctcgggca    240 gcggggcgc ggggctgccg cctgcgctcg cagctggtgc cggtgcgcgc gctcggcctg    300
ggccaccgct ccgacgagct ggtgcgtttc cgcttctgca gcggctcctg ccgccgcgcg    360
cgctctccac acgacctcag cctggccagc ctactgggcg ccggggccct gcgaccgccc    420
ccgggctccc ggcccgtcag ccagccctgc tgccgaccca cgcgctacga agcggtctcc    480
ttcatggacg tcaacagcac ctggagaacc gtggaccgcc tctccgccac cgcctgcggc    540
tgcctgggct gagggctcgc tccagggctt tgcagactgg acccttaccg gtggctcttc    600
ctg                                                                  603
```

```
<210> SEQ ID NO 14
<211> LENGTH: 489
<212> TYPE: DNA
<213> ORGANISM: Homo sapiens

<400> SEQUENCE: 14
ctgatgggcg ctcctggtgt tgatagagat ggaacttgga cttggaggcc tctccacgct     60
gtcccactgc ccctggccta ggcggcagcc tgccctgtgg cccacccctgg ccgtctggc    120 tctgctgagc agcgtcgcag aggcctccct gggctccgcg ccccgcagcc ctgccccccg    180
cgaaggcccc ccgcctgtcc tggcgtcccc cgccggccac ctgccggcgg ctcctgccgc    240
cgcgcgcgct ctccacacga cctcagcctg gccagctac tgggcgccgg ggccctgcga    300
ccgcccccgg gctcccggcc cgtcagccag ccctgctgcc gacccacgcg ctacgaagcg    360
gtctccttca tggacgtcaa cagcacctgg agaaccgtgg accgcctctc cgccaccgcc    420
tgcggctgcc tgggctgagg gctcgctcca gggctttgca gactggaccc ttaccggtgg    480
ctcttcctg                                                            489
```

```
<210> SEQ ID NO 15
<211> LENGTH: 350
<212> TYPE: DNA
<213> ORGANISM: Homo sapiens

<400> SEQUENCE: 15
ctgatgggcg ctcctggtgt tgatagagat ggaacttgga cttggaggcc tctccacgct     60
gtcccactgc ccctggccta ggcggcagcg gctcctgccg ccgcgcgcgc tctccacacg    120
acctcagcct ggccagccta ctgggcgccg ggccctgcg accgccccg ggctcccggc    180 ccgtcagcca gccctgctgc cgacccacgc gctacgaagc ggtctccttc atggacgtca    240
acagcacctg gagaaccgtg gaccgcctct ccgccaccgc ctgcggctgc ctgggctgag    300
```
ggctcgctcc agggctttgc agactggacc cttaccggtg gctcttcctg            350

<210> SEQ ID NO 16
<211> LENGTH: 74
<212> TYPE: PRT
<213> ORGANISM: Homo sapiens

<400> SEQUENCE: 16

Ser Pro Asp Lys Gln Met Ala Val Leu Pro Arg Arg Glu Arg Asn Arg
1               5                   10                  15

Gln Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
        35                  40                  45

Asn Val Thr Asp Leu Gly Leu Gly Tyr Glu Thr Lys Glu Glu Leu Ile
    50                  55                  60

Phe Arg Tyr Cys Ser Gly Ser Cys Asp Ala
65                  70

<210> SEQ ID NO 17
<211> LENGTH: 20
<212> TYPE: PRT
<213> ORGANISM: Homo sapiens

<400> SEQUENCE: 17

Ala Glu Thr Thr Tyr Asp Lys Ile Leu Lys Asn Leu Ser Arg Asn Arg
1               5                   10                  15

Arg Leu Val Ser
            20

<210> SEQ ID NO 18
<211> LENGTH: 40
<212> TYPE: PRT
<213> ORGANISM: Homo sapiens

<400> SEQUENCE: 18

Asp Lys Val Gly Gln Ala Cys Cys Arg Pro Ile Ala Phe Asp Asp
1               5                   10                  15

Leu Ser Phe Leu Asp Asp Asn Leu Val Tyr His Ile Leu Arg Lys His
            20                  25                  30

Ser Ala Lys Arg Cys Gly Cys Ile
        35                  40

<210> SEQ ID NO 19
<211> LENGTH: 41
<212> TYPE: PRT
<213> ORGANISM: Homo sapiens

<400> SEQUENCE: 19

Ala Arg Leu Gly Ala Arg Pro Cys Gly Leu Arg Glu Leu Glu Val Arg
1               5                   10                  15

Val Ser Glu Leu Gly Leu Gly Tyr Ala Ser Asp Glu Thr Val Leu Phe
            20                  25                  30

Arg Tyr Cys Ala Gly Ala Cys Glu Ala
        35                  40

<210> SEQ ID NO 20
<211> LENGTH: 20
<212> TYPE: PRT
<213> ORGANISM: Homo sapiens -continued

```
<400> SEQUENCE: 20

Ala Ala Arg Val Tyr Asp Leu Gly Leu Arg Arg Leu Arg Gln Arg Arg
1               5                   10                  15

Arg Leu Arg Arg
            20

<210> SEQ ID NO 21
<211> LENGTH: 41
<212> TYPE: PRT
<213> ORGANISM: Homo sapiens

<400> SEQUENCE: 21

Glu Arg Val Arg Ala Gln Pro Cys Cys Arg Pro Thr Ala Tyr Glu Asp
1               5                   10                  15

Glu Val Ser Phe Leu Asp Ala His Ser Arg Tyr His Val His Glu
            20                  25                  30

Leu Ser Ala Arg Glu Cys Ala Cys Val
        35                  40

<210> SEQ ID NO 22
<211> LENGTH: 56
<212> TYPE: PRT
<213> ORGANISM: Homo sapiens

<400> SEQUENCE: 22

Ala Leu Ser Gly Pro Cys Gln Leu Trp Ser Leu Thr Leu Ser Val Ala
1               5                   10                  15

Glu Leu Gly Leu Gly Tyr Ala Ser Glu Glu Lys Val Ile Phe Arg Tyr
            20                  25                  30

Cys Ala Gly Ser Cys Pro Arg Gly Ala Arg Thr Gln His Gly Leu Ala
        35                  40                  45

Leu Ala Arg Leu Gln Gly Gln Gly
    50                  55

<210> SEQ ID NO 23
<211> LENGTH: 14
<212> TYPE: PRT
<213> ORGANISM: Homo sapiens

<400> SEQUENCE: 23

Arg Ala His Gly Gly Pro Cys Cys Arg Pro Thr Arg Tyr Thr
1               5                   10

<210> SEQ ID NO 24
<211> LENGTH: 26
<212> TYPE: PRT
<213> ORGANISM: Homo sapiens

<400> SEQUENCE: 24

Asp Val Ala Phe Leu Asp Asp Arg His Arg Trp Gln Arg Leu Pro Gln
1               5                   10                  15

Leu Ser Ala Ala Ala Cys Gly Cys Gly Gly
            20                  25

<210> SEQ ID NO 25
<211> LENGTH: 49
<212> TYPE: PRT
<213> ORGANISM: Homo sapiens

<400> SEQUENCE: 25

Ala Gly Gly Pro Gly Ser Arg Ala Arg Ala Ala Gly Ala Arg Gly Cys
1               5                   10                  15
```

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
            35                  40                  45

Arg

<210> SEQ ID NO 26
<211> LENGTH: 38
<212> TYPE: PRT
<213> ORGANISM: Homo sapeins

<400> SEQUENCE: 26

Ala Arg Ser Pro His Asp Leu Ser Leu Ala Ser Leu Leu Gly Ala Gly
1               5                   10                  15

Ala Leu Arg Pro Pro Gly Ser Arg Pro Val Ser Gln Pro Cys Cys
            20                  25                  30

Arg Pro Thr Arg Tyr Glu
            35

<210> SEQ ID NO 27
<211> LENGTH: 26
<212> TYPE: PRT
<213> ORGANISM: Homo sapiens

<400> SEQUENCE: 27

Ala Val Ser Phe Met Asp Val Asn Ser Thr Trp Arg Thr Val Asp Arg
1               5                   10                  15

Leu Ser Ala Thr Ala Cys Gly Cys Leu Gly
            20                  25

<210> SEQ ID NO 28
<211> LENGTH: 20
<212> TYPE: PRT
<213> ORGANISM: Homo sapiens

<400> SEQUENCE: 28

Met Glu Leu Gly Leu Gly Gly Leu Ser Thr Leu Ser His Cys Pro Trp
1               5                   10                  15

Pro Arg Arg Gln
            20

<210> SEQ ID NO 29
<211> LENGTH: 54
<212> TYPE: PRT
<213> ORGANISM: Homo sapiens

<400> SEQUENCE: 29

Ala Pro Leu Gly Leu Ser Ala Gln Pro Ala Leu Trp Pro Thr Leu Ala
1               5                   10                  15

Ala Leu Ala Leu Leu Ser Ser Val Ala Glu Ala Ser Leu Gly Ser Ala
            20                  25                  30

Pro Arg Ser Pro Ala Pro Arg Glu Gly Pro Pro Val Leu Ala Ser
            35                  40                  45

Pro Ala Gly His Leu Pro
            50

<210> SEQ ID NO 30
<211> LENGTH: 154
<212> TYPE: PRT
<213> ORGANISM: Homo sapiens -continued

```
<400> SEQUENCE: 30

Gly Gly Arg Thr Ala Arg Trp Cys Ser Gly Arg Ala Arg Pro Pro
1               5                   10                  15

Pro Gln Pro Ser Arg Pro Ala Pro Pro Pro Ala Pro Pro Ser Ala
            20                  25                  30

Leu Pro Arg Gly Gly Arg Ala Ala Arg Ala Gly Gly Pro Gly Ser Arg
        35                  40                  45

Ala Arg Ala Ala Gly Ala Arg Gly Cys Arg Leu Arg Ser Gln Leu Val
    50                  55                  60

Pro Val Arg Ala Leu Gly Leu Gly His Arg Ser Asp Glu Leu Val Arg
65                  70                  75                  80

Phe Arg Phe Cys Ser Gly Ser Cys Arg Arg Ala Arg Ser Pro His Asp
                85                  90                  95

Leu Ser Leu Ala Ser Leu Leu Gly Ala Gly Ala Leu Arg Pro Pro Pro
            100                 105                 110

Gly Ser Arg Pro Val Ser Gln Pro Cys Cys Arg Pro Thr Arg Tyr Glu
        115                 120                 125

Ala Val Ser Phe Met Asp Val Asn Ser Thr Trp Arg Thr Val Asp Arg
    130                 135                 140

Leu Ser Ala Thr Ala Cys Gly Cys Leu Gly
145                 150

<210> SEQ ID NO 31
<211> LENGTH: 23
<212> TYPE: DNA
<213> ORGANISM: Artificial
<220> FEATURE:
<223> OTHER INFORMATION: Primer PNHsp1

<400> SEQUENCE: 31
cggtgcactc aggtgattcc tcc                                          23

<210> SEQ ID NO 32
<211> LENGTH: 26
<212> TYPE: DNA
<213> ORGANISM: Artificial
<220> FEATURE:
<223> OTHER INFORMATION: Primer PNHsp2

<400> SEQUENCE: 32
ggcagcaaac ccattatact ggaacc                                       26

<210> SEQ ID NO 33
<211> LENGTH: 21
<212> TYPE: DNA
<213> ORGANISM: Artificial
<220> FEATURE:
<223> OTHER INFORMATION: Primer PNHsp3

<400> SEQUENCE: 33
cgctggtgca gtggaagagc c                                            21

<210> SEQ ID NO 34
<211> LENGTH: 22
<212> TYPE: DNA
<213> ORGANISM: Artificial
<220> FEATURE:
<223> OTHER INFORMATION: Primer PHNsp4

<400> SEQUENCE: 34
ctgcaccccc atctgctctt cc                                           22
```

```
<210> SEQ ID NO 35
<211> LENGTH: 22
<212> TYPE: DNA
<213> ORGANISM: Artificial
<220> FEATURE:
<223> OTHER INFORMATION: Primer PNHap1

<400> SEQUENCE: 35
gcaggaagag ccaccggtaa gg                                              22

<210> SEQ ID NO 36
<211> LENGTH: 22
<212> TYPE: DNA
<213> ORGANISM: Artificial
<220> FEATURE:
<223> OTHER INFORMATION: Primer PNHap2

<400> SEQUENCE: 36
ccagtctgca aagccctgga gc                                              22

<210> SEQ ID NO 37
<211> LENGTH: 22
<212> TYPE: DNA
<213> ORGANISM: Artificial
<220> FEATURE:
<223> OTHER INFORMATION: Primer PNHsp5

<400> SEQUENCE: 37
gcaagctgcc tcaacaggag gg                                              22

<210> SEQ ID NO 38
<211> LENGTH: 24
<212> TYPE: DNA
<213> ORGANISM: Artificial
<220> FEATURE:
<223> OTHER INFORMATION: Nested Primer PNHsp6

<400> SEQUENCE: 38
ggtgggggaa cagctcaaca atgg                                            24

<210> SEQ ID NO 39
<211> LENGTH: 25
<212> TYPE: DNA
<213> ORGANISM: Artificial
<220> FEATURE:
<223> OTHER INFORMATION: Forward Primer PNHexp-sp1

<400> SEQUENCE: 39
gcggatccgg ctgggggccc gggca                                           25

<210> SEQ ID NO 40
<211> LENGTH: 28
<212> TYPE: DNA
<213> ORGANISM: Artificial
<220> FEATURE:
<223> OTHER INFORMATION: Reverse Primer PNHexp-ap1

<400> SEQUENCE: 40
gcctcgagtc agcccaggca gccgcagg                                        28

<210> SEQ ID NO 41
<211> LENGTH: 39
<212> TYPE: PRT
<213> ORGANISM: Artificial
<220> FEATURE:
<223> OTHER INFORMATION: Plasmid NH2-terminal
```

-continued

```
<400> SEQUENCE: 41

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Ala Gly Gly Pro Gly Ser
        35

<210> SEQ ID NO 42
<211> LENGTH: 26
<212> TYPE: DNA
<213> ORGANISM: Artificial
<220> FEATURE:
<223> OTHER INFORMATION: Primer EVN(7)-sp1

<400> SEQUENCE: 42
ttcgcgtgtc tacaaactca actccc                                26

<210> SEQ ID NO 43
<211> LENGTH: 22
<212> TYPE: DNA
<213> ORGANISM: Artificial
<220> FEATURE:
<223> OTHER INFORMATION: Primer PNHap1

<400> SEQUENCE: 43
gcaggaagag ccaccggtaa gg                                    22

<210> SEQ ID NO 44
<211> LENGTH: 19
<212> TYPE: DNA
<213> ORGANISM: Artificial
<220> FEATURE:
<223> OTHER INFORMATION: Primer 1

<400> SEQUENCE: 44
acggttctcc aggtgctgt                                        19

<210> SEQ ID NO 45
<211> LENGTH: 15
<212> TYPE: DNA
<213> ORGANISM: Artificial
<220> FEATURE:
<223> OTHER INFORMATION: Primer 3

<400> SEQUENCE: 45
tgctgccgac ccacg                                            15

<210> SEQ ID NO 46
<211> LENGTH: 26
<212> TYPE: DNA
<213> ORGANISM: Artificial
<220> FEATURE:
<223> OTHER INFORMATION: TaqMan Probe 5

<400> SEQUENCE: 46
ctacgaagcg gtctccttca tggacg                                26

<210> SEQ ID NO 47
<211> LENGTH: 22
<212> TYPE: DNA
<213> ORGANISM: Artificial
<220> FEATURE:
<223> OTHER INFORMATION: Primer 2

<400> SEQUENCE: 47
```

```
cagagttaaa agcagccctg gt                                              22

<210> SEQ ID NO 48
<211> LENGTH: 22
<212> TYPE: DNA
<213> ORGANISM: Artificial
<220> FEATURE:
<223> OTHER INFORMATION: Primer 4

<400> SEQUENCE: 48
gaaggtgaag gtcggagtca ac                                              22

<210> SEQ ID NO 49
<211> LENGTH: 21
<212> TYPE: DNA
<213> ORGANISM: Artificial
<220> FEATURE:
<223> OTHER INFORMATION: TaqMan Probe 6

<400> SEQUENCE: 49
tttggtccgt attgggcgcc t                                               21
```

NEUROTROPHIC GROWTH FACTOR, ENOVIN

CROSS REFERENCE OF APPLICATION

This application is a continuation of U.S. patent application Ser. No. 09/357,349, filed Jul. 14, 1999, which claims the benefit of priority under 35 U.S.C. §119 from United Kingdom Patent Application No. 9815283.8, filed on Jul. 14, 1998, the contents of which are incorporated herein by reference, and is a continuation-in-part of U.S. patent application Ser. No. 09/327,668, filed on Jun. 8, 1999, and of U.S. patent application Ser. No. 09/248,772, filed on Feb. 12, 1999, the contents of which are incorporated herein by reference.

The present invention is concerned with a neurotrophic factor and, in particular, with cloning and expression of a novel member of the GDNF family of neurotrophic factors, designated herein as "enovin" (EVN).

INTRODUCTION

Neurotrophic factors are involved in neuronal differentiation, development and maintenance. These proteins can prevent degeneration and promote survival of different types of neuronal cells and are thus potential therapeutic agents for neurodegenerative diseases. Glial cell-line derived neurotrophic factor (GDNF) was the first member of a growing subfamily of neurotrophic factors structurally distinct from the neurotrophins. GDNF is a member of the transforming growth factor (TGF-β) superfamily of growth factors, characterized by a specific pattern of seven highly conserved cysteine residues within the amino acid sequence (Kingsley, 1994). GDNF was originally purified using an assay based on its ability to maintain the survival and function of embryonic ventral midbrain dopaminergic neurons in vitro (Lin et al., 1993). Other neuronal cell types in the central (CNS) or peripheral nervous systems (PNS) are also responsive to the survival effects of GDNF (Henderson et al., 1994, Buj-Bello et al., 1995, Mount et al., 1995, Oppenheim et al., 1995). GDNF is produced by cells in an inactive proform, which is cleaved specifically at a RXXR furin recognition site to produce active (mature) GDNF (Lin et al., 1993). Exogenous administration of GDNF has potent neuroprotective effects in animal models of Parkinson's disease, a common neurodegenerative disorder characterized by the loss of up to 70% of dopaminergic cells in the substantia nigra of the brain (Beck et al., 1995, Tomac et al., 1995, Gash et al., 1996, Choi-Lundberg et al., 1997, Bilang-Bleuel J. at al., 1997).

Recently, additional neurotrophic factors of the GDNF family have been discovered. Neurturin (NTN) was purified from conditioned medium from Chinese hamster ovary (CHO) cells using an assay based on its ability to promote the survival of sympathetic neurons in culture (Kotzbauer et al., 1996). The mature NTN protein is 57% similar to mature GDNF. Persephin (PSP) was discovered by cloning using degenerate primer PCR with genomic DNA as a template. The mature PSP, like mature GDNF, promotes the survival of ventral midbrain dopaminergic neurons and of motor neurons in culture (Milbrandt at al., 1998). The similarity of the mature PSP protein with mature GDNF and NTN is =50%. Artemin (ARTN) was discovered by DNA database searching and is a survival factor of sensory and sympathetic neurons in culture (Baloh et al, 1998b).

GDNF, NTN, PSP and ARTN require a heterodimeric receptor complex in order to carry out downstream intracellular signal transduction. GDNF binds to the GDNF family receptor alpha 1 (GFRα-1; GFRα Nomenclature Committee, 1997) subunit, a glycosyl-phosphatidyl-inositol (glycosyl-PtdIns) anchored membrane protein (Jing at al. 1996, Treanor at al. 1996, Sanicola et al 1997). The GDNF/GFRα-1 complex subsequently binds to and activates the cRET proto-oncogene, a membrane bound tyrosine kinase (Durbec et al. 1996, Trupp et al, 1996), resulting in the phosphorylation of tyrosine residues in cRET and subsequent activation of downstream signal transduction pathways (Worby et al., 1996). Several other members of the GFRα family of ligand binding receptors have been characterized (Baloh at al., 1997, Sanicola et al. 1997, Klein et al., 1997, Buj-Bello et al, 1997, Suvanto et al., 1997). GFRα-2 and GFRα-3 (Jing et al., 1997, Masure et al., 1998, Woby et al 1998, Naveilham et al., 1998, Baloh et al 1998a) have been identified by a number of different groups. GFRα-1 and GFRα-2 are widely expressed in almost all tissues and expression may be developmentally regulated (Sanicola et al., 1997, Widenfalk et al, 1997).

GFRα-3 is not expressed in the developing or adult central nervous system, but is highly expressed in several developing and adult sensory and sympathetic ganglia of the peripheral nervous system (Widenfalk et al, 1998, Naveilham et al., 1998, Baloh et al, 1998a). A fourth family member, GFRα-4, was cloned from chicken cDNA (Thompson et al., 1998). GFRα is the preferred receptor for GDNF, whereas GFRα-2 preferentially binds NTN (Jing et al., 1996, Treanor et al., 1996, Klein et al., 1997). Chicken GFRα-4 forms a functional receptor complex for PSP in combination with cRET (Enokido et al., 1998). Cells expressing both GFRα-3 and cRET were shown not to respond to either GDNF, NTN or PSP (Worby et al., 1998, Baloh et al., 1998a). Recently, ART has been shown to signal through cRET using GFRα-3 as the preferred ligand-binding receptor (Baloh et al 1998b). Cross-talk between the neurotrophic factors and GFRα receptors is possible in vitro, as GDNF can bind to GFRα-2 or GFRα-3 in the presence of cRET (Sanicola at al., 1997, Trupp et al, 1998) and NTN can bind to GFRα-1 with low affinity (Klein et al., 1997). In summary, GDNF, NTN, PSP and ART are part of a neurotrophic signalling system whereby different ligand-binding subunits (GFRα-1 to -4) can interact with the same Tyrosine kinase subunit (cRET). The physiological relevance of these in vitro findings was recently shown in gene knockout studies (reviewed by Rosenthal, 1999), which clearly show that GDNF interacts with GFRα-1 in vivo, whereas NTN is the preferred ligand for GFRα-2.

The present inventors have identified, cloned, expressed, chromosomally localized and characterized Enovin (EVN), the fourth member of the GDNF family. The knowledge of the mature EVN protein has been extended with the discovery of different functional and non-functional mRNA splice variants. Moreover, we present expression data, binding data of EVN to GFRc and in vitro effects of EVN on neurite outgrowth and protection against taxol-induced neurotoxicity in staurosporine-differentiated SH-SY5Y human neuroblastoma cell cultures.

SUMMARY OF THE INVENTION

In the present application, there is provided a nucleic acid molecule encoding a novel human neurotrophic growth factor, "enovin" an expression vector comprising said nucleic acid molecule, a host cell transformed with said vector, a neurotrophic growth factor encoded by said nucleic acid molecule, isolated enovin, compounds which act as agonists or antagonists of enovin and pharmaceutical compositions containing the nucleic acid or the enovin protein or the agonists or antagonists thereof.

DETAILED DESCRIPTION OF THE INVENTION

According to a first aspect of the present invention there is provided a nucleic acid molecule encoding a human neurotrophic growth factor, designated herein as enovin, having the amino acid sequence illustrated in FIG. 21, or encoding a functional equivalent, derivative or bioprecursor of said growth factor. Preferably, said nucleic acid molecule is DNA and even more preferably a cDNA molecule.

Preferably, the nucleic acid according to the invention comprises the sequence from positions 81 to 419 of the sequence illustrated in FIG. 1 and more preferably from positions 81 to 422 and even more preferably the complete sequence illustrated in FIG. 1.

The nucleic acid molecule from position 81 to 419 is believed to encode the sequence of the mature enovin protein subsequent to processing of the proform of the protein at the RXXR processing site present in the stable proform of said enovin protein.

There is also provided by the invention an antisense molecule capable of hybridising to any of the nucleic acid sequences according to the invention, under high stringency conditions, which would be well known to those skilled in the art.

Stringency of hybridisation as used herein refers to conditions under which polynucleic acids are stable. The stability of hybrids is reflected in the melting temperature (Tm) of the hybrids. Tm can be approximated by the formula:

$$81.5° C. - 16.6(\log 10[Na^+] + 0.41(\%G\&C) - 600/1$$

wherein 1 is the length of the hybrids in nucleotides. Tm decreases approximately by 1-1.5 C with every 1% decrease in sequence homology.

Advantageously, the nucleic acid molecule according to the invention may be used to express the human neurotrophic growth factor according to the invention, in a host cell or the like using an appropriate expression vector.

An expression vector according to the invention includes vectors capable of expressing DNA operatively linked to regulatory sequences, such as promoter regions, that are capable of effecting expression of such DNA fragments.

Regulatory elements required for expression include promoter sequences to bind RNA polymerase and transcription initiation sequences for ribosome binding. For example, a bacterial expression vector may include a promoter such as the lac promoter and for transcription initiation the Shine-Dalgarno sequence and the start codon AUG. Similarly, a eukaryotic expression vector may include a heterologous or homologous promoter for RNA polymerase II, a downstream polyadenylation signal, the start codon AUG and a termination codon for detachment of the ribosome. Such vectors may be obtained commercially or assembled from the sequences described by methods well known in the art.

Thus, an expression vector refers to a recombinant DNA or RNA construct, such as a plasmid, a phage, recombinant virus or other vector that upon introduction into an appropriate host cell results in expression of the DNA or RNA fragments. Appropriate expression vectors are well known to those skilled in the art and include those that are replicable in eukaryotic cells and/or prokaryotic cells and those that remain episomal or those which integrate into the host cell genome.

The antisense molecule capable of hybridising to the nucleic acid according to the invention may be used as a probe or as a medicament or in a pharmaceutical composition.

Nucleic acid molecules according to the invention may be inserted into the vectors described in an antisense orientation in order to provide for the production of antisense RNA. Antisense RNA or other antisense nucleic acids may be produced by synthetic means.

A further aspect of the invention comprises the host cell transformed, transfected or infected with the expression vector according to the invention, which cell preferably comprises a eukaryotic cell and more preferably a mammalian cell.

Incorporation of cloned DNA into a suitable expression vector for subsequent transformation of said cell and subsequent selection of the transformed cells is well known to those skilled in the art as provided in Sambrook et al (1989) Molecular Cloning, A Laboratory manual, Cold Spring Harbour Laboratory Press A further aspect of the present invention comprises a nucleic acid molecule having at least 15 nucleotides of the nucleic acid molecule according to the invention and preferably from 15 to 50 nucleotides.

These sequences may, advantageously be used as probes or primers to initiate replication or the like. Such nucleic acid molecules may be produced according to techniques well known in the art, such as by recombinant or synthetic means. They may also be used in diagnostic kits or devices or the like for detecting for the presence of a nucleic acid according to the invention. These tests generally comprise contacting the probe with a sample under hybridising conditions and detecting for the presence of any duplex formation between the probe and any nucleic acid in the sample.

According to the present invention these probes may be anchored to a solid support. Preferably, they are present on an array so that multiple probes can simultaneously hybridize to a single biological sample. The probes can be spotted onto the array or synthesized in situ on the array. (See Lockhart et al., Nature Biotechnology, vol. 14, December 1996 "Expression monitoring by hybridisation into high density oligonucleotide arrays"). A single array can contain more than 100, 500 or even 1,000 different probes in discrete locations.

Nucleic acid molecules according to the invention may also be produced using such recombinant or synthetic means, such as, for example, using PCR cloning mechanisms which generally involve making a pair of primers, which may be from approximately 10 to 50 nucleotides to a region of the gene which is desired to be cloned, bringing the primers into contact with mRNA, cDNA, or genomic DNA from a human cell, performing a polymerase chain reaction under conditions which bring about amplification of the desired region, isolating the amplified region or fragment and recovering the amplified DNA. Generally, such techniques as defined herein are well known in the art, such as described in Sambrook et al (Molecular Cloning: a Laboratory Manual, 1989).

The nucleic acids or oligonucleotides according to the invention may carry a revealing label. Suitable labels include radioisotopes such as $^{32}P$ or $^{35}S$, enzyme labels or other protein labels such as biotin or fluorescent markers. Such labels may be added to the nucleic acids or oligonucleotides of the invention and may be detected using known techniques per se.

Advantageously, human allelic variants or polymorphisms of the DNA molecule according to the invention may be identified by, for example, probing cDNA or genomic libraries from a range of individuals for example from different populations. Furthermore, nucleic acids and probes according to the invention may be used to sequence genomic DNA from patients using techniques well known in the art, such as the Sanger Dideoxy chain termination method, which may advantageously ascertain any predisposition of a patient to certain disorders associated with a growth factor according to the invention.

Further provided by the present invention is a transgenic cell, tissue or organism comprising a transgene capable of expressing the human neurotrophic factor enovin according to the invention.

The term "transgene capable of expression" as used herein means any suitable nucleic acid sequence which leads to expression of a neurotrophic factor having the same function and/or activity of a neurotrophic factor according to the invention. The transgene may include, for example, genomic nucleic acid isolated from human cells or synthetic nucleic acid including cDNA, integrated into the chromosome or in an extrachromosomal state.

Preferably, the transgene comprises a vector according to the invention, which vector includes a nucleic acid molecule encoding said neurotrophic factor, or a functional fragment of said nucleic acid molecule. A "functional fragment" of said nucleic acid should be taken to mean a fragment of the gene or cDNA encoding said neurotrophic factor or a functional equivalent thereof, which fragment is capable of being expressed to produce a functional neurotrophic growth factor according to the invention. Thus, for example, fragments of the neurotrophic growth factor according to the invention which correspond to the specific amino acid residues interacting with the corresponding receptor also form part of the present invention and which fragments may serve to function as agonists activating the corresponding receptor of the growth factor according to the invention so as to elicit its growth promoting and survival sustaining effects on cells. This aspect of the invention also includes differentially spliced isoforms and transcriptional starts of the nucleic acids according to the invention.

In accordance with the present invention, a defined nucleic acid includes not only the identical nucleic acid but also any minor base variations including in particular, substitutions in bases which result in a synonymous codon (a different codon specifying the same amino acid residue) due to the degenerate code in conservative amino acid substitutions. The term "nucleic acid molecule" also includes the complementary sequence to any single stranded sequence given regarding base variations.

According to a further aspect the invention provides an isolated human neurotrophic growth factor, encoded by a nucleic acid molecule as defined herein. Preferably, the growth factor comprises an amino acid sequence from position 27 to 139 of the amino acid sequence of FIG. 1 (SEQ ID NO. 3) or a functional equivalent, derivative or bioprecursor thereof. A "functional equivalent" as defined herein should be taken to mean a growth factor that exhibits all of the growth properties and functionality associated with the growth factor enovin. A "derivative" of enovin as defined herein is intended to include a polypeptide in which certain amino acids have been altered or deleted or replaced with other amino acids and which polypeptide retains the biological activity of enovin and/or which polypeptide can react with antibodies raised using enovin according to the invention as the challenging antigen.

Encompassed within the scope of the present invention are hybrid and modified forms of enovin, including fusion proteins and fragments. The hybrid and modified forms include, for example, when certain amino acids have been subjected to some modification or replacement, such as for example, by point mutation yet which modifications still result in a protein which retains the biological activity of enovin, according to the invention. Specific nucleic acid sequences can be altered by those of skill in the art to produce a growth factor exhibiting the same or substantially properties to enovin.

As is well known in the art, many proteins are produced in vivo with a (pre) signal sequence at the N-terminus of the protein. Furthermore, such proteins may comprise a further pro sequence that represents a stable precursor to the mature protein. Such pre and pro sequences are not generally necessary for biological activity. The enovin molecule according to the invention includes not only the full length sequence illustrated in FIG. 21 but from position 27 to 139, which follows the RXXR proteolytic processing site present in growth factors of this type and which is believed to represent the mature sequence of enovin.

A defined protein, polypeptide or amino acid sequence according to the invention includes not only the identical amino acid sequence but isomers thereof in addition to minor amino acid variations from the natural amino acid sequence including conservative amino acid replacements (a replacement by an amino acid that is related in its side chains). Also included are amino acid sequences which vary from the natural amino acid but result in a polypeptide which is immunologically identical or similar to the polypeptide encoded by the naturally occurring sequence.

Proteins or polypeptides according to the invention further include variants of such sequences, including naturally occurring allelic variants which are substantially homologous to said proteins or polypeptides. In this context, substantial homology is regarded as a sequence which has at least 70%, and preferably 80%, 90% or 95% amino acid homology with the proteins or polypeptides encoded by the nucleic acid molecules according to the invention. Neurotrophic growth factors expressed by the host cells according to the invention are also encompassed within the present invention.

The present invention is further directed to inhibiting the neurotrophic growth factor according to the invention in vivo by the use of antiserise technology. Antisense technology can be used to control gene expression through triple-helix formation or antisense DNA or RNA, both of which methods are based on binding of a polynucleotide to DNA or RNA. For example, the part of the DNA sequence coding for the mature protein of the present invention is used to design an antisense RNA oligonucleotide of from 10 to 50 base pairs in length. A DNA oligonucleotide is designed to be complementary to a region of the gene involved in transcription (triple-helix—see Lee et al. Nucl. Acids. Res., 6:3073 (1979); Cooney et al., Science, 241:456 (1988); and Dervan et al., Science, 251: 1360 (1991), thereby preventing transcription and the production of enovin. The antisense RNA oligonucleotide hybridises to the mRNA in vivo and blocks translation of an mRNA molecule into enovin.

Because of the sequence similarity between the growth factor described herein with previously identified growth factors of the GDNF family, enovin is also believed to be capable of promoting cell survival and growth and in treating disorders resulting from defects in function or expression of said neurotrophic factor.

The nucleic acid molecules or the neurotrophic factor according to the invention may, advantageously, therefore be used to treat or prevent neural disorders in a subject by administering to said subject an amount of a nucleic acid molecule or growth factor according to the invention in sufficient concentration to reduce the symptoms of said disorder. Thus, the nucleic acid molecules of the invention may be used to promote maintenance and survival of neuronal cells and for treating neuronal disorders or neurodegenerative conditions including Parkinson disease, Alzheimer's disease, peripheral neuropathy, amyatrophic lateral sclerosis, peripheral and central nerve trauma or injury and exposure to neurotoxins.

The neurotrophic growth factor according to the invention has, advantageously, been observed to confer a neurotrophic or neuroprotective effect on neuronal cells or cell populations, particularly those neuronal cells or cell populations which have been induced to undergo apoptosis. Accordingly, the nucleic acid or the enovin growth factor itself according to the invention may additionally be used in treating neurodegenerative disorders such as stroke, Huntingdons disease, peripheral neuropathy, acute brain injury nervous system tumours, multiple sclerosis, amyotrophic lateral sclerosis, peripheral nerve trauma, injury exposure to neurotoxins, multiple endocrine neoplasia, familial Hirschsprung disease, Prion associated diseases, Creutzfeld-Jacob disease by administering to a patient in need thereof, an amount of said nucleic acid or enovin in sufficient concentration to reduce or prevent the symptoms of the neural disorders described herein.

Additionally, and which is described in more details in the example below, enovin has been shown to speed up recovery of induced sensory deficits, which identifies enovin as a candidate for treating or alleviating pain syndromes with a peripheral or central neurogenic component, rheumatic/inflammatory diseases as well as conductance disturbances, by administration to a patient in need thereof in sufficient concentration to reduce or prevent the symptoms of these disorders.

An alternative method for treating the nerve disorders described above comprises implanting in a subject cells that express a human neurotrophic growth factor according to the invention such as the transgenic cell described herein.

The nucleic acid molecules and neurotrophic growth factor according to the invention may also be included in a pharmaceutical composition together with a pharmaceutically acceptable carrier, diluent or excipient therefor.

Antibodies to the neurotrophic factor of the present invention may, advantageously, be prepared by techniques which are known in the art. For example, polyclonal antibodies may be prepared by inoculating a host animal such as a mouse with the growth factor or an epitope thereof and recovering immune serum. Monoclonal antibodies may be prepared according to known techniques such as described by Kohier R. and Milstein C., Nature (1975) 256, 495-497.

Antibodies according to the invention may, advantageously, be used in a method of detecting for the presence of a growth factor according to the invention, which method comprises reacting the antibody with a sample and identifying any protein bound to said antibody. A kit is also provided for performing said method which comprises an antibody according to the invention and means for reacting the antibody with said sample.

Also provided by the present invention is a kit or device for detecting for the presence of a neurotrophic growth factor according to the invention in a sample, comprising an antibody as described above and means for reacting said antibody and said sample.

Proteins which interact with the neurotrophic factor of the invention, such as for example it's corresponding cellular receptor may be identified by investigating protein-protein interactions using the two-hybrid vector system which is well known to molecular biologists (Fields & Song, Nature 340: 245 1989). This technique is based on functional reconstitution in vivo of a transcription factor which activates a reporter gene. More particularly the technique comprises providing an appropriate host cell with a DNA construct comprising a reporter gene under the control of a promoter regulated by a transcription factor having a DNA binding domain and an activating domain, expressing in the host cell a first hybrid DNA sequence encoding a first fusion of a fragment or all of a nucleic acid sequence according to the invention and either said DNA binding domain or said activating domain of the transcription factor, expressing in the host at least one second hybrid DNA sequence, such as a library or the like, encoding putative binding proteins to be investigated together with the DNA binding or activating domain of the transcription factor which is not incorporated in the first fusion; detecting any binding of the proteins to be investigated with a protein according to the invention by detecting for the presence of any reporter gene product in the host cell; optionally isolating second hybrid DNA sequences encoding the binding protein.

An example of such a technique utilizes the GAL4 protein in yeast. GAL4 is a transcriptional activator of galactose metabolism in yeast and has a separate domain for binding to activators upstream of the galactose metabolizing genes as well as a protein binding domain. Nucleotide vectors may be constructed, one of which comprises the nucleotide residues encoding the DNA binding domain of GAL4. These binding domain residues may be fused to a known protein encoding sequence, such as for example the nucleic acids according to the invention. The other vector comprises the residues encoding the protein binding domain of GAL4. These residues are fused to residues encoding a test protein, preferably from the signal transduction pathway of the vertebrate in question. Any interaction between neurotrophic factor encoded by the nucleic acid according to the invention and the protein to be tested leads to transcriptional activation of a reporter molecule in a GAL-4 transcription deficient yeast cell into which the vectors have been transformed. Preferably, a reporter molecule such as β-galactosidase is activated upon restoration of transcription of the yeast galactose metabolism genes.

The receptor for enovin has been identified by the present inventors as GFRα3. Assays may therefore be prepared to identify agonist or antagonistic compounds of enovin. This assay may also be used in association with other neurotrophic growth factors and their corresponding receptors. Compounds identified may be used to treat or prevent disorders such as Parkinson's disease, Alzheimer's disease, neuronal disorders associated with expanded polyglutamine sequences, such as, Huntingdon's disease, peripheral neuropathy, acute brain injury, nervous system tumours, multiple sclerosis, amyotrophic lateral sclerosis, peripheral nerve trauma or injury exposure to neurotoxins, multiple endocrine neoplasia and familial Hirschsprung disease, Prion associated diseases, Creutzfeld-Jacob disease, stroke, pain syndromes with a substantially peripheral or central neurogenic component, rheumatic/inflammatory diseases as well as conductance disturbances by administering to an individual an amount of said agonist or antagonist in sufficient concentration to prevent or treat said neural disorders. Such compounds may also be included in pharmaceutical compositions together with a pharmaceutically acceptable carrier, diluent or excipient therefor.

Agonists or antagonists of a growth factor (such as for example enovin) may be identified in one embodiment by contacting a cell tissue or organism expressing an appropriate receptor and cRET with a candidate compound in the presence of the growth factor and comparing the levels of RET activation in said cell, tissue or organism with a control which has not been contacted with said candidate compound.

An alternative embodiment of the invention comprises a method of identifying agonists or antagonists of a neurotrophic growth factor said method comprising contacting a cell tissue or organism expressing an appropriate receptor of said growth factor and cRET with a candidate compound in the presence of said growth factor, measuring the level of activation of a signalling kinase in the signal transduction pathway of which said appropriate receptor is a component following addition of an antibody specific for said signal kinase conjugated to a reporter molecule compared to a cell tissue or organism which has not been contacted with said compound.

A further aspect of the invention comprises use of a compound identified as an antagonist according to the invention in the manufacture of a medicament for treating gastrointestinal disorders or conditions mediated by increased peristaltic intestinal movement.

The compounds identified in the assays of the present invention may advantageously be used to enhance the gastrointestinal motility and therefore may be useful in treating conditions related to a hampered or impaired gastrointestinal transit.

Accordingly, such compounds may be useful in treating warm-blooded animals, including humans, suffering from conditions related to a hampered or impaired gastric emptying or more generally suffering from conditions related to a hampered or impaired gastrointestinal transit. Consequently a method of treatment is provided for relieving patients from conditions, such as, for example, gastrooescphageal reflux, dyspepsia, gastroparesis, post-operative ileus, and intestinal pseudo-obstruction.

Dyspepsia is an impairment of the function of digestion, that can arise as a symptom of a primary gastrointestinal dysfunction, especially a gastrointestinal dysfunction related to an increased muscle tone or as a complication due to other disorders such as appendicitis, gallbladder disturbances, or malnutrition. Dyspeptic symptoms are for example a lack of appetite, feeling of fullness, early satiety, nausea, vomiting and bloating.

Gastroparesis can be brought about by an abnormality in the stomach or as a complication of diseases such as diabetes, progressive systemic sclerosis, anorexia, nervosa and myotonic dystrophy.

Post-operative ileus is an obstruction or a kinetic impairment in the intestine due to a disruption in muscle tone following surgery. Intestinal pseudo-obstruction is a condition characterized by constipation, colicky pain, and vomiting, but without evidence of physical obstruction.

The compounds of the present invention can thus be used either to take away the actual cause of the condition or to alleviate the symptoms of the conditions.

Additionally some of the compounds being stimulators of kinetic activity on the colon, may be useful to normalize or to improve the intestinal transit in subjects suffering from symptoms related to disturbed motility, e.g. a decreased peristalsis of the small and large intestine alone or in combination with delayed gastric emptying.

In view of the colon kinetic utility of the compounds of the present invention, there is provided a method of treating warm-blooded animals, including humans, suffering from motility disorders of the intestinal system, such as, for example, constipation, pseudo-obstruction, intestinal atony, post-operative intestinal atony, irritable bowel syndrome (IBS), and drug-induced delayed transit.

Compounds identified as antagonists according to the assays of the present invention may also be of potential use in the treatment or prophylaxis of gastrointestinal conditions resulting from increased peristaltic movements in the intestines such as diarrhea (including secretory diarrhea, bacterial induced diarrhea, choleic diarrhea, traveller's diarrhea and psychogenic diarrhea), Crohn's disease, spastic colon, irritable bowel syndrome (IBS), diarrheapredominant irritable bowel gastrointestinal hypersensitivity.

In view of the utility of the compounds of the invention, it follows that the present invention also provides a method of treating warm-blooded animals, including humans suffering from gastrointestinal conditions such as irritable bowel syndrome (IBS), especially the diarrhea aspects of IRS. Consequently a method of treatment is provided for relieving patients suffering from conditions such as irritable bowel syndrome (IBS), diarrheapredominant irritable bowel syndrome, bowel hypersensitivity, and the reduction of pain associated with gastrointestinal hypersensitivity.

The present compounds may also be of potential use in other gastrointestinal disorders, such as those associated with upper gut motility, and as antiemetics for treating emesis, and cytotoxic drug and radiation induced emesis.

Inflammatory bowel diseases include, for example, ulcerative colitis, Crohn's disease and the like.

A further aspect of the invention also comprises a method of treating a disorder mediated by expression of enovin according to the invention by administering to a patient an amount of an antisense molecule or an antagonist thereof according to the invention in sufficient concentration to alleviate or reduce the symptoms of said disorder.

Disorders mediated by inactivation or inhibiting expression of enovin may also advantageously be treated by administering to an individual an amount of a compound identified as an agonist of enovin in sufficient concentration to reduce or prevent the symptoms of the disorder.

In a further aspect, the invention provides a method for making a pharmaceutical formulation for the treatment of diseases associated with human neurotrophic growth factor enovin, said method comprising, selecting a candidate compound identified as an agonist or antagonist of enovin according to the invention, manufacturing bulk quantities of said compound and formulating the compound manufactured in a pharmaceutically acceptable carrier.

As will be seen in more detail from the examples below, enovin has been successful in reducing taxol induced sensory deficits. Enovin may therefore play a possible role in pain syndromes with a substantially peripheral and central neurogenic component, rheumatic diseases as well as conductance disturbances and can play a modulatory role in sensory processes after transdermal, topical, local central (such as epidural, inithrateal, ICV, intraplexus, intraneuronal) per oral, rectal and systemic application. Therefore, in the same manner as described herein for other conditions mediated by enovin, these conditions may be alleviated or even prevented by administering either an antisense molecule, a nucleic acid, enovin protein, pharmaceutical composition, or a compound identified as an agonist or an antagonist, as appropriate, according to the invention, in sufficient concentrations to alleviate or prevent the symptoms of said disorder(s).

The therapeutic or pharmaceutical compositions of the present invention can be administered by any suitable route known in the art including for example intravenous, subcutaneous, intramuscular, transdermal, intrathecal or intracerebral or administration to cells in ex viva treatment protocols. Administration can be either rapid as by injection or over a period of time as by slow infusion or administration of slow release formulation. For treating tissues in the central nervous system, administration can be by injection or infusion into the cerebrospinal fluid (CSF).

Enovin can also be linked or conjugated with agents that provide desirable pharmaceutical or pharmacodynamic properties. For example, it can be coupled to any substance known in the art to promote penetration or transport across the blood-brain barrier such as an antibody to the transferrin receptor, and administered by intravenous injection.

Enovin, the antisense molecules or indeed the compounds identified as agonists or antagonists of enovin according to the invention may be used in the form of a pharmaceutical composition, which may be prepared according to procedures well known in the art. Preferred compositions include a pharmaceutically acceptable vehicle or diluent or excipient, such as for example, a physiological saline solution. Other pharmaceutically acceptable carriers including other non-toxic salts, sterile water or the like may also be used. A suitable buffer may also be present allowing the compositions to be lyophilized and stored in sterile conditions prior to reconstitution by the addition of sterile water for subsequent administration. Incorporation of enovin into a solid or semi-solid biologically compatible matrix may be carried out which can be implanted into tissues requiring treatment.

The carrier can also contain other pharmaceutically acceptable excipients for modifying other conditions such as pH, osmolarity, viscosity, sterility, lipophilicity, solubility or the like. Pharmaceutically acceptable excipients which permit sustained or delayed release following administration may also be included.

The enovin protein or the nucleic acid molecules or compounds according to the invention may be administered orally. In this embodiment they may be encapsulated and combined with suitable carriers in solid dosage forms which would be well known to those skilled in the art.

As would be well known to those of skill in the art, the specific dosage regime may be calculated according to the body surface area of the patient or the volume of body space to be occupied, dependent upon the particular route of administration to be used. The amount of the composition actually administered will, however, be determined by a medical practitioner, based on the circumstances pertaining to the disorder to be treated, such as the severity of the symptoms, the composition to be administered, the age, weight, and response of the individual patient and the chosen route of administration.

The present invention may be more clearly understood by the following examples which are purely exemplary and by reference to the accompanying drawings wherein:

FIG. 1 is partial cDNA sequence of a neurotrophic factor according to the invention designated as enovin. The consensus sequence was obtained by PCR amplification with primers PNHsp3 and PNHap 1 on different cDNAs and on genomic DNA followed by cloning and sequence analysis and comparison of the obtained sequences. The predicted one letter code amino acid sequence is shown above the DNA sequence. The nucleotide residue number is shown on the right of the DNA sequence, whereas the amino acid residue number is shown to the right of the translated protein sequence. The putative RXXR cleavage site for the prodomain is indicated in bold and underlined. The putative start of the mature protein is indicated by an arrow. The seven conserved cysteine residues characteristics for all members of the TGF-β family are indicated in bold: A potential N-glycosylation site is double underlined.

FIG. 2 (SEQ ID NOS. 16, 17, 18, and 19) is alignment of the predicted mature protein sequences of human GDNF, NTN, PSP and EVN. The sequences were aligned using the ClustalW alignment program. Amino acid residues conserved between all three proteins are included in the black areas. Residues conserved between two or three of the sequences are shaded in grey. The 7 conserved cysteine residues characteristic for members of the TGF-β family are indicated by asterisks above the sequence. Amino acid residues are numbered to the right. The dashes indicate gaps introduced into the sequence to optimize the alignment.

FIG. 3 (SEQ ID NO. 5) is partial cDNA sequence of enovin. The consensus sequence was obtained by PCR amplification (primary PCR with primers PNHsp1 and PNHap1 and nested PCR with primers PNHsp2 and PNHap2) on different cDNAs followed by cloning and sequence analysis and comparison of the obtained sequences. The translated one letter code amino acid sequence of nucleotides 30 to 284 (reading frame A) is shown above the sequence and numbered to the right (A1 to A85). This reading frame contains a putative ATG translation start codon. The translated one letter code amino acid sequence of nucleotides 334 to 810 (reading frame B) is shown above the sequence and numbered to the right (B1 to B159). This reading frame contains the region of homology with GDNF, NTN and PSP. The nucleotide residue number is shown to the right of the DNA sequence. The putative RXXR cleavage site for the prodomain is indicated in bold and underlined. The putative start of the mature protein is indicated by an arrow. The seven conserved cysteine residues characteristic for all members of the TGF-β family are indicated in bold. A potential N-glycosylation site is double underlined, FIG. 4 is an illustration of the chromosomal localisation of human Enovin. (A) Diagram of FISH mapping results for Enovin. Each dot represents the double FISH signals detected on human chromosome 1, region p31.3-p32. (B) Example of FISH mapping of Enovin. The left panel shows the FISH signals on chromosome 1. The right panel shows the same mitotic figure stained with 4',6-diamidino-2-phenylindole to identify chromosome 1, FIG. 5 is an illustration of expression of Enovin in different human tissues. (A), (B), (C) Northern blot analysis of tissue expression of Enovin. The expression of Enovin mRNA in different human tissues was assessed using a probe corresponding to part of the coding region of Enovin (including the region coding for the mature Enovin protein) to analyse blots of human poly(A) rich RNA. (A) Multiple Tissue Northern (MTN) blot; (B) MTN blot II) Fetal MTN blot II. Panel (D) shows an autoradiography of the human RNA master blot probed with the same Enovin cDNA fragment. Panel (E) shows the location of human tissue mRNA samples on the RNA master blot from (D), FIG. 6 is a graphic illustration of the total survival of SH-SY5Y cells after 72 hours treatment with 10-6 M taxol and the effect of increasing doses of enovin on this survival, normalized to the condition of solvent. SH-SY5Y cells are differentiated for 5 days with 25 nM staurosporine before application of taxol. Data are from two independent experiments in sixtuplate. Mean and st. dev. is shown, FIG. 7 is a graphic representation of the effect of increasing concentrations of enovin over 48 hours on neurite outgrowth of staurosporine—differentiated SH-SY5Y cells, normalized to the condition of solvent, SH-SY5Y cells are differentiated for 5 days with 25 nM staurosporine before starting the 48 hour experiment. As a positive control, the differentiating effect of 25 nM staurosporine is shown. Neurite length is calculated on at least 5000 cells. Data is provided from the experiments performed in duplicate. Mean and st. dev. is shown.

FIGS. 8 to 18 are graphic representations of the effect of enovin on proliferation of various cell types.

FIG. 19 is a graphic representation of the effects of enovin on taxol-induced sensory deficits using the pin prick test. Given are the average (±1 SEM) cumulative scores over time of rats treated with either 2 different doses of enovin 23 or 130 µg/ml; n=10 rats/group) or vehicle/saline (n=20 rats) after taxol. Enovin or saline/vehicle were injected in a volume of 75 µl in the subplantar area of the right hind paw.

FIG. 20 is a graphic representation of the effects of enovin on taxol-induced sensory deficits using the pin prick test. Given are the average (±1 SEM) cumulative scores over time of rats treated with either 2 different doses of enovin (23 or 130 µg/ml; n=10 rats/group) or vehicle/saline (n=20 rats) before taxol. Enovin or saline/vehicle were injected in a volume of 75 µl in the subplantar area of the right hind paw.

FIG. 21 is a DNA sequence of enovin. The consensus sequence was obtained, by amplification with PCR using primers PNHsp5 and PNHap1 on human frontal cortex cDNA and on human genomic DNA followed by cloning, sequence analysis and comparison of the resultant sequences. The predicted amino acid sequence is shown above the DNA sequence for the only splice variant yielding a functional Enovin protein after translation. The nucleotide residue number is shown to the left of the DNA sequence, whereas the amino acid residue number is shown to the right of the translated protein sequence. 5' and 3' splice sites detected by comparison of sequenced cDNA fragments with the genomic sequence are indicated by vertical lines bending to the left or right, respectively, and are numbered consecutively. The putative RXXR furin cleavage site for the prodomain is indicated in bold and underlined. The putative start of the mature protein is indicated by an arrow. The seven conserved cysteine residues characteristic for all members of the TGF-β family are indicated in bold. A potential N-linked glycosylation site is double underlined. The 5' and 3' splice sites are numbered and encircled.

FIG. 22 is an illustration of expression of different Enovin splice variants in human tissues. (A) schematic diagram of Enovin splice variants identified by RT-PRC experiments with Enovin specific primers on RNA derived from different human tissues followed by cloning and sequence analysis of PCR products. The top line shows a scale (in bp). The second line represents the Enovin genomic sequence. The position of the translation start and stop codon, of the start of the mature Enovin coding sequence and of the 5' and 3' splice sites (see FIG. 21) are indicated. The right part of the figure shows the PCR products obtained by RT-PCR on ovary and on frontal cortex RNA together with a 100 bp DNA ladder. The position of the different mRNA variants is indicated together with their size (from start to stop codon). The translated proteins are shown on the left hand side. Boxes delineate regions represented in the cDNA. Dashed lines represent spliced out genomic DNA. The shaded region represents the mature Enovin coding sequence. The dotted line marks the start of the mature Enovin coding sequence. The two transcripts capable of yielding functional Enovin protein are indicated by an asterisk at the left hand side. (B) Tissue distribution of the main splice variants. The photograph shows the PCR fragments obtained by RT-PCR with Enovin specific primers on different human cDNAs. The 4 main splice variants (A to D) are indicated by arrows at the left hand side. Sizes are indicated on the right hand side based on the 100 bp DNA ladder used as size reference on the gel.

FIG. 23 Predicted protein sequence of the long splice variant of Enovin, obtained by splicing out the two introns from the DNA sequence of FIG. 21. Splice sites 5'1 and 3'-1 are used to remove the first intron and splice sites 5'-2 and 3'-3 are used to remove the second intron. This results in a cDNA sequence having an open reading frame coding for the 228 amino acid residue protein shown above.

FIG. 24 Predicted protein sequence of an alternative (short) splice variant of Enovin, obtained by splicing out the two introns from the DNA sequence of FIG. 21. Splice sites 5'-1 and 3'-2 are used to remove the first intron and splice sites 5'-2 and 3'-3 are used to remove the second intron. This results in a cDNA sequence having an open reading frame coding for the 220 amino acid residue protein shown above. This protein sequence misses 8 amino acid. residues compared to the sequence of FIG. 23.

Deposits

Figure 3:

Plasmid EVNmat/pRSETB including the DNA sequence encoding enovin, was deposited on 6 May 1999 under Accession No. LMBP3931, at the Belgian Coordinated Collections of Micro-Biologie (BCCM) at Laboratorium voor Moleculaire—Plasmidencollectie (LMBP) B9000, Ghent, Selgium, in accordance with the provisions of the Budapest Treaty of 28 Apr. 1997. Materials and methods Materials Native Taq polymerase, ampicillin, IPTG (isopropyl-β-D-thiogalactoside), X-gal (5-bromo-4-chloro-3-indolyl-β-D-galactopyranoside) and all restriction enzymes used were from Boehringer Mannheim (Mannheim, Germany). 10 mM dNTP mix was purchased from Life Technologies (Gaithersburg, Md., USA). The TOPO-TA cloning kit was purchased from Invitrogen BV (Leek, The Netherlands). The Qiagen plasmid mini- or midi-DNA purification kit, the Qiaprep Spin Miniprep kit and the Qiaquick gel extraction kit were purchased from Qiagen GmbH (Dusseldorf, Germany). cDNA libraries, Marathon™ Ready cDNA kits, human multiple tissue cDNA (MTC™) panels I and II multiple tissues northern blots and the Advantage-GC cDNA PCR kit were obtained from Clontech Laboratories (Palo Alto, Calif., USA). All PCR reactions were performed in a GeneAmp PCR system 9600 cycler (Perkin Elmer, Foster City, Calif., USA). LB (Luria-Bertani) medium consists of 10 g/l of tryptone, 5 g/l of yeast extract and 10 g/l of NaC1.2× YT/ampicillin plates consist of 16 g/l of tryptone, 10 g/l of yeast extract, 5 g/l of NaC1, 15 g/l of agar and 100 mg/i of ampicillin.

Database Homology Searching and Sequence Comparison.

Using the complete human glial cell-line derived neurotrophic factor (GDNF; accession no. Q99748), neurturin (NTN; accession no. P39905) and persephin (PSP; accession no. AF040962) cDNA derived protein sequences as query sequences, a BLAST (Basic Local Alignment Search Tool; Altschul et al., 1990) search was performed on the daily update of the EMBL/GenBank human expressed sequence tag (EST) and genomic databases.

Additional BLAST searches were performed using the genomic sequence with accession no. AC005038 and several ESTs present in the GenBank database and showing homology to this genomic sequence were detected.

The percentage identity and percentage similarity between members of the GDNF family was calculated by pairwise comparison of the sequences using the BESTFIT program (Genetics Computer Group sequence analysis software package, version 8.0, University of Wisconsin, Madison, Wis., USA). Alignments of DNA or protein sequences were done with the ClustalW alignment program (EMBL, Heidelberg, Germany).

Oligonucleotide Synthesis for PCR and DNA Sequencing.

All oligonucleotide primers were ordered from Eurogentec (Seraing, Belgium). Insert-specific sequencing primers (15- and 16-mers) and primers for use in PCR reactions were designed manually. DNA was prepared on Qiagen-tip-20 or -100 anion exchange or Qiaquick spin columns (Qiagen GrnbH, Dusseldorf, Germany) and recovered from the columns in 30 µl TE-buffer (10 mM Tris.HCl, 1 mM EDTA (sodium salt), pH 8.0).

Sequencing reactions were done on both strands using the ABI prism BigDye Terminator Cycle sequencing kit and were run on an Applied Biosystems 377XL sequencer (Perkin Elmer, ABI Division, Foster City, Calif., USA). The Sequencher™ software was used for sequence assembly and manual editing (GeneCodes, Ann Arbor, Mich., USA).

Cloning of a Novel GDNF Homologue.

A DNA region spanning nucleotides 67411 to 68343 of EMBL accession no. AC005038 of which the translated protein sequence was homologous to mature NTN and PSP was used to design oligonucleotide primers for PCR amplification. The different primers used are shown in Table 1.

TABLE 1

Primers used for the PCR amplification of fragments of AC005038.

| Primer name | Primer sequence | SEQ ID NO: |
|---|---|---|
| PNHsp1 | 5'-CGGTGCACTCAGGTGATTCCTCC-3' | SEQ ID NO: 31 |
| PNHsp2 | 5'-GGCAGCAAACCCATTATACTGGAACC-3' | SEQ ID NO: 32 |
| PNHsp3 | 5'-CGCTGGTGCAGTGGAAGAGCC-3' | SEQ ID NO: 33 |
| PNHsp4 | 5'-CTGCACCCCCATCTGCTCTTCC-3' | SEQ ID NO: 34 |
| PNHap1 | 5'-GCAGGAAGAGCCACCGGTAAGG-3' | SEQ ID NO: 35 |
| PNHap2 | 5'-CCAGTCTGCAAAGCCCTGGAGC-3' | SEQ ID NO: 36 |

Primers PNHsp3 and PNHap1 were used to amplify a fragment of 502 bp on cDNA derived from different human tissues (fetal brain, whole fetus, prostate or lung Marathon-Ready™ cDNA (Clontech Laboratories), frontal cortex, hippocampus and cerebellum cDNA) and on human genomic DNA. Based on the genomic sequence from the EMBL/GenBank database (acc. no. AC005038), the fragment to be amplified was predicted to have a G+C content of 76%. Therefore, amplifications were done using the Advantage-GC cDNA PCR kit (Clontech Laboratories, Palo Alto, Calif., USA) optimized for the amplification of GC-rich DNA sequences. PCR reactions were performed in a total volume of 50 µl, containing 1× GC cDNA PCR reaction buffer, 0.2 mM dNTP, 1 M GC-MELT™, 200 nM of primers PNHsp3 and PNRap1, 1 µl of Advantage KlenTaq polymerase mix and 1 to 5 µl of cDNA or 0.5 µg of genomic DNA. Samples were heated to 95° C. for 5 min and cycling was done for 45 s at 95° C., 1 mm at 58° C. and 40 s at 72° C. for 35 cycles, with a final step of 7 min at 72° C. Samples were finally treated with 2.5 U of native Taq DNA polymerase to add an A-overhang. PCR products were analysed on a 1% (w/v) agarose gel in 1× TAE buffer (40 mM Tris-acetate, 1 mM EDTA (sodium salt), pH 8.3). PCR fragments of the expected size (495 bp) were excised from the gel and purified with the Qiaquick gel extraction kit. The PCR fragments were sequenced to confirm their identity and cloned into the plasmid vector pCR2.1-TOPO using the TOPO TA cloning kit according to manufacturer's instructions. Approximately 20 ng of purified fragment was combined with 1 µl pCR2.1-TOPO vector in a total volume of 5 µl. Reactions were incubated at room temperature (20° C.) for 5 min. 2 µl of the reaction was transformed into TOP1OF' competent cells (Invitrogen BV) using heat-shock transformation and plated on 2× YT/ampicillin plates supplemented with 10 mM IPTG and 2% (w/v) X-gal for blue-white screening. White colonies after overnight growth were picked from the plates, grown in 5 ml of LB medium supplemented with 100 mg/l ampicillin and plasmid DNA prepared using the Qiaprep Spin Miniprep kit. The presence of an insert of the expected size was confirmed by restriction digestion with EcoRI. The plasmid insert of several positive clones was sequenced and the obtained sequences compared using the ClustalW alignment program.

To obtain additional coding sequence for the novel GDNF homologue, a fragment with an expected size of 931 bp based on the EMBL/GenBank sequence (acc. no. AC005038) was amplified by PCR using primers PNHsp1 and PNHap1. PCR reactions were performed in a total volume of 50 µl, containing 1× GC cDNA PCR reaction buffer, 0.2 mM dNTP, 1 M GC-MELT™, 200 nM of primers PNHsp1 and PNHap1, 1 µl of Advantage KlenTaq polymerase mix and 1 to 5 µl of cDNA from cerebellum, frontal cortex or hippocampus or 0.5 µl of genomic DNA. Samples were heated to 95° C. for 5 min and cycling was done for 45 s at 95° C., 1 min at 58° C. and 1 min 30 s at 72° C. for 35 cycles, with a final step of 7 min at 72° C. PCR products were analysed on a 1% (w/v) agarose gel in 1× TAE buffer (40 mM Tris-acetate, 1 mM EDTA (sodium salt), pH 8.3). A second round amplification was performed with nested primers (PNHsp2 and PNHap2). 1 µl of the first round amplification reaction was used in a total volume of 50 µl, containing 1× GC cDNA PCR reaction buffer, 0.2 mM dNTP, 1 M GC-MELT™, 200 nM of primers PNHsp2 and PNHap2 and 1 µl of Advantage KlenTaq polymerase mix. Samples were heated to 95° C. for 5 min and cycling was done for 45 s at 95° C., 1 min at 58° C. and 1 min 30 s at 72° C. for 35 cycles, with a final step of 7 min at 72° C. Samples were analysed on a 1% (w/v) agarose gel in 1× TAE buffer. PCR fragments of the expected size (870 bp) were excised from the gel and purified with the Qiaquick gel extraction kit. The PCR fragments were sequenced to confirm their identity, treated with 2.5 U of Tag polymerase and cloned into the plasmid vector pCR2.1-TOPO using the TOPO TA cloning kit according to manufacturer's instructions. Approximately 20 ng of purified fragment was combined with 1 µl pCR2.1-TOPO vector in a total volume of 5 µl. Reactions were incubated at room temperature (20° C.) for 5 min. 2 µl of the reactions was transformed into TOP1OF' competent cells using heat-shock transformation and plated on 2× YT/ampicillin plates supplemented with 10 mM IPTG and 2% (w/v) X-gal for blue-white screening. White colonies after overnight growth were picked from the plates, grown in 5 ml of LB medium supplemented with 100 mg/l ampicillin and plasmid DNA prepared using the Qiaprep Spin Miniprep kit. The presence of an insert of the expected size was confirmed by restriction digestion with EcoRI. The plasmid insert of several positive clones was sequenced and the sequences compared using the Clustal alignment program.

Analysis of Enovin Gene Expression by RT-PCR Analysis.

Oligonucleotide primers PNHsp3 and PNHap1 (see table 1) were used for the specific PCR amplification of a 502 bp fragment from enovin. PCR amplifications were performed on human multiple tissue cDNA (MTC™) panels normalized to the mRNA expression levels of six different housekeeping genes. PCR reactions with enovin specific primers were performed in a total volume of 50 µl, containing 5 µl of cDNA, 1× GC cDNA PCR reaction buffer, 0.2 mM dNTP, 1 M GC-MELT™TM, 400 nM of primers PNHsp3 and PNHap1 and 1 µl of Advantage KlenTaq polymerase mix. Samples were heated to 95° C. for 30 s and cycling was done for 30 s at 95° C. and 30 s at 68° C. for 35 cycles. Samples were analysed on a 1.2% (w/v) agarose gel in 1× TAE buffer (40 mM Tris-acetate, 1 mM EDTA (sodium salt), pH 8.3) and images of the ethidium bromide stained gels were obtained using an Eagle Eye II Video system (Stratagene, La Jolla, Calif., USA).

Similarity searching of the daily update of the EMBL/GenBank database with the human neurturin and persephin protein sequences yielded a genomic DNA sequence coding for a putative novel protein similar to the neurotrophic factors GDNF, NTN and PSP which has been called enovin (EVN). Additional database homology searching using the genomic DNA sequence surrounding the region coding for enovin yielded several expressed sequence tag (EST) clones derived from different human tissues (prostate epithelium [accession no. AA533512 (ID1322952)], lung carcinoma [accession no. AA931637] and parathyroid tumor [accession no. AA844072]). These clones contain DNA sequence outside of the region of homology with GDNF, PSP or NTN, but confirmed that enovin mRNA is expressed in normal and tumor tissues.

Figure 1C:
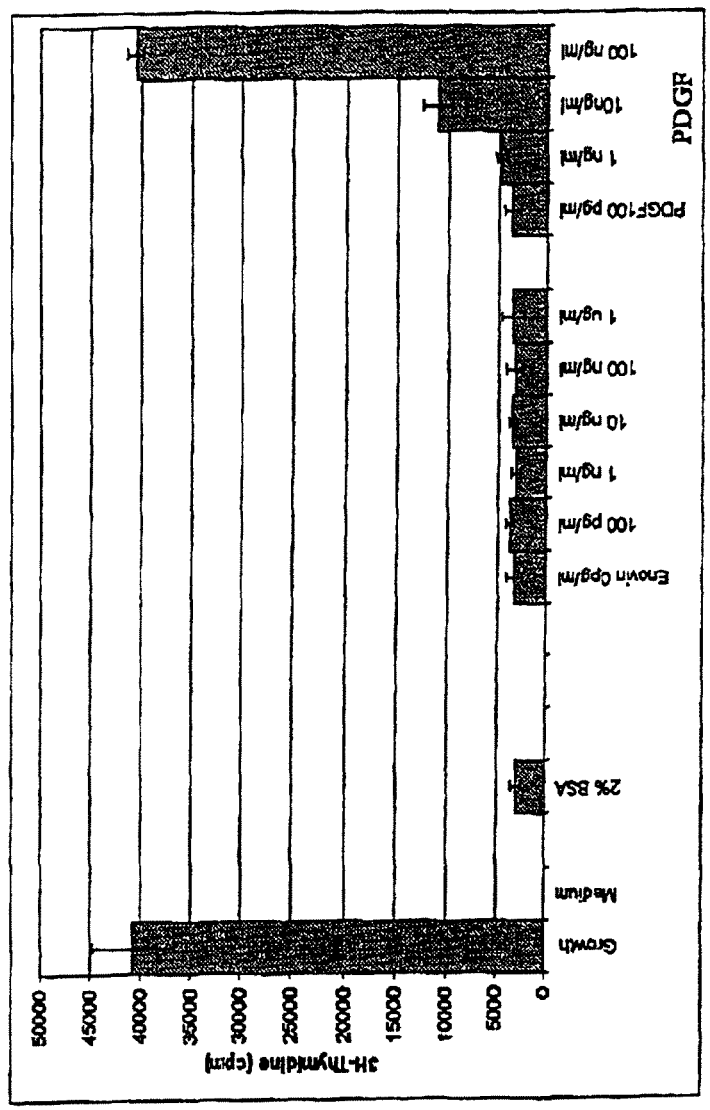
Figure 11:
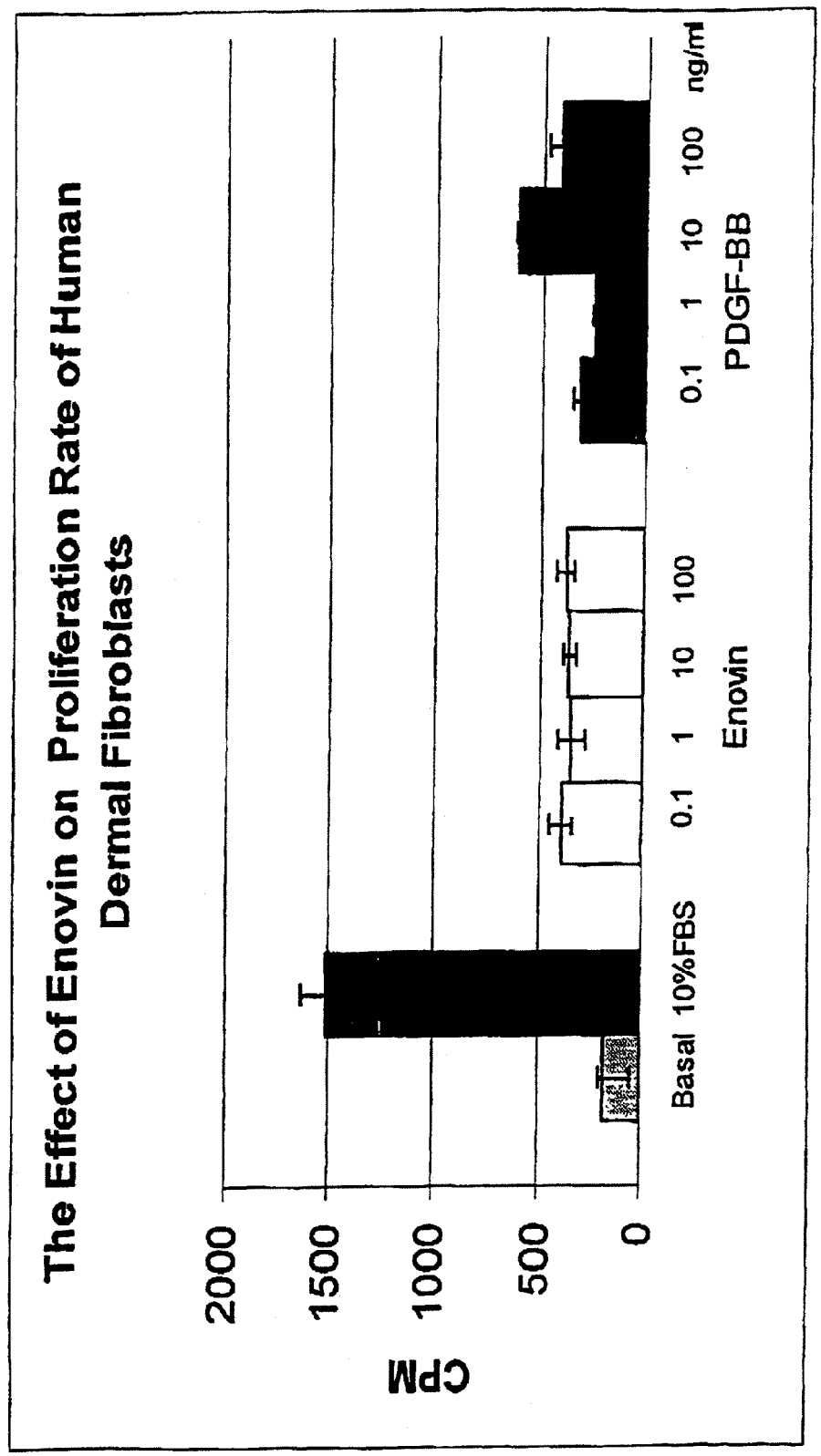
Figure 12:
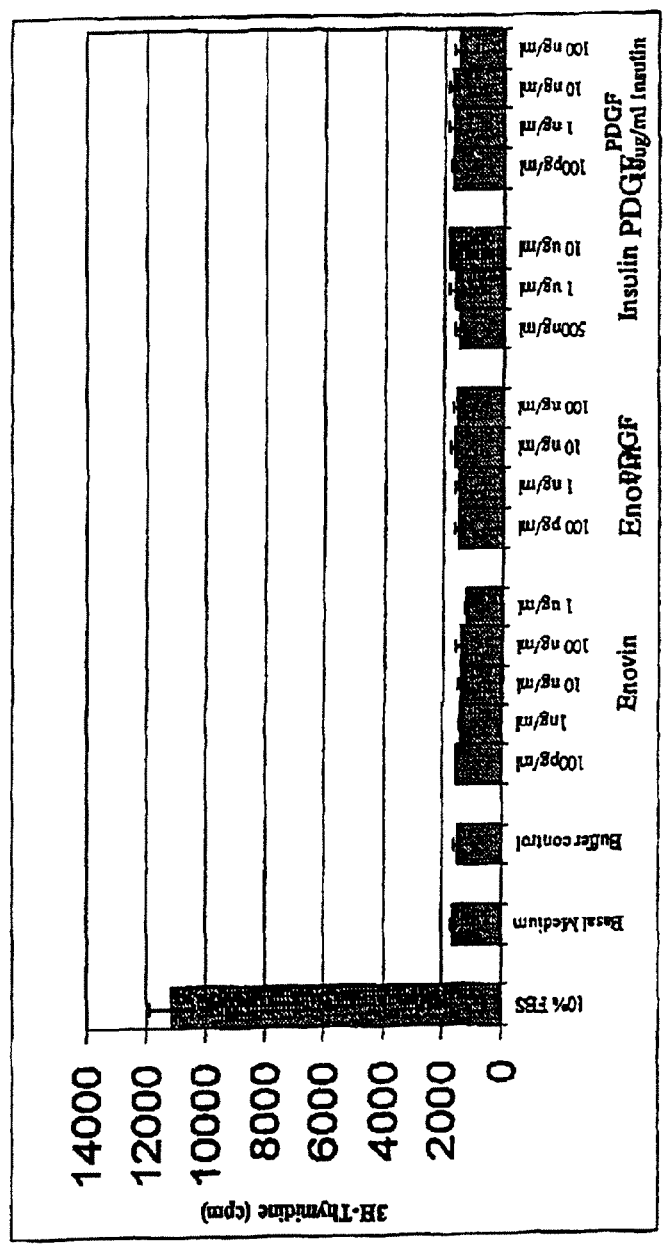
Figure 13:
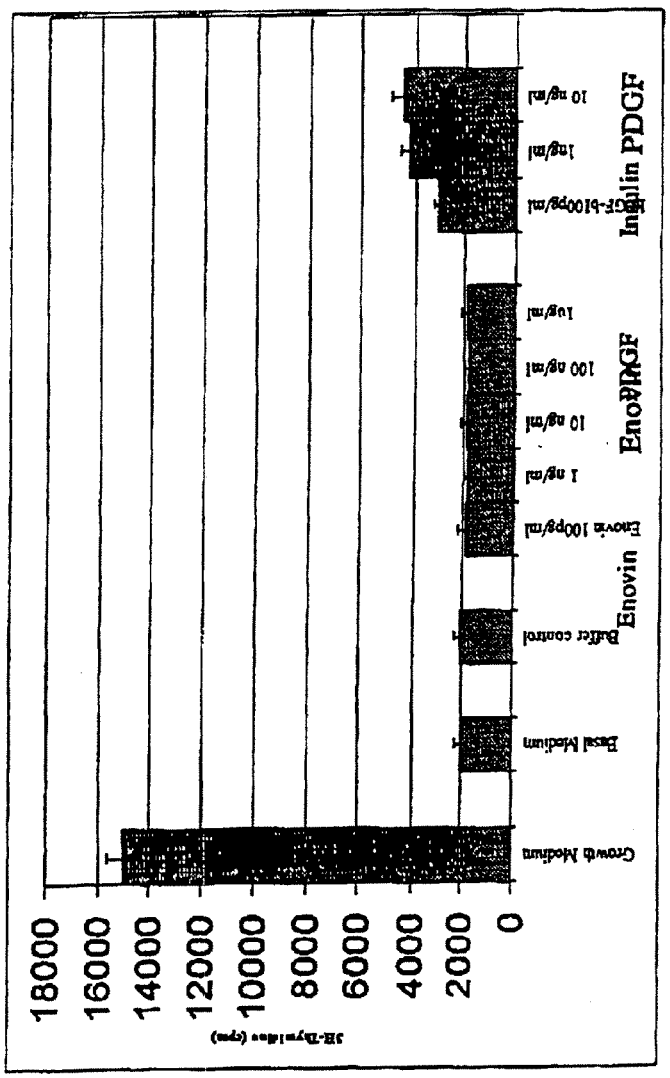
Figure 14:
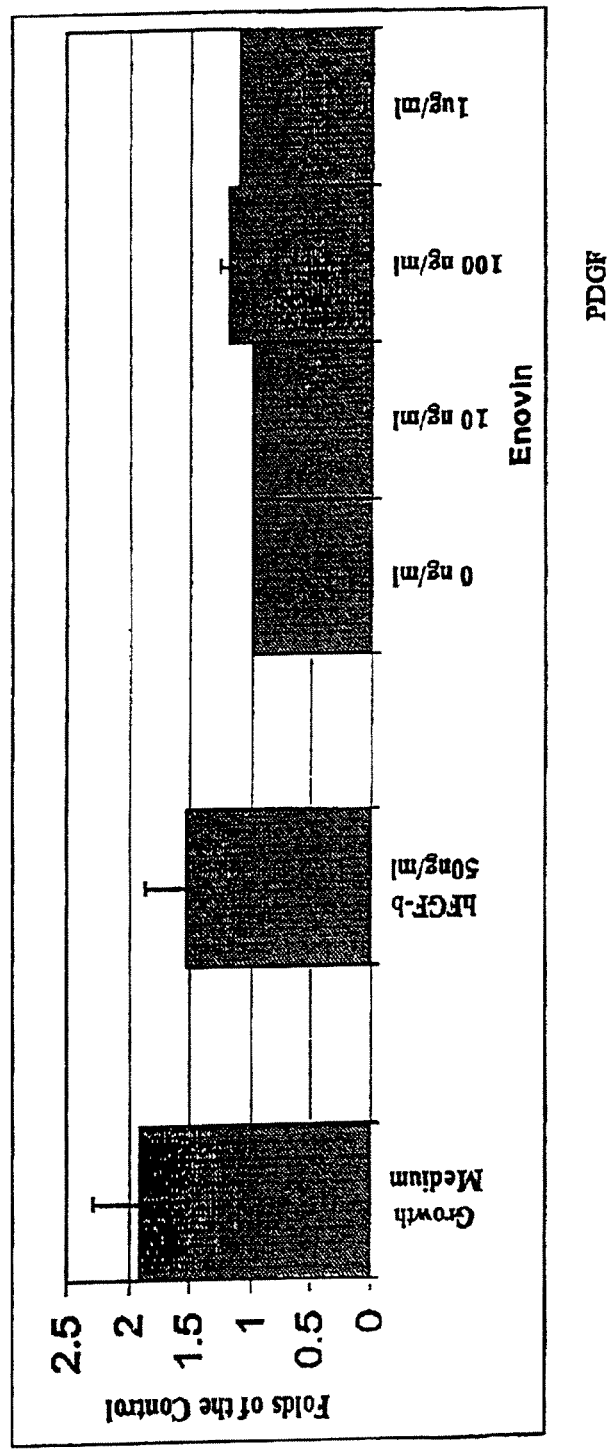
Figure 15:
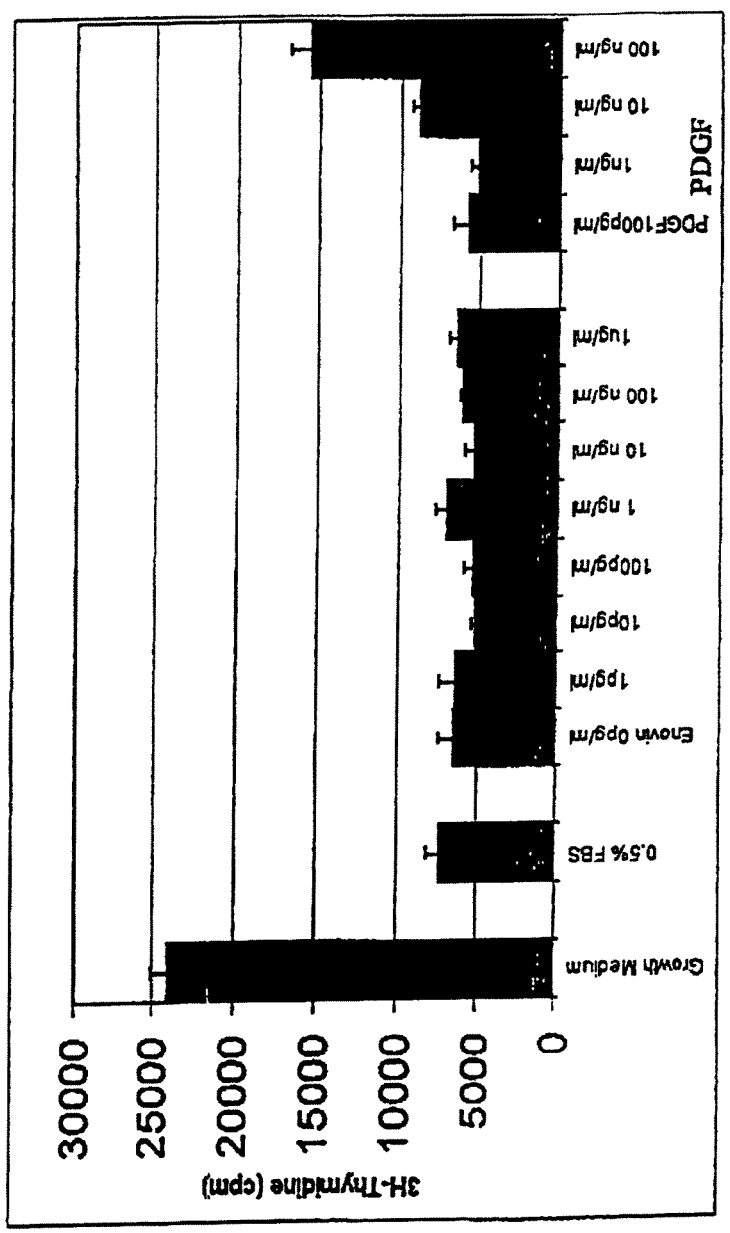
Figure 16:
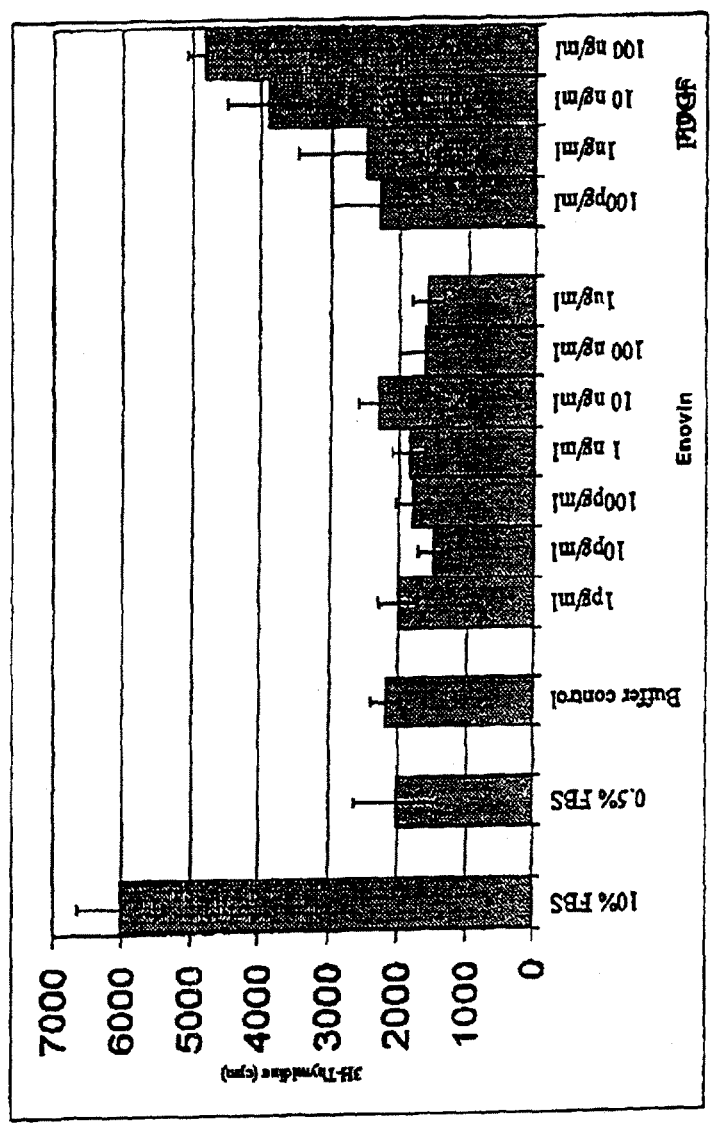
Figure 17:
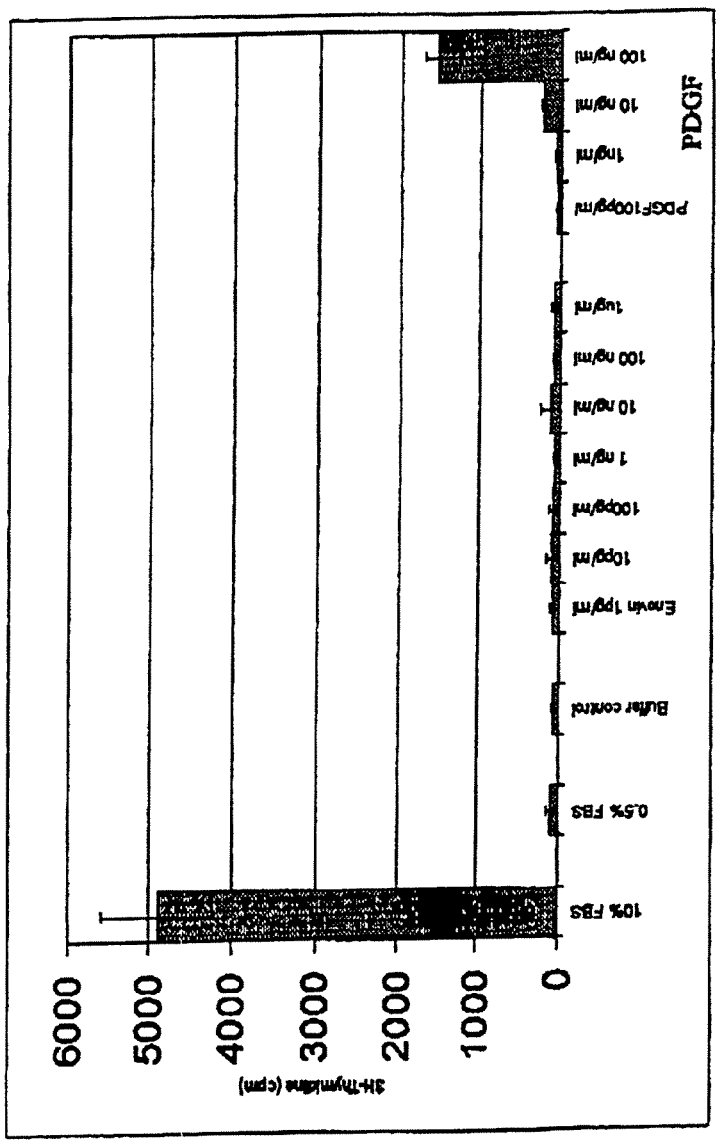
Figure 18:
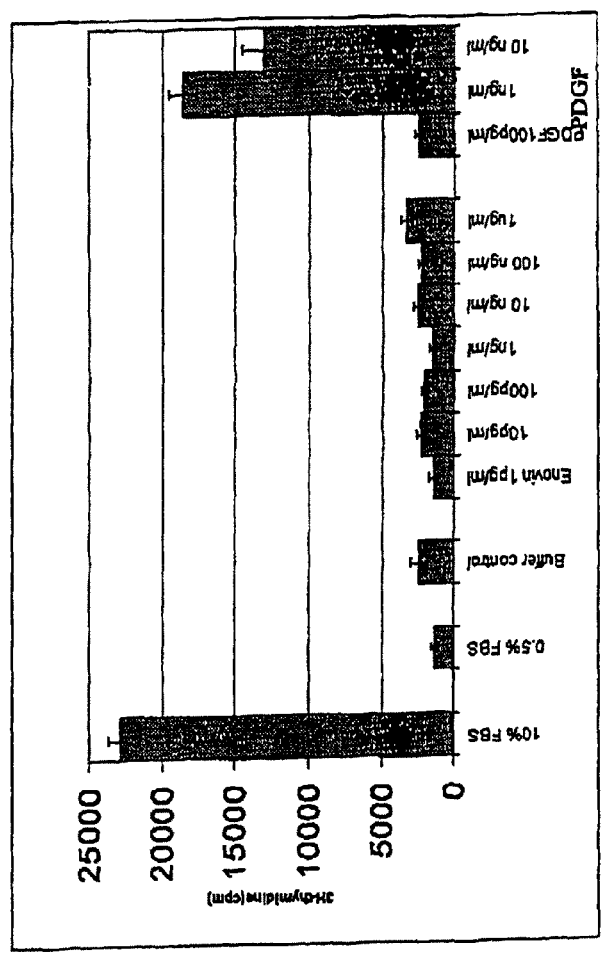

Initial PCR amplification using primers (PNHsp3 and PNHap1) based on the genomic sequence yielded a fragment of ≈500 bp from fetus, fetal brain, prostate, frontal cortex, hippocampus, cerebellum cDNA and from genomic DNA, but not from lung cDNA. Cloning and sequence analysis of these fragments yielded a DNA sequence of 474 bp that translated into a predicted protein sequence of 139 amino acid residues including seven conserved cysteine residues characteristic of all the members of the transforming growth factor β (TGF-β) family of proteins (Kingsley, 1994) (FIG. 1) (SEQ ID NOS. 2 and 4). The sequence also contained a RXXR motif for cleavage of the prodomain (RAAR, amino acid position 23 to 26) (Barr, 1991). A similar cleavage site is present in the GDNF, NTN and PSP protein sequences, at a comparable position in the prodomain sequence. Assuming cleavage of the enovin prodomain occurs at this site in vivo, the mature EVN protein sequence contains 113 amino acid residues (residue 27 to 139 in FIG. 1) (SEQ ID NO. 3) and has a calculated molecular mass of 11965 Da and an isoelectric point of 11.8. There is one potential N-glycosylation site present in the mature sequence (NST at amino acid position 121-123). Moreover, several regions conserved between the mature forms of the known neurotrophic factors GDNF, NTN and PSP were also present in enovin (FIG. 2). Table 2 summarizes the results of the comparison of the mature protein sequences of the GDNF family members by the BESTFIT program. Percentage identity and percentage similarity are shown. The GDNF, NTN, PSP and EVN mature sequences used in this comparison started at the first amino acid residue following the RXXR cleavage site.

TABLE 2

Pairwise comparison of mature human GDNF family members using the BESTFIT program.

| Comparison | % identity | % similarity |
|---|---|---|
| EVN vs GDNF | 38.8 | 47.2 |
| EVN vs NTN | 51 | 56.1 |
| EVN vs PSP | 53.3 | 57.8 |

TABLE 2-continued

Pairwise comparison of mature human GDNF family members using the BESTFIT program.

| Comparison | % identity | % similarity |
|---|---|---|
| GDNF vs NTN | 44.8 | 57.3 |
| GDNF vs. PSP | 44.3 | 50 |
| NTN vs PSP | 50 | 54.4 |

From these comparisons it is apparent that the mature enovin protein is more closely related to persephin and to neurturin than to GDNF.

Amplification, cloning and sequence analysis of a larger fragment of the enovin DNA sequence from frontal cortex cDNA using primers based on the genomic EMBL/GenBank sequence (acc. no. AC005038) yielded a sequence of 819 bp (FIG. 3) (SEQ ID NO. 5). This sequence contains a putative ATG start codon at nucleotide positions 30-32 and yields an open reading frame (reading frame A in FIG. 3) (SEQ ID NO. 6) that extends up to a stop codon at nucleotide positions 285-287. The translated protein sequence of this region does not show similarity to any known protein in the databases. Translation of the cDNA sequence in the second reading frame (reading frame B in FIG. 3) (SEQ ID NO. 7) yields a predicted protein sequence of 159 amino acid residues. This sequence contains the RXXR cleavage site (position B43 to B46; nucleotide position 460-471) and the sequence corresponding to the mature enovin sequence (position B47 to B159; nucleotide position 472-810). The open reading frame including the RXXR cleavage site and the mature enovin coding sequence extends from nucleotide position 334 (preceded-by an in-frame stop codon) to a stop codon at position 811-813, but does not contain an ATG codon for a starting methionine residue. In analogy with persephin (Milbrandt et al., 1998) we hypothesize that an unspliced intron is present in the majority of the mRNA transcripts from the EVN gene. GDNF and NTN also have an intron in their respective pro-domain coding regions (Matsushita et al., 1997, Heuckeroth et al., 1997).

Figure 22:
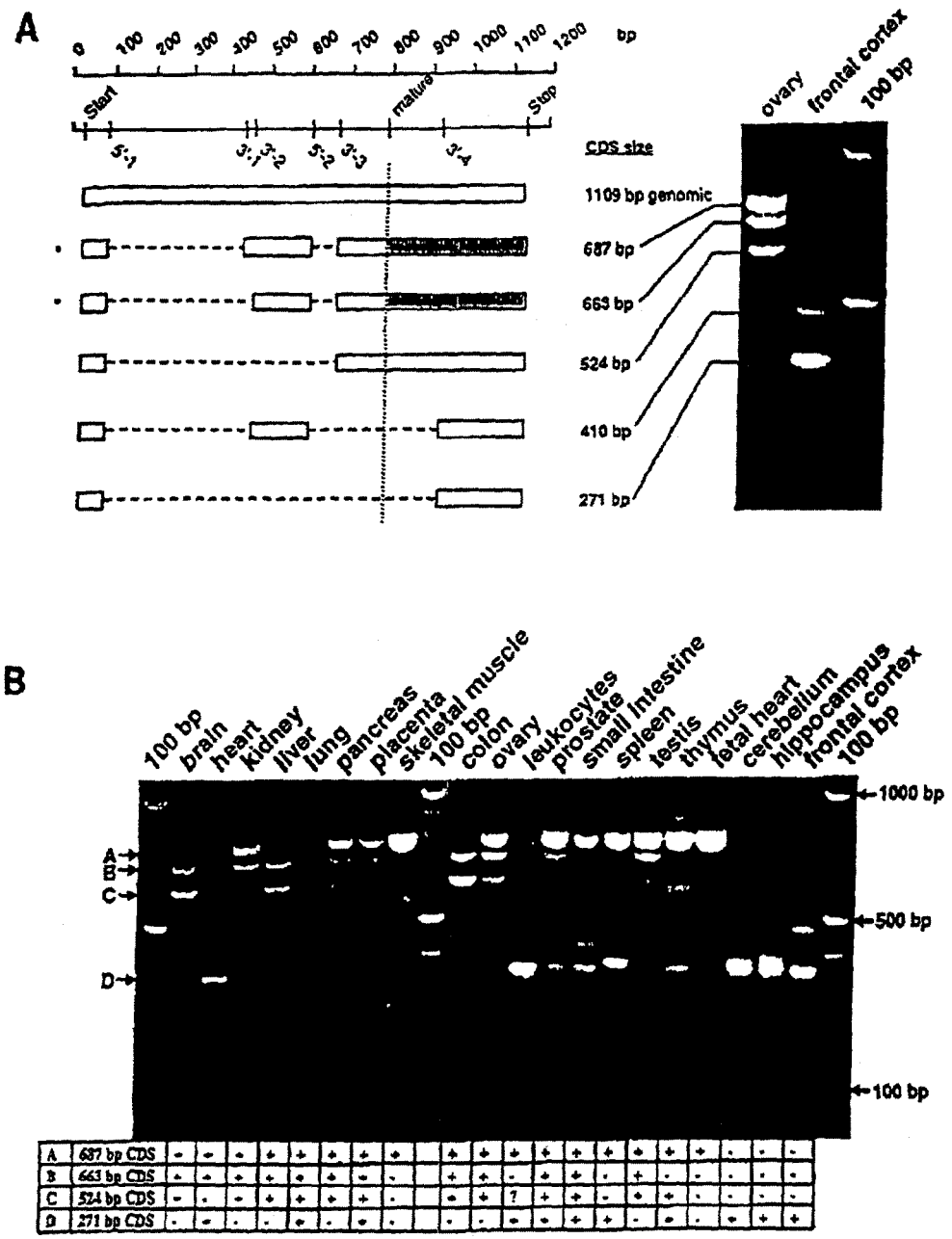

To evaluate the existence of different mRNA transcripts for Enovin, RT-PCR experiments were performed using primers situated at the 5' end of the Enovin coding sequence just 5' of a possible upstream ATG start codon (primer PNHsp5 [5'-GCA AGC TGC CTC AAC AGG AGG G-3' (SEQ ID NO: 37)] and nested primer PNH [5'-GGT GGG GGA ACA GCT CAA CAA TGG-3' (SEQ ID NO: 38)] and at the 3' end (primer PNHap1 and nested primer PNHap2 [see Table 1]. Experiments were performed on human multiple tissue cDNA panels (Clontech MTC panels I and II), on a fetal heart cDNA library (Clontech) and on cDNA derived from human cerebellum, hippocampus or frontal cortex (Masure et al., 1998). Primary PCR reactions were performed with primers PNHsp5 and PNHap1 under GC-rich conditions (Advantage GC-PCR kit, Clontech) for 30 cycles (95° C.-30s, 60° C.-30s, 72° C.-1 min) as described. Nested PCR reactions were performed on 1 µl of the primary PCR product using primers PNHsp6 and PNHap2 under the same conditions for 30 cycles. Resulting PCR products were analysed on a 1.5% agarose gel and ranged in size from ±350 bp to ±800 bp. Several bands were purified from the gel and the PCR fragments sequenced directly. Some purified PCR products were also cloned in vector pCR2.1-TOPO (TOPO-TA cloning kit, Invitrogen) and then sequenced. Sequence analysis confirmed the existence of different mRNA molecules containing Enovin sequence. The obtained fragment sequences were compared with the genomic Enovin sequence. This allowed us to identify several possible 5' and 3' splice sites in the genomic sequence (FIG. 21) (SEQ ID NOS. 11 through 15). All these splice sites corresponded to the consensus sequences for donor and acceptor splice sites (Senaphthy, P., Shapiro, M. B. & Harris, N. L. (1990)) splice junctions, branch point sites, and exons: sequence statistics, identification, and applications to genome project. Methods Enzymol. 183, 252-278). The different Enovin splice variants identified and their presence in different human tissues are summarized in FIG. 22. Only two of the 5 sequenced transcripts yield functional Enovin protein upon translation from the ATG start codon. These two transcripts code for proteins of 228 or 220 amino acids, respectively with predicted signal peptides of 47 and 39 amino acid residues. The predicted protein sequences of these two variants are shown in FIG. 23 (long variant) (SEQ ID NO: 9) and FIG. 24 (short variant) (SEQ ID NO: 10). The long variant can be deduced from the DNA sequence of FIG. 21 (SEQ ID NO: 8) by splicing out the first intron at locations 5'-1 and 3'-1 and the second intron at 5'-2 and 3'-3 (SEQ ID NO: 12). Upon translation of the open reading frame, the predicted protein sequence of FIG. 23 is obtained. The shorter variant can be deduced from the DNA sequence of FIG. 21 by splicing out the first intron at locations 5'-1 and 3'-2 and the second intron at 5'-2 and 3'-3. Upon translation of the open reading frame, the predicted protein sequence of FIG. 24 is obtained.

The longest transcript seems to be the most abundant in most tissues as judged by the band intensity in FIG. 22B. The shorter transcripts result in frame shifts yielding a translated protein missing the mature Enovin amino acid sequence homologous with GDNF, NTN and PSP. The two smallest transcripts even miss part of the mature coding sequence, including two of the seven highly conserved cysteine residues. FIG. 22B shows the distribution of the main splice variants in different human tissues. Functional Enovin mRNA is expressed in almost all tissues tested, including brain, heart, kidney, liver, lung, pancreas, skeletal muscle, colon, small intestine, peripheral blood leukocytes, spleen, thymus, prostate, testis, ovary, placenta and fetal heart. In some human tissues (e.g. cerebellum, hippocampus), only non-functional transcripts could be amplified by PCR. To our knowledge, the occurrence of non-functional mRNA transcripts to such an extent has not been described before. The biological significance of this finding remains to be studied. Although the expression of NTN and PSP in different tissues has not been fully characterized, their expression levels seem much lower and the expression more restricted to certain tissues (Kotzbauer et al., 1996, Milbrandt et al., 1998).

Recombinant Expression of Enovin in *E. coli* Construction of an Enovin Expression Plasmid A 414 bp PCR fragment was amplified from human genomic DNA with primers PNHsp4 and PNHap2 (Table 1) and cloned in vector pCR2.1-TOPO using TA-cloning (Invitrogen). The sequence of the insert was confirmed by sequence analysis. One clone containing an insert with the Enovin consensus sequence (clone 36) was used for subsequent construction of an expression plasmid. Two primers were designed containing appropriate restriction sites at their 5' ends. Forward primer PNHexp-sp1 (5'-GCG GAT CCG GCT GGG GGC CCG GGC A-3' (SEQ ID NO: 39)) contained a Bam-HI restriction site (in bold, italics) and reverse primer PNHexp-ap1 (5'-GCC TCG AGT CAG CCC AGG CAG CCG CAG G-3' (SEQ ID NO: 40)) contained a XhoI restriction site (also in bold, italics). Using these primers, the 343 bp fragment coding for mature Enovin (position 81 to 422 in FIG. 1) was amplified from clone 36. The PCR reaction was performed in a total volume of 50 µl, containing 1× GC cDNA PCR reaction buffer, 0.2 mM dNTP, 1 M GC-MELT™ (200 nM of primers PNHexp-sp1 and PNHexp-ap1, 1 µl of Advantage KlenTaq polymerase mix and 10 ng of plasmid DNA from clone 36. Samples were heated to 94° C. for 5 min and cycling was done for 45 s at 94° C., 1 min at 58° C. and 30 s at 72° C. for 25 cycles with a final step of 7 min at 72° C. The resulting 50 µl product was purified using the Qiaquick PCR purification kit (Qiagen) and the DNA eluted in 30 µl. 25 µl of this purified product was then digested in a 30 µl reaction with 10 U of BamHI and 10 U of XhoI in 1× buffer B (Boehringer Mannheim) for 1 h at 37° C. After electrophoresis in a 1% (w/v) agarose gel in 1× TAE buffer (40 mM Tris-*acetate, 1 mM EDTA (sodium salt), pH 8.3), the expected 353 bp band was excised from the gel and purified using the Qiaquick gel extraction kit. The resulting fragment was ligated in the vector pRSET B (Invitrogen) linearised with BamHI and XhoI. The insert of the resulting plasmid construct (hEVNmat/pRSETB) was confirmed by complete sequence analysis. The resulting construct codes for a 146 amino acid protein with a predicted molecular mass of 15704 Da including an NH2-terminal 6× His-tag fused in frame to the mature Enovin coding sequence. The NH2-terminal amino acid sequence of the resulting protein is thus MRGSHHHHHHGMASMTG-GQQMGRDLYDDDDKDPAGGPGS (SEQ ID NO: 41) (mature Enovin sequence in bold, 6× His tag in bold, italics).

Expression of Enovin in BL21 (DE3) *E. coli* Cells

Recombinant production of Enovin protein was performed essentially as described for Neurturin by Creedon at al. (1997), with modifications. For the production of recombinant Enovin protein, the plasmid hEVNmat/pRSETB was transformed in *E. coli* strain BL21 (DE3) (Novagen) and grown in 2× YT/ampicillin-medium (16 µl of tryptone, 10 µl of yeast extract, 5 µl of NaCl and 100 mg/l of ampicillin) at 30° C. (225 rpm) or 37° C. (300 rpm) to an OD600 of approximately 0.5 prior to addition of IPTG to a final concentration of 0.2 mM to induce expression. Cell pellets were harvested by centrifugation following a 3 h induction period, washed with phosphate-buffered saline, centrifuged and stored frozen. For purification and refolding, cell pellets were resuspended in sonication buffer (20 mM Tris-HC1, pH 8.0, 300 mM NaC1, 1 mM 2-mercaptoethanol protease inhibitors (Complete™ protease inhibitor cocktail tablets (Boebringer Mannheim, 1 tablet per 50 ml buffer) and 1 mg lysozyine per 500 mg cell pellet). Cells were disrupted by sonication and inclusion bodies harvested by centrifugation. Inclusion bodies were dissolved and incubated in buffer A (8 M urea, 20 mM Tris-HC 1 pH 7.6, 200 mM NaC1, 1 mM 2-mercaptoethanol) for 30 min at 37° C. prior to adding to Ni-NTA resin (nickel nitrilotriacetic acid, Qiagen). After 40 min shaking at 37° C., samples were washed once with buffer A and loaded onto a 5 ml Ni-NTA column. The column was washed successively with 10 column volumes of buffer A, 10 column volumes of buffer A at pH 7.2 and 10 column volumes of buffer A at pH 7.2+10 mM imidazole. The Enovin was eluted from the column in 4 column volumes of buffer A at pH 7.2+200 mM imidazole.

Enovin refolding was performed by stepwise overnight dialysis at 4° C. in renaturation buffer (0.1 M sodium phosphate, 0.15 MaCl, 3 cysteine, 0.02% Tween-20, 10% glycerol, 0.01 M Tris-RC1, pH 8.3) containing decreasing amounts of urea at each step (GM to 4M to 3M to 2M to iN to 0.5M to ON urea). The purified protein was aliquotted, stored at −20° C. and further used for functional assays.

Chromosomal Localization of the Enovin Gene.

A 3.3 kb Fragment of the Enovin Gene was Amplified from Cerebellum cDNA Using Primers EVN(7)-sp1 (5'-TTC GCG TGT CTA CAA ACT CAA CTC CC-3' (SEQ ID NO: 42)) and PNHap1 (5"-GCA GGA AGA GCC ACC GGT AAG G-3' (SEQ ID NO: 43)) designed on the sequence of EMBL accession number AC005038. The PCR reaction was performed in a total volume of 50 µl, containing 1× Expand Long Template PCR reaction buffer (Boehringer Mannheim), 0.5 mM dNTP, 1 M GC-MELT ((Clontech Laboratories), 400 nM of primers EVN(7)-sp1 and PNHap1 and 1 µl of cerebellum cDNA. After an initial 2 min at 94° C., 0.75 µl. of Expand Long Template polymerase (Boehringer Mannheim) was added and cycling was done for 10 s at 94° C., 30 s at 58° C. and 3 min at 68° C. for 10 cycles. Then, additional cycles were performed increasing the extension time at 68° C. with 20 s every cycle. A final 7 min at 68° C. were also included. The resulting 3.3 kb fragment was purified after electrophoresis in a 0.8% agarose/TAE gel and cloned in vector pCR2.1-TOPO using TA-cloning (Invitrogen). Complete sequence analysis of the 3.3 kb insert of one clone confirmed that the obtained cDNA sequence corresponded to the genomic sequence in the EMBL database (accession number AC00503). No introns were spliced out in the cDNA obtained from cerebellum cDNA.

Figure 4A:
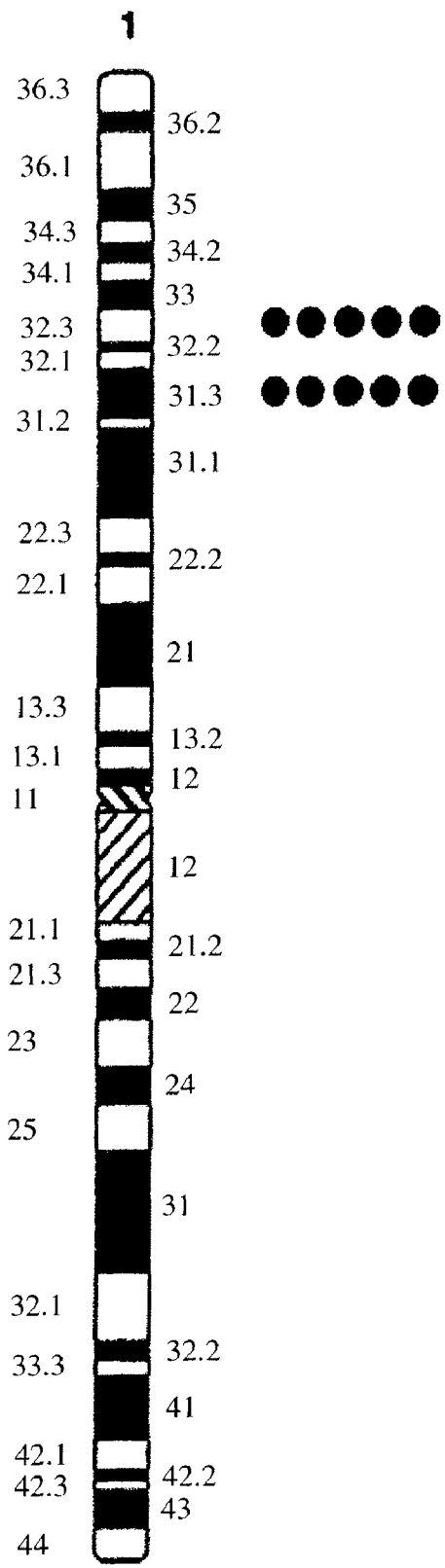
Figure 4B:
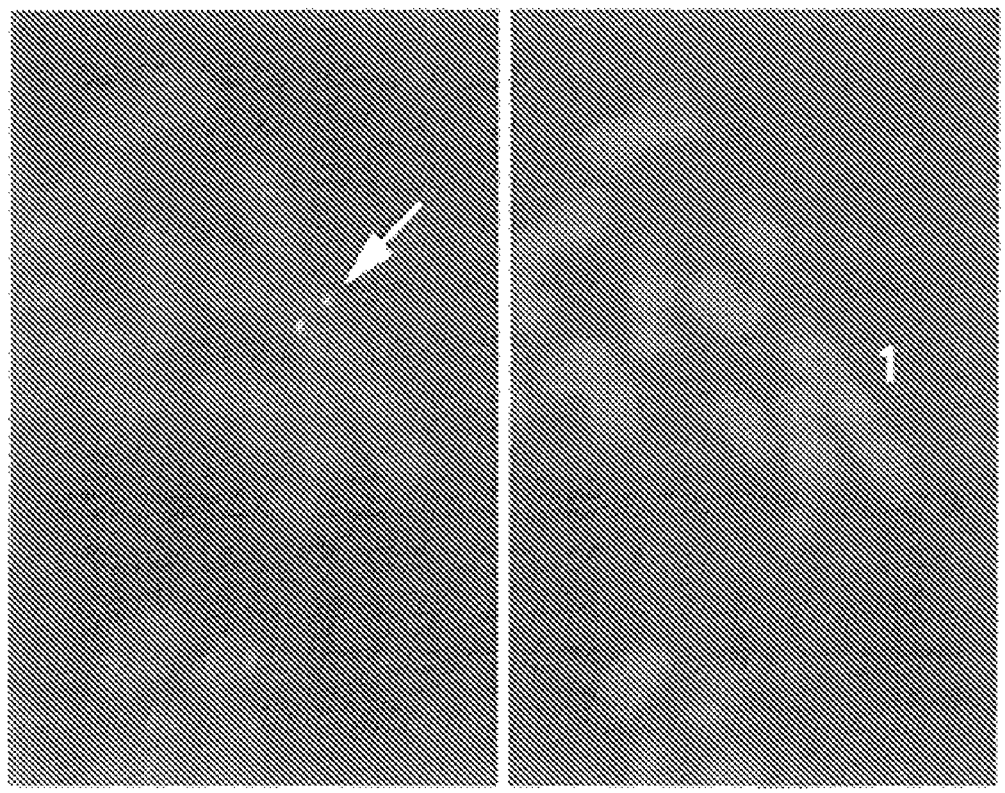

Chromosomal mapping studies were carried out using fluorescent in situ hybridization (FISH) analysis essentially as described (Heng et al., 1992, Heng & Tsui, 1993). Human lymphocytes were cultured at 37° C. for 68-72 h before treatment with 0.18 mg/ml 5-bromo-2'-deoxyuridine (BrdU) to synchronize the cell cycles in the cell population. The synchronized cells were washed and recultured at 37° C. for 6 h. Cells were harvested and slides were prepared using standard procedures including hypotonic treatment, fixation and airdrying. The 3.3 kb probe for Enovin was biotinylated and used for FISH detection. Slides were baked at 55° C. for 1 h, treated with RNase and denatured in 70% formamide in 2× NaC1/Cit (20× NaC1/Cit being 3 M NaC1, 0.3 M disodium citrate, pH 7.0) for 2 min at 70° C. followed by dehydration with ethanol. The probe was denatured prior to loading on the denatured chromosomal slides. After overnight hybridization, slides were washed and FISH signals and the 4',6-diamidino-2-phenylindole banding pattern were recorded separately on photographic film, and the assignment of the FISH mapping data with chromosomal bands was achieved by superimposition of FISH signals with 4',6-diamidino-2-phenylindole banded chromosomes (Heng & Tsui, 1993). Under the conditions used, the hybridization efficiency was approximately 72% for this probe (among 100 checked mitotic figures, 72 of them showed signals on one pair of the chromosomes). Since the 4',6-diamidino-2-phenylindole banding was used to identify the specific chromosome, the assignment between the signal from the probe and the short arm of chromosome 1 was obtained. The detailed position was further determined based upon the summary from 10 photographs (FIG. 4A). There was no additional locus picked by FISH detection under the conditions used, therefore, we conclude that Enovin is located at human chromosome 1, region p31.3-p32. An example of the mapping results is presented in FIG. 43.

From the gene map data at the National Center for Biotechnology Information (NCBI, http://www.ncbi.nlm.nih.gov/genemap), it can be deduced that the genomic clone containing the Enovin sequence (EMBL accession number AC005038) is located on chromosome 1, between markers D1S2843 and D1S417. This corresponds to chromosome 1, region p31.1 to p32.3, confirming the data obtained by FISH analysis.

Tissue Distribution of Enovin as Determined by Northern Blot and Dot Blot Analysis.

Northern blots containing 2 µg of poly(A)-rich RNA derived from different human tissues (Cloritech Laboratories, Palo Alto, Calif., USA; MTN™ blot, MTN™ blot II and Fetal MTN™ blot II) were hybridised according to the manufacturer's instructions with a ($\alpha$-$^{32}$P-dCTP random-priming labelled (HighPrime kit, Boehringer Mannhein) 897 bp Enovin fragment. This fragment was obtained by PCR amplification with primers PNHsp1 and PNHap 1 on frontal cortex cDNA and subsequent cloning in vector pCR2.1-TOPO. The fragment contains 897 bp of Enovin sequence up to the stop codon and includes the complete coding sequence for the mature Enovin protein.

Figure 5:
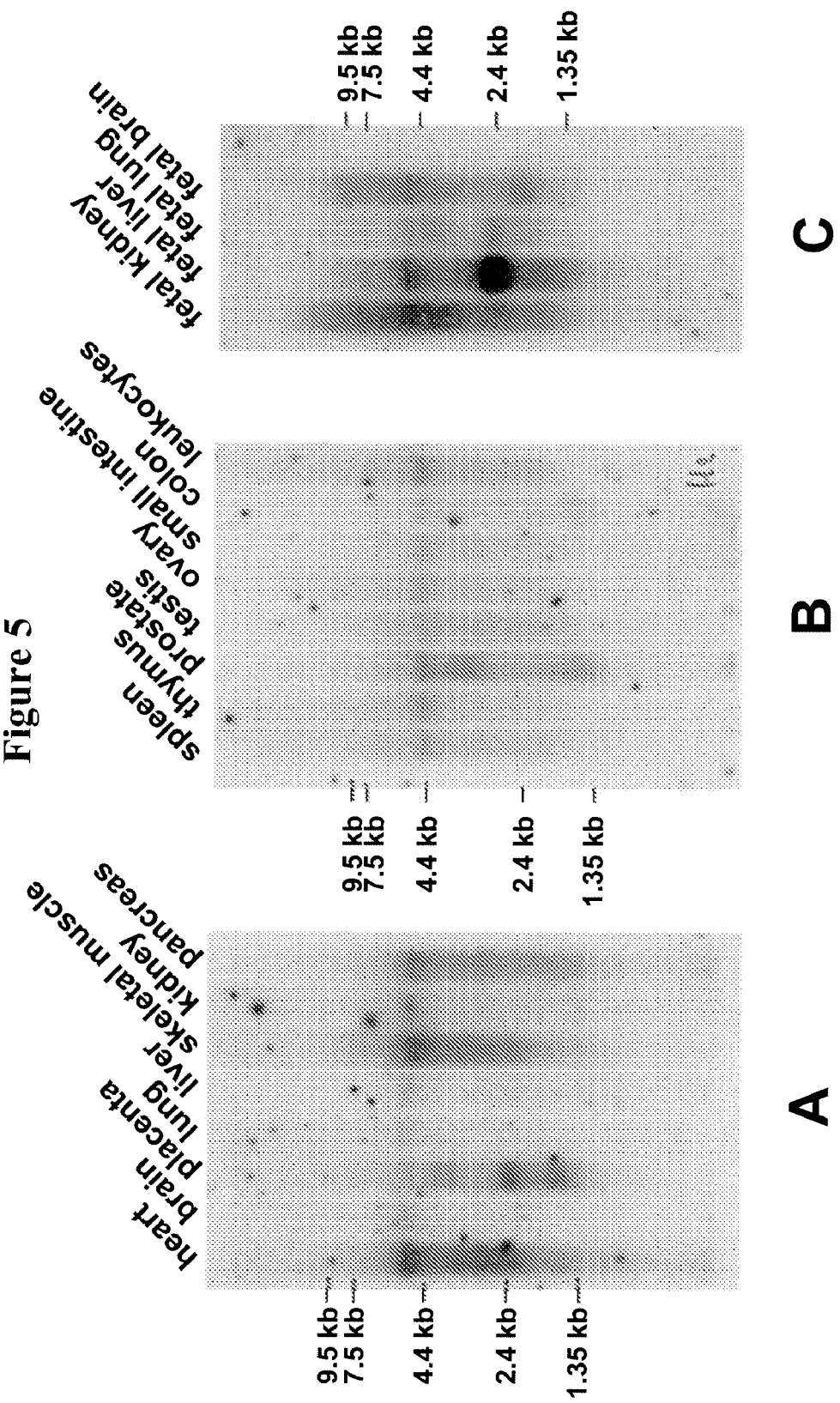
Figure 6:
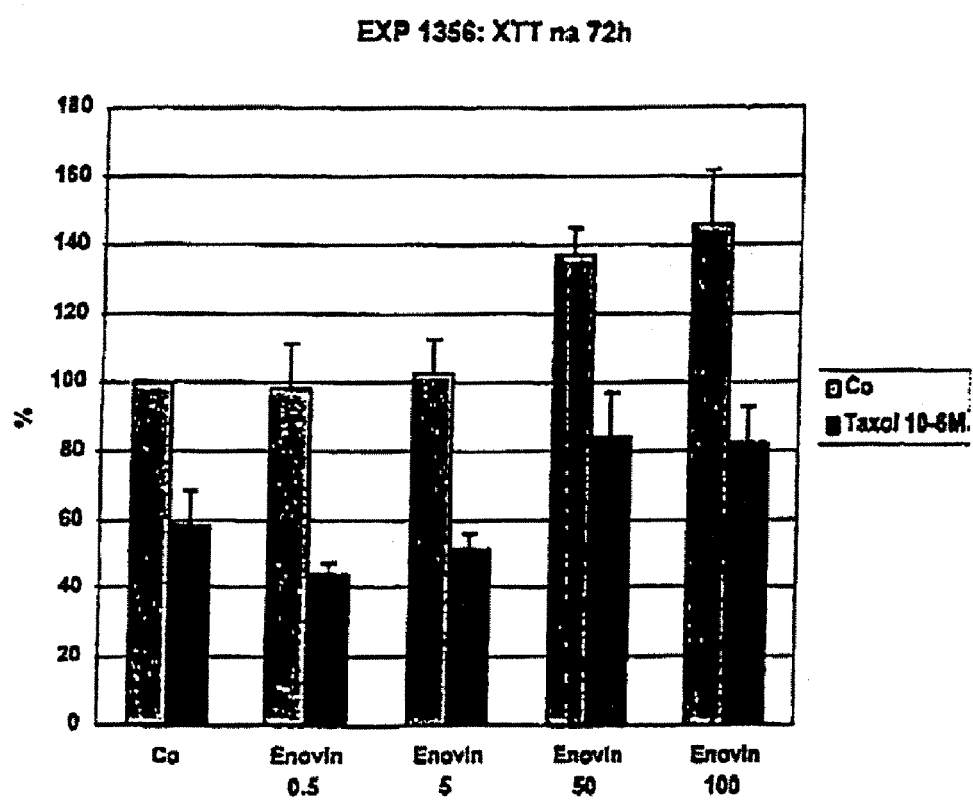
Figure 7:
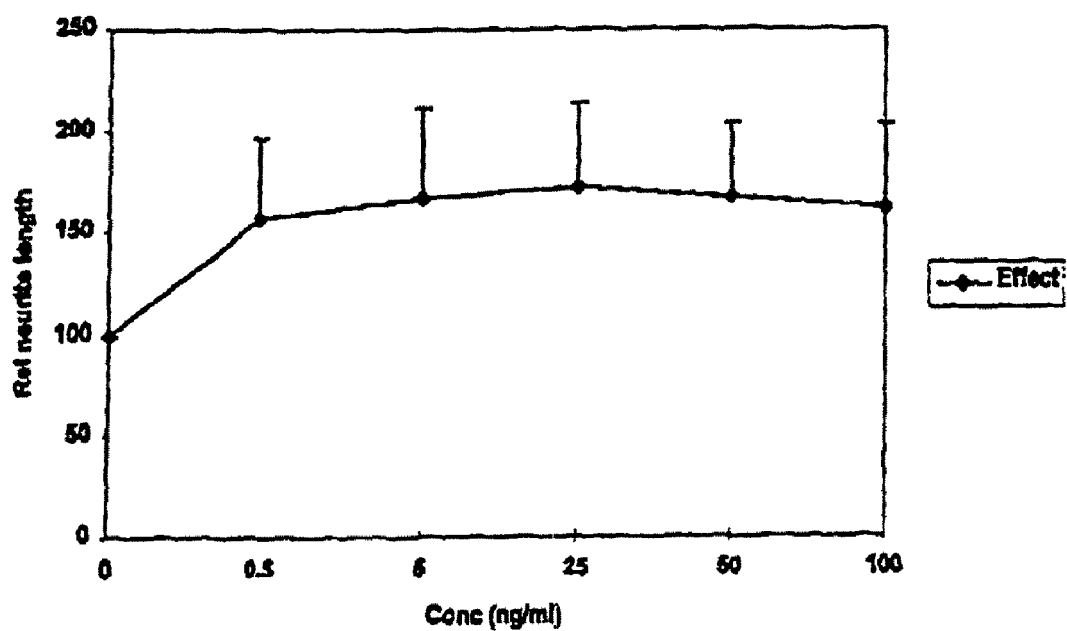
Figure 8:
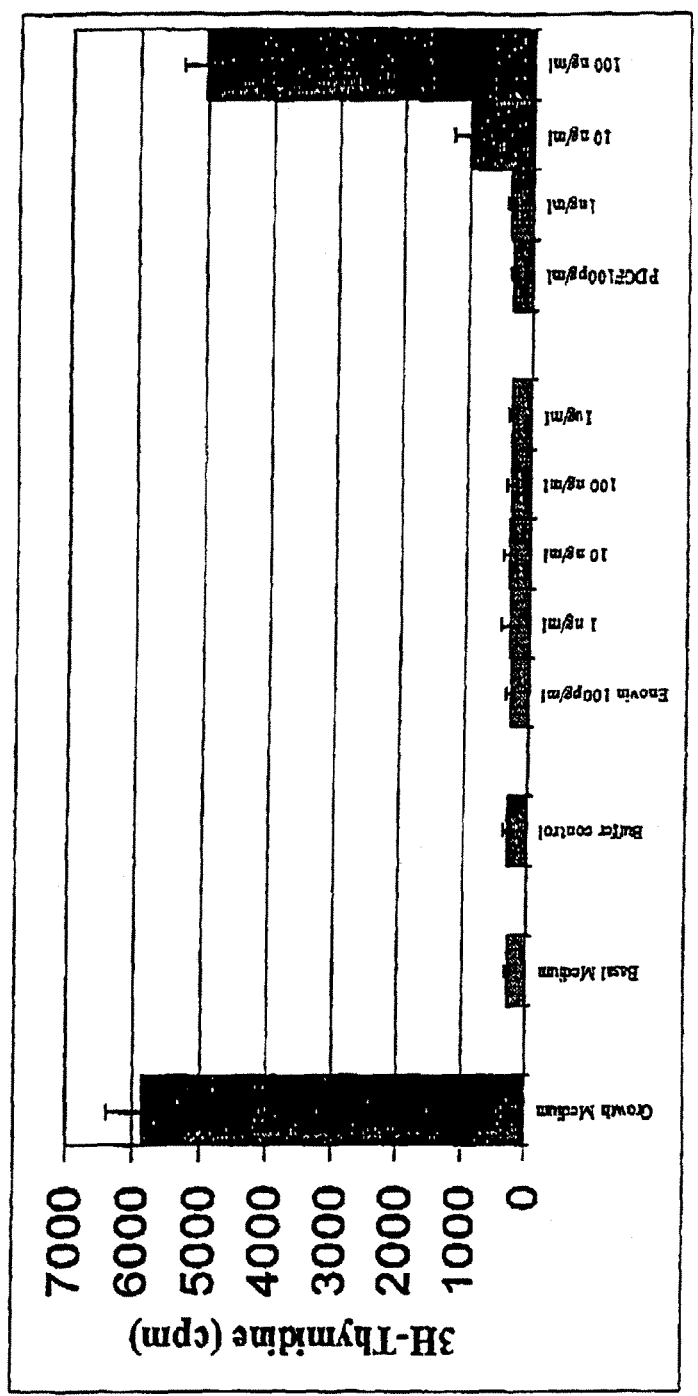
Figure 9:
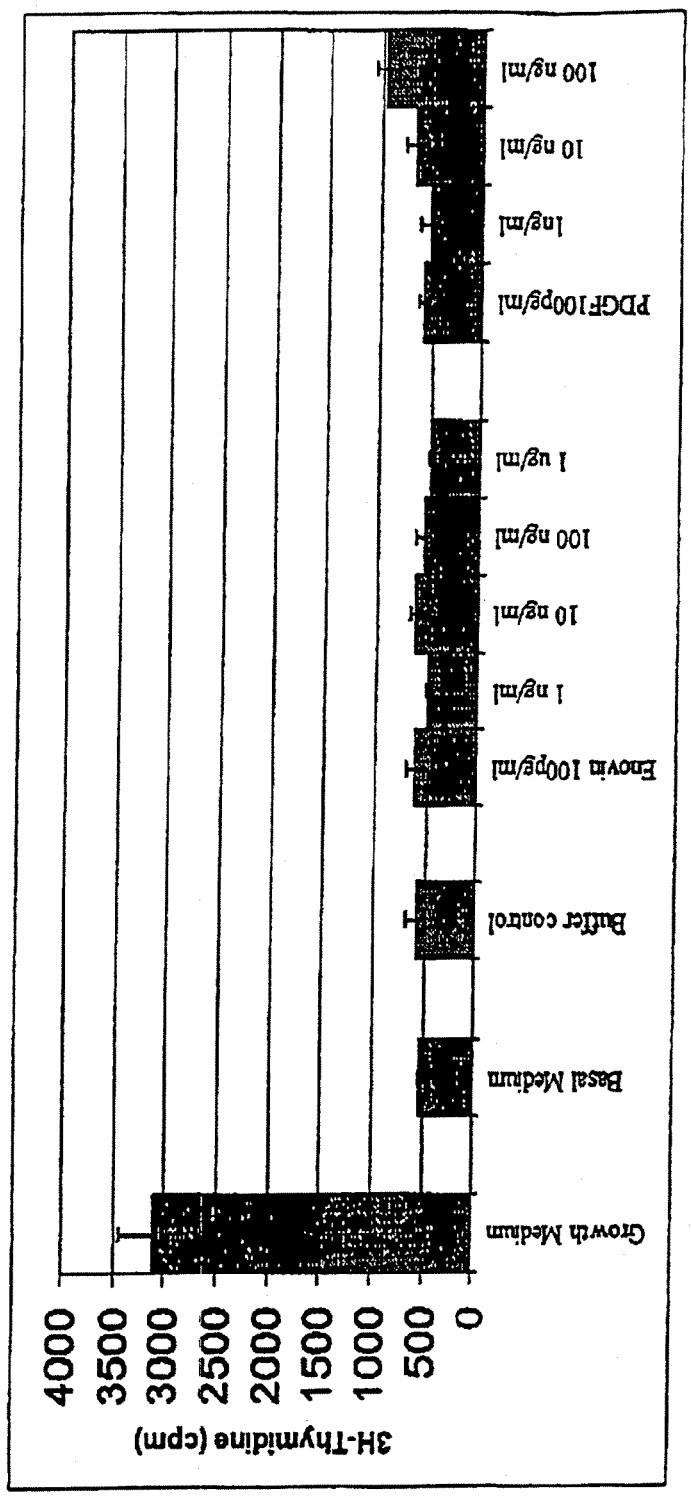

Enovin mRNA was detected as a main transcript of approximately 4.5 kb (FIG. 5A-C). Enovin mRNA was expressed in a range of tissues, most prominently in heart, skeletal muscle, pancreas and prostate. Some smaller-sized transcripts are present in e.g. placenta (4 kb, 2.4 kb and 1.6 kb) and prostate (4 kb and 1.6 kb). In fetal tissue, a prominent 2.4 kb transcript is present in liver and to a lesser extent lung. Other transcripts are also present in fetal kidney, liver, lung and brain.

In addition an RNA master blot (Clontech Laboratories) containing poly(A) rich RNA from different human tissues and developmental stages was also hybridized with the 897 bp Enovin probe. The poly(A) rich RNA samples used for making this blot have been normalized to the mRNA expression levels of eight different housekeeping genes by the manufacturer. Enovin mRNA was expressed ubiquitously, but highest mRNA levels were apparent in prostate, pituitary gland, trachea, placenta, fetal lung, pancreas and kidney (FIG. 5D+E).

Construction of GFR$\alpha$-IgG-Fc Fusions Vectors cDNA regions of GFR$\alpha$-1, GFR$\alpha$-2 and GFR$\alpha$-3 (coding for amino acids 27 to 427, 20 to 431 and 28 to 371, respectively) excluding the sequences coding for the signal peptide and for the COOH-terminal hydrophobic region involved in GPI-anchoring were cloned in-frame in the expression vector Signal pIg plus (R&D Systems Europe Ltd). The resulting proteins expressed from these constructs contain a 17 amino acid NH$_2$-terminal CD33 signal peptide, the GFR$\alpha$ protein region and a 243 amino acid COOH-terminal human IgG$_1$-Fc fusion domain. CHO cells were transfected with GFR$\alpha$ fusion constructs and stably transfected cells were selected using 500 µg G418. Permanent clones were selected using anti Fc antibody. For purification of GFR$\alpha$ fusion proteins, cells were grown in serum-free medium and medium was collected after every 3 days. Medium was centrifuged and applied to a protein A column (Protein A Sepharose, Pharmacia Biotech). Bound protein was eluted with 0.1 M Na citrate, pH 3.0 and collected into 1 M Tris buffer, pH 8.4. Protein concentration was estimated by absorbance at 280 nm using an extinction coefficient of 1.5. These purified soluble GFR$\alpha$-1 to -3 Fc fusion proteins were used for subsequent binding studies.

Surface Plasmon Resonance Analysis

Surface plasmon resonance (SPR) experiments were performed at 25° C. using a BIAcore 3000 instrument. Analyses were performed with enovin and NGF as immobilized ligands. The carboxylated matrix of a F1 sensor chip was first activated with a 1:1 mixture of 400 mM N-ethyl-N-(dimethylaminopropyl)-carbodiimide and 100 mM N-hydroxy-succinimide for 10 min. Than, recombinant enovin and NGF were applied onto the activated surface in 10 nM acetate buffer, pH 4.5 at a flow rate of 5 µl/min. Unoccupied reactive groups were inactivated with 1 M ethanolamine hydrochloride. For binding experiments, soluble GFRα1-3-Fc were superfused at concentrations of 10-100 nM in HEPES buffered saline (150 mM NaC1, 3.5 mM EDTA, 0.05% P-20, 10 mM HEPES, pH 7.4) at a flow rate of 10 µl/min. The association was monitored for 3 min and dissociation for 1 min followed by regeneration with 5 mM NaOH. Dissociation was initiated by superfusion with HEPES buffered saline. A BIAcore evaluation software, 3.0 was used to calculate the association rate ($k_a$), dissociation rate ($k_d$) and the equilibrium dissociation constants ($K_D$ calculated as $k_d/k_a$).

Results

SPR was used to measure binding of soluble GFRα1-3 to immobilized enovin. Specific binding to enovin could be detected with the soluble GFRα3 only. GFRα1 and GFRα2 did not bind to the immobilized enovin. The observed binding of GFRα3 was specific as there was no binding to NGF. In the separate control experiment specific binding of TrkA-Fc (NGF receptor) to the immobilized NGF was detected without binding to immobilized enovin.

From the binding curves obtained using three different concentrations of GFRα, the following constants in Table 3 were derived. These results demonstrate that GFRα3 binds specifically to enovin.

TABLE 3

|  | $K_a$ (1 Ms) | $K_d$ (1/s) | $K_D$ (m) |
| --- | --- | --- | --- |
| GFRα3 | $1.65\ 10^5$ | $5.08\ 10^{-4}$ | $3.1\ 10^{-9}$ |

Since GDNF, NTN and PSP all promote the maintenance and survival of different types of neuronal cells, it is anticipated that enovin has similar biological effects on nerve cells and, possibly, on other cell types too. Therefore, it is envisaged that the enovin protein may be useful in the treatment of neural disorders in general, including Parkinson's disease, Alzheimer's disease, peripheral neuropathy, amyotrophic lateral sclerosis (ALS), Huntington's disease, acute brain injury, nervous system tumors, multiple sclerosis peripheral nerve trauma or injury and exposure to neurotoxins.

Enovin could also be useful in various aspects of neuroprotection. Considering its effect on survival of different neuronal cell populations and on the observed neurite extensions in our model of SHSYSY cells, we propose that this compound could have neuroprotective and neuroregenerative applications.

This is based upon the following observations. Taxol induces neuronal apoptosis in NGF-differentiated PC12 rat pheochromocytoma cells (Nuydens et al, submitted). Therefore, taxol induced cytotoxicity has features of neuronal apoptosis, as monitored by DNA fragmentation, Annexin V labelling and bcl-2 protection. As an extension, therefore, it can be deduced that taxol induces apoptosis in differentiated SH-SY5Y cells. Enovin is now shown to be able to reduce this cell death and therefore may reverse neuronal apoptosis in general.

The compound may therefore be helpful in the following neurodegenerative conditions in which apoptosis has been observed, stroke (Hakim 1998), Parkinson's disease (Marsden et al. 1998), Alzheimer's disease (Nagy et al 1998), Huntington's disease (Wellington et al. 1997), Neurotrauma (Smirnova et al. 1998), Peripheral neuropathies, (Srinivisan et al., 1998).

As an example for the last clinical indication, we have shown that this neurotrophic factor actually protects differentiated SH-SY5Y human neuroblastoma cells against taxol-induced cell toxicity.

Methodology of Viability Measurements

Cell viability was determined by adding 100 µl of a 1 mg/ml 2,3-bis[2-methoxy-4-nitro-5-sulphophenyl]-2H-tetrazolium-5-carboxanilide (XTT, Sigma) solution in DMEM (37° C.) supplemented with 0.02 mM phenazine methosulfate (PMS, Sigma) to each well. The plates were then incubated at 37° C. for 2.5 hours. The optical densities were read (Molecular devices) at 450 nm, using 650 nm as a reference. The XTT assay is based on the conversion of the tetrazolium salt XTT into a red colored formazan product. This reaction is performed by mitochondrial enzymes.

Methodology of Neuronal Differentiation

1. Differentiation in human neuroblastoma SHSY5Y cells

SHSY5Y cells are differentiated for 5 days with 25 nM staurosporine. Effect of Enovin is measured 72 hrs after start of the experiment. (reference Jalava et al. "Protein Kinase inhibitor staurosporine induces a mature neuronal phenotype in SH-SY5Y human neuroblastoma cells through an a,b,z PKC independent pathway" Journ cell Physiol, 155, 301-312 (1993)).

2. Measurement of Neurite Extension.

Morphological changes of neurones were automatically quantified as follows. Briefly, at the appropriate times, glutaraldehyde was added directly to the medium and left for 30 minutes at room temperature. This ensured that the morphology of the cells at that time point reflected the real situation. The cells were observed through transmitted light mode in an Axiovert microscope (Zeiss Oberkochen, Germany), equipped with a Marzhauser scanning stage driven by an Indy workstation (Silicon Graphics, Mountain View, USA). Images were captured using a MX5 video camera (HCS). About 3000 cells were evaluated in 64 aligned images, forming a 8×8 square matrix of images. The exact alignment of the images ensured that neurites could be followed from one image field into the next. Automatic detection of the neurite extensions, labeled by polyclonal tau antibody was performed using an unbiased detector of curvilinear structures (Steger 1998). The analysis software automatically calculated total cell body area, number of cell bodies and total neurite length.

To investigate the effect of enovin on different cell types, two assays were performed, a DNA synthesis assay and a chemotaxis assay.

DNA Synthesis Assay

Cells including human dermal fibroblasts (39SK), human umbilical vein endothelial cells (HUVEC), human smooth muscle cells (HSMC), human chondrocytes, and rat osteoblasts were maintained in DMEM containing 10% FBS (39-SK, HSMC, rat osteoblasts) or defined media (chondrocytes and HUVEC) at 37° C. with 5% $CO_2$ and 95% air. For the DNA synthesis assay, cells were seeded in a 96-well tissue culture plate at a density of 5,000 cells/well in DMEM containing 10% FBS and incubated for 24 h. The culture medium then was replaced with DMEM containing various concentrations of Enovin and 0.1% BSA (for 39-SK, osteoblasts, HSMC, chondrocytes) or DMEM containing various concentrations of Enovin and 0.5% FBS (for HUVEC) and cells were incubated for 24 h. Subsequently, the culture medium was replaced with 100 µl of DMEM containing 5% FBS and 0.1 µl Ci of [$^3$H]-thymidine. Following 2 h of pulse labelling, cells were then fixed with methanol/acetic acid (3:1, vol/vol) for 1 h at room temperature. The fixed cells were washed twice with 80% methanol. The cells were solubilized in 0.05% trypsin (100 μl/well) for 30 min and then in 0.5% SDS (100 μl/well) for an additional 30 min. Aliquotes of cell lysates (180 μl) were combined with 2 ml of scintillation cocktail and the radioactivity of cell lysates was measured using a liquid scintillation counter (Wallac 1409).

Chemotaxis Assay

Cells were maintained as described in "*DNA 25 Synthesis Assay*". The chemotactic activity of Enovin was analyzed using a 12-well modified Boyden Chamber (McQuillan, D. J., Handley, C. J., Campbell, M. A., Bolis, S., Milway, V. E., Herington, A. C., (1986), "Stimulation of Proteoglycan biosynthesis by serum and insulin-like growth factor-I in cultured bovine articular cartilage", Biochem. J. 240:423-430). Cells were trypsinized using 0.05% trypsin and 0.5 mM EDTA and resuspended in DMEM. To the bottom wells of a Boyden chamber, aliquots of 150 μl of media containing various concentrations of Enovin were added. A polycarbonate membrane (8 μm) coated with 0.1 mg/ml of type I collagen was placed on the top of the bottom wells, followed by assembling the top wells. To the top wells, aliquots of 100 μl of cells (70,000 cells/ml) were added. Following a 6-h incubation period, the apparatus was disassembled. Cells remaining on the top of the membrane were removed. The membrane was fixed with 10% formaldehyde for 15 min, followed by staining with Gill's strength hemotoxylin. Cells were counted under microscopy (250× magnification), and the average of cell counts from five areas of each well was used. Each experiment was repeated at least four times. The results were expressed as the fold of control (DMEM containing 0.1% BSA).

As illustrated by the results in FIG. 8 to 18, enovin has no effect on proliferation in each of the cell types used, or on the migration of HUVEC cells (FIG. 14) as described above. There was an effect of enovin on SH-SY-5Y neuroblastoma cells. This demonstrated enovins selective effect on neuronal cells.

Both GDNF and NTN have been shown to signal via a signalling complex composed of a ligand-binding subunit, either GFRα-1. or GFRα-2 and a signalling subunit, the cRET protein tyrosine kinase. Enovin is expected to exert its biological effects via a similar signalling complex composed of a GFRα binding partner (either GFRα-1, GFRα2, the recently characterized orphan receptor GFRα-3 or other as yet uncharacterized members of the GFRα family) in combination with cRET or another signalling partner, Indeed, our binding data show that enovin can bind specifically to GFRα-3.

In humans, germ line mutations in GDNF or cRET can lead to several disease phenotypes including multiple endocrine neoplasia and Familial Hirschsprung disease (HSCR) (Romeo et al., 1994, Edery et al., 1994, Angrist et al., 1996). Both diseases are associated with gut dismotility, with Hirschsprung disease being the most common cause of congenital bowel obstruction in infants. Interestingly, GDNF and CRET knockout mice exhibit remarkably similar pathologies with renal agenesis and intestinal aganglionosis (Sanchez et al, 1996; Moore et al., 1996; Pichel et al., 1996). Enovin could be involved in similar disorders of the gut or the kidneys or, since it is ubiquitously expressed, could be important in the development of other peripheral organs in the body.

The interaction of ligands with their receptors is generally achieved by the interaction of specific bonds from particular residues in both proteins. Fragments of a protein can serve as agonists activating the receptor to elicit its growth promoting and survival sustaining effects on cells. Parts of enovin or synthetic peptides based on the enovin protein sequence can therefore be useful as agonists or antagonists to regulate its receptor GFRα3. Using peptide synthesis or recombinant techniques, hybrid growth factors composed of parts of GDNF, NTN or PSP or any other neurotrophic or growth factor with parts of enovin can be produced to yield a novel synthetic growth factor with new properties.

Two pilot trials were conducted to test whether enovin is able to change the taxol-induced sensory deficits in rats after subplantar injections in rats. In a first experiment, it was tested whether a single treatment with enovin could reverse the taxol-induced sensory deficit, whereas in a second trial it was tested whether enovin could prevent the development of the taxol-induced deficits.

Reversal Over Tine Of Taxol-Induced Sensory Dysfunction.

Procedure

Male Sprague-Dawley rats, weighing 300-340 gram, were used. The animals were housed individually with food and water ad lib. Before the start of the experiment, the animals were placed in standard observation cages and after a habituation period of 15 min, the pin prick reflex was evaluated. To do so, the plantar surface of the right paw of the animal was stimulated with a needle and the reactivity to this pin-prick was scored as either present (score=1) or absent (score=0). Within one session, the procedure was repeated three times with a time interval of 1 min between 2 consecutive stimulus presentations; as such the pin prick test consisted of 3 measures of reactivity to a pin prick. Only rats having normal reactions on the 3 pin pricks were included in the experiment.

On the 3 consecutive days in the morning, the animals received daily a subplantar injection of 50 μl of taxol (3 mg/ml paclitaxel dissolved in cremophor and dehydrated alcohol plus water) in the right hind paw. During the next morning, the pin prick reflex was re-evaluated and animals not showing any reactivity to the 3 stimulus presentations were selected. These animals were randomly divided in subgroups (n=10/group) receiving a subplantar injection in the right hind paw of 75 μl of either vehicle, saline or 23 or 130 μg/ml. enovin. Because no differences were observed between the results of the vehicle and saline treated animals, both groups were joined (control group). At days 1, 4, 5 and 7 after the last treatment, the pin prick test was performed both in the morning (between 8 and 9 a.m.) and the evening (between 3:30 and 4:30 p.m.). On day 8, a last pin prick test was taken during the morning. For each animal, the cumulative score of reactivity to the pin prick was measured over time. Because in total 9 pin prick tests (each consisting of 3 pin prick presentations) were performed after the last drug treatment, the maximal score to be reached over the total time period of the experiment is 27.

Results

Repeated subplantar injections of taxol over 3 consecutive days results in an acute inflammatory reaction with a lack of responding to a pin prick stimulation in the majority of animals. A subplantar injection of saline or vehicle did not affect the taxol-induced deficit. At the first measurement, only 4 out of 20 controls showed at least 1 reaction to the three pin pricks and the mean (±SEM) pin prick score of the controls at the first measurement was 0.25 (±0.12); this in contrast to the starting of the experiment where the mean score was 3.0 (±0.0) because all animals responded to the pin prick. Even after 8 days of measurement, the reactivity in the controls was still impaired with 11 out of 20 rats responding at least once and with a mean pin prick score of 0.75 (±0.18). Within this control group, none of the rats displayed a normal reactivity to all 3 stimuli. The cumulative pin prick score of the controls over time is presented in FIG. 19. Because the animals were tested 9 times over an 8 days period, the maximal. score to be reached with 3 pin pricks at each test is 27. As seen on the graph, a subplantar injection of saline or vehicle was unable to reverse the taxol-induced deficit over the time period tested. The mean total cumulative score of the controls at the end of the experiment was 5.10 (±0.87); being 18.9% of the maximal score to be reached.

Figure 19:
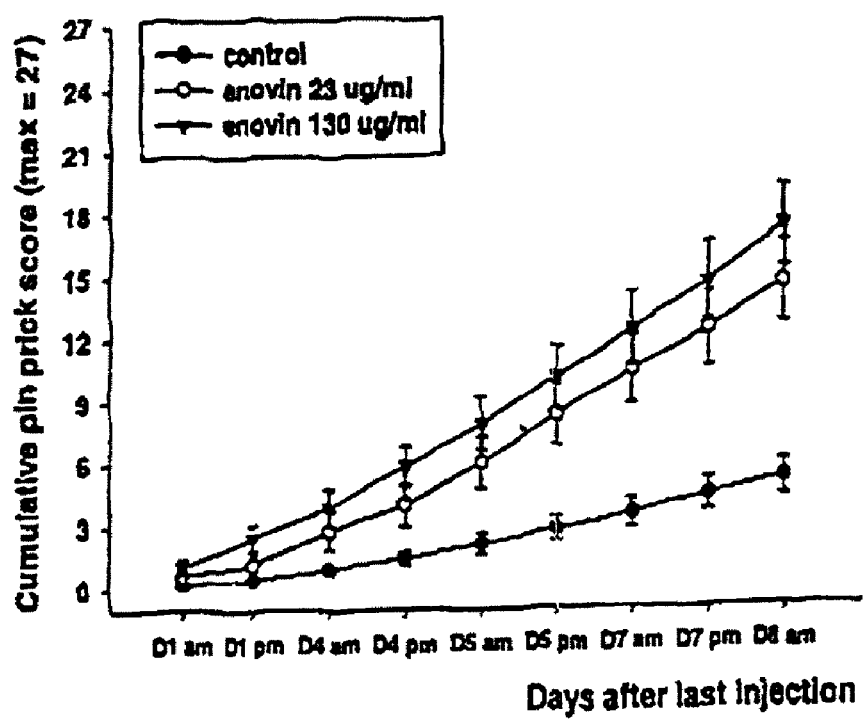

A single subplantar injection of 75 µl of 23 µg/ml enovin, resulted after the first measurement in 4 out of 10 rats responding at least once, with a mean pin prick score of 0.70 (±0.33). At day 8, all 10 animals responded at least once to the pin prick, and a normal reactivity was present in 5 out of 10 rats. The average pin prick score of this group at day 8 was 2.20 (±0.29). As compared to the controls, the average cumulative score at the end of the 8 days of measurement was significantly increased (Mann—Whitney U-test, two-tailed, $p<0.01$), reaching a mean pin prick score of 14.50 (±1.96) (FIG. 19). This is 53.7% of the maximal score.

Also with an subplantar injection of 130 µg/ml enovin there was improved efficacy against the controls. At the first measurement after 130 µg/ml enovin, 6 out of 10 rats responded at least once with a mean pin prick score of 1.10 (±0.35). At day 8, all 10 animals responded to at least one pin prick with a mean score of 2.60 (±0.22). A normal reactivity to the 3 pin pricks was present in 8 out of 10 rats. The average cumulative total pin prick score at the end of the experiment in this group was 17.20 (±1.94). This is 63.7% of the total possible score and significantly improved as compared to the control group ($p<0.01$).

Prevention Over Time of Taxol-Induced Sensory Dysfunction.

Procedure

Male Sprague-Dawley rats, weighing 300-340 gram, were used. The animals were housed individually with food and water ad lib. Before the start of the experiment, the animals were placed in standard observation cages and after a habituation period of 15 min, the pin prick reflex was evaluated. To do so, the plantar surface of the right paw of the animal was stimulated with a needle and the reactivity to this pin-prick was scored as either present (score=1) or absent (score=0). Within one session, the procedure was repeated three times with a time interval of 1 min between 2 consecutive stimulus presentations; as such the pin prick test consisted of 3 measures of reactivity to a pin prick. Only rats having normal reactions on the 3 pin pricks were included in the experiment (pin prick score=3). After this control measurement, the animals were randomly divided in subgroups (n=10/group) receiving an subplantar injection in the right hind paw of 75 µl of either vehicle, saline or 23 or 130 µg/ml enovin. Because no differences were observed between the results of the vehicle and saline treated animals, both groups were joined (control group). During the 3 consecutive days, the animals received daily a subplantar injection of 50 µl of taxol (3 mg/ml paclitaxel dissolved in cremophor and dehydrated alcohol plus water) in the right hind paw. At days 1, 4, 5 and 7 after taxol, the pin prick test was performed both in the morning (between 8 and 9 a.m.) and the evening (between 3:30 and 4:30 p.m.). On day 8, a last pin prick test was done during the morning. For each animal, the cumulative score of reactivity to the pin prick was measured over time. Because in total 9 pin prick tests (each consisting of 3 pin prick presentations) were performed after the taxol treatment, the maximal cumulative score to be reached over the total time period of the experiment is 27.

Results

Figure 20:
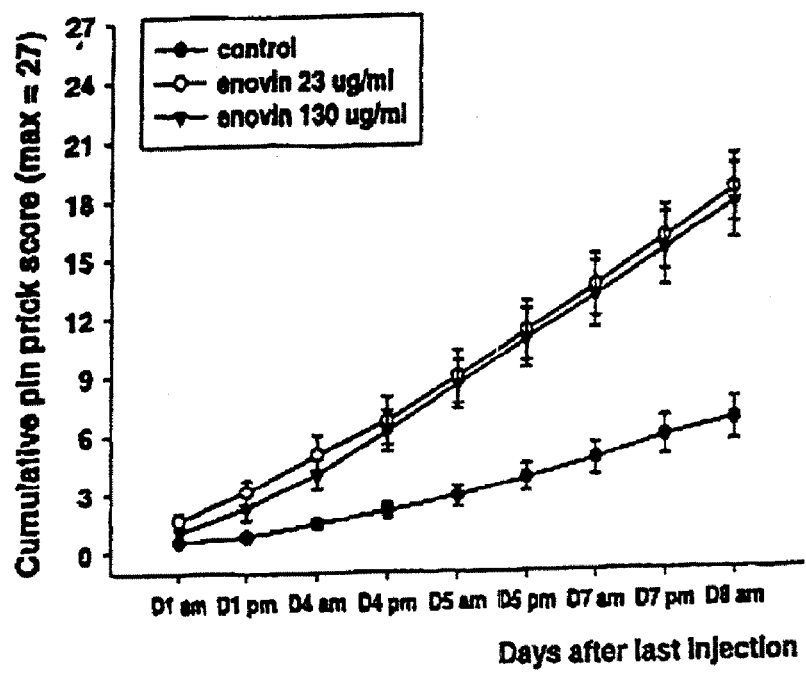

A subplantar injection of saline or vehicle before taxol did not prevent the taxol-induced deficit in the pin prick test. At the first testing after taxol, 8 out of 20 rats responded at least once to the pin prick, with a mean pin prick score of 0.60 (±0.18). At day 8, the taxol-induced deficit was still present, with only 8 out of 20 animals responding and having a mean score of 0.8 (+0.25). Within two animals, a normalized pin prick reflex was present. Over time, the cumulative pin prick score was also reduced, resulting in a mean value of 6.55 (±1.08), which is 24.3% of the maximal score (FIG. 20).

Pretreatment with 23 µg/ml enovin reduced the taxol-induced deficits on the pin prick. At day 1, 8 out of 10 animals responded at least once, and the average pin prick score was 1.70(±0.40). At day 8, 5 all animals were responding with a mean score of 2.50 (±0.27). Here 7 animals revealed a normal reactivity on all pin prick exposures. With regard to the cumulative responding over time (FIG. 20), the mean total score was significantly improved ($p<0.01$) over the control level to 18.40 (+1.73); this is 68.1% of the maximal value.

Comparable results were obtained after a pretreatment with 130 µg/ml enovin. Here, 6 out of 10 animals responded during the first testing with a mean pin prick score of 1.70 (+0.31). At day 8, all animals were reacting at least once to a pin prick stimulation with a mean score of 2.40 (+0.22) and all 3 reactions were normal in half of the animals. With regard to the cumulative score, the mean score obtained at day 8 is 17.70 (+1.92), representing 65.5% of the total score.

The present series of experiments indicate that a single subplantar injection of enovin is able to reduce the taxol-induced sensory deficits as measured by a pin prick test. Activity is seen when the drug was applied both before and after taxol.

Enovin is a possible candidate for pain syndromes with mainly a peripheral and central neurogenic component, rheumatic/inflammatory diseases as well as conductance disturbances, and. can play a modulatory role in sensory processes after transdermal, topical, local, central (such as epidural, intrathecal, and the like) and systemic application.

Further it is worthwhile to use enovin as a diagnostic tool to screen for physiophatological changes in the area's mentioned above.

Comparison Of Enovin mRNA Expression in Normal Versus Diseased Tissues

The expression of Enovin mRNA was quantitatively analysed using the ABI Prism 7700 Sequence Detection System (TaqMan; Perkin Elmer) using proprietary technology developed and carried out at Pharmagene Laboratories Ltd, Royston, United Kingdom. The system uses a fluorogenic probe to generate sequence specific fluorescent signals during PCR. The probe is an oligonucleotide with fluorescent reporter and quencher dyes attached, it is positioned between the forward and reverse PCR primers. While intact, the intensity of reporter fluorescence is suppressed by the quencher. Should the probe form part of a replication complex, the fluorescent reporter is cleaved from the quencher by a 5' to 3' exonuclease activity inherent in Taq polymerase. The increase in fluorescent reporter signal within a reaction is a direct measure of the accumulation of PCR product. The starting copy number of an mRNA target sequence (Cn) is established by determining the fractional PCR cycle number (Ct) at which a PCR product is first detected—the point at which the fluorescence signal passes above a threshold baseline. Quantification of the amount of target mRNA in each sample is established through comparison of experimental Ct values with a standard curve.

RNA Preparation And Quality Control

Total RNA was isolated from whole and sub-dissected tissue, using Tri-Zol reagent (Life Technologies, Gaithersburg, Md., USA) according to the suppliers' protocol. Quality control procedures for all RNA samples included an assessment of integrity (intact 18S and 28S ribosomal RNA) and determination of the presence of high abundance (actin) and low abundance (transferrin receptor) transcripts.

Primer/Probe Design

A pair of primers and a TaqMan probe were designed to amplify a specific sequence from Enovin

```
Primer 1:
5' ACGGTTCTCCAGGTGCTGT 3'          (SEQ ID NO: 44)

Primer 3:
5' TGCTGCCGACCCACG 3'              (SEQ ID NO: 45)

Probe 5:
5' CTACGAAGCGGTCTCCTTCATGGACG 3'   (SEQ ID NO: 46)
```

In addition a pair of primers and a TaqMan probe were designed which span an intron and amplify a portion of the human GAPDH gene

```
Primer 2:
5' CAGAGTTAMAGCAGCCCTGGT 3'        (SEQ ID NO: 47)

Primer 4:
5' GAAGGTGAAGGTCGGAGTCAAC 3'       (SEQ ID NO: 48)

Probe 6:
5' TTTGGTCCGTATTGGGCGCCT 3'        (SEQ ID NO: 49)
```

Probe 5 is labelled with the fluor FAM while probe 6 is labelled with the fluor VIC.

DNase Treatment of Total RNA

For each tissue tested 2.2 µg of total RNA was digested with 2 units of RNase free DNase (Gibco BRL) for 15 minutes at room temperature in a 20 µl volume of 1× DNase buffer (Gibco BRL). The reaction was stopped by addition of 2 µl of 25 mM EDTA solution. The samples were then incubated at 65° C. for 10 minutes to inactivate the enzyme.

First Strand cDNA Synthesis

For each tissue tested 100 ng of total RNA was used as template for first strand cDNA synthesis. The RNA in a volume of 4 ml and in the presence of 50 nM primers 1 and 2, 1×PCR buffer II (Perkin Elmer) and 5 mM $MgCl_2$ was heated to 72° C. for 5 minutes and cooled slowly to 55° C. After addition of all other reagents, the 6 ml reaction was incubated at 48° C. for 30 minutes followed by an enzyme inactivation step of 90° C. for 5 minutes. The final reaction conditions were as follows: 1×PCR buffer II, 5 mM $MgCl_2$, 1 mM dATP, dTTP, dGTP, dCTP, 12.5 units MuLV reverse transcriptase (Gibco BRL).

PCR Amplification of First Strand cDNA Products

The cDNA derived from 100 ng total RNA for each sample was subjected to PCR amplification in a single reaction to identify both target and GAPDH transcripts. The final primer/probe concentrations for target were 300 nM primer 1, 300 nM primer 3 and 200 nM probe 5, those for GAPDH were 20 nM primer 2, 20 nM primer 4 and 100 nM probe 6. The final concentration of other reagents in the reaction were 4.5% glycerol, 1× TaqMan buffer A (Perkin Elmer), 6.25 mM $MgCl_2$ 430M dATP, dUTP, dGTP, dCTp, 2.5 units AmpliTaq Gold. The PCR amplification was carried out in the ABI 7700 sequence detection system, an initial enzyme activation step of 94° C. for 12 min was followed by 45 cycles of 94° C. 15 secs, 60° C. 1 min (minimum ramp time).

Diseases and Tissues Tested

Figure 25:
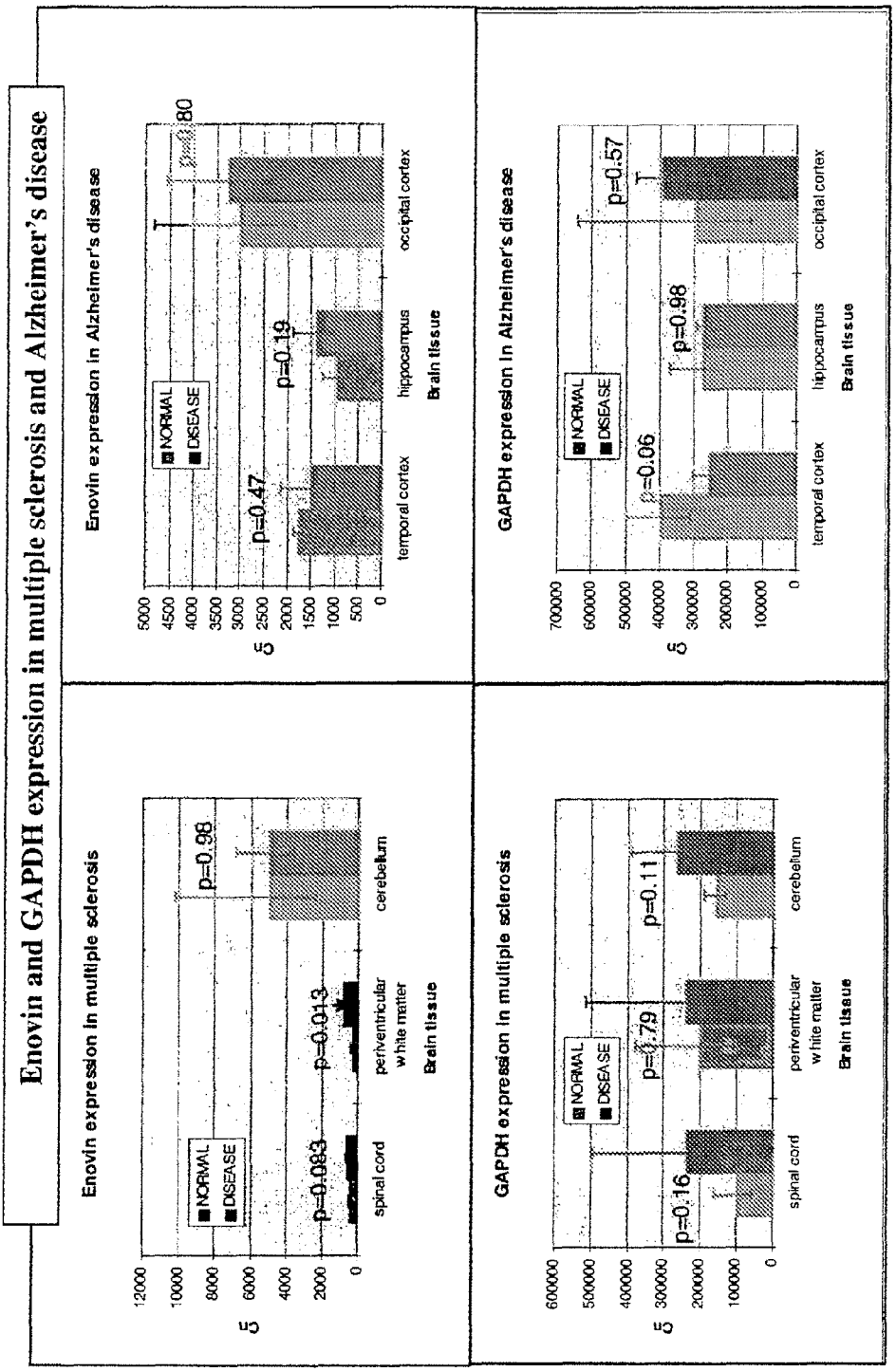
FIG. 25 is a graphic representation of the results obtained from experiments designed to compare the levels of expression of enovin in normal diseased tissue. Enovin and GAPDH expression is represented in brain tissue, in respect of multiple sclerosis and Alzheimer's disease.
Figure 26:
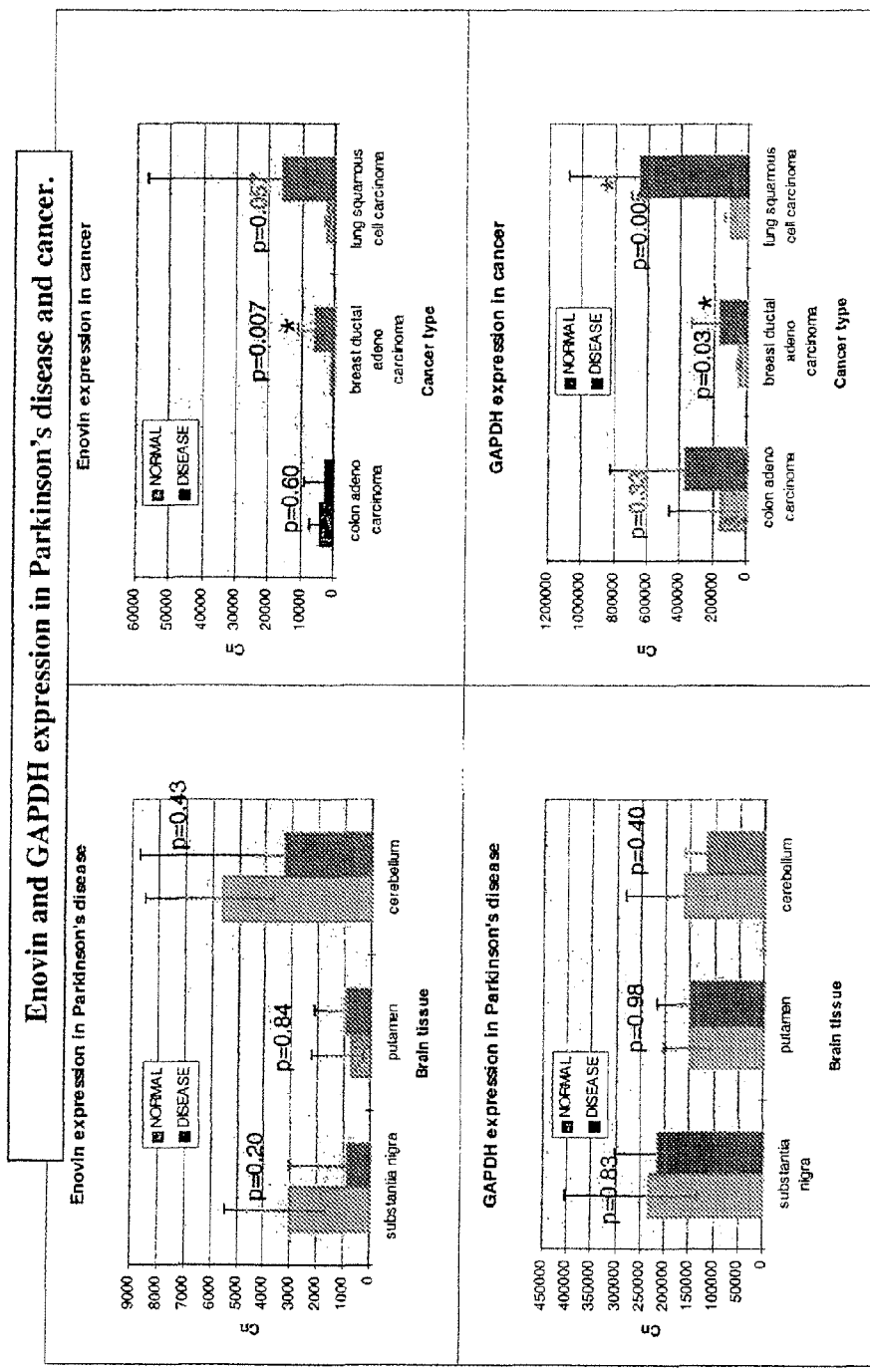
FIG. 26 is a graphic representation of the results obtained to detect levels of expression of enovin and GAPDH in Parkinson's disease and cancer.

Enovin mRNA expression was compared in tissues derived from disease patients and normal control individuals (FIGS. 25 and 26). The table below shows the diseases and corresponding tissues that have been investigated. For each condition, three diseased and three control samples were analysed.

| Patholog | Tissue 1 | Tissue 2 | Tissue 3 |
|---|---|---|---|
| Alzheimer's disease | Temporal Cortex | Hippocampus | Occipital Cortex |
| Multiple Sclerosis | Spinal Cord | Periventicular White Matter | Cerebellum |
| Parkinson's Disease | Substantia Nigra | Putamen | Cerebellum |
| Cancer | Colon Adenocarcinoma | Breast Ductal Adenocarcinoma | Lung Squamous Cell Carcinoma |

Statistical Analysis

For each group of 3 tissues, the mean and standard deviation were calculated on the Ct values (which are normally distributed) and were then converted into Cn values according to the formula $Cn=10^{[(Ct-40.007)/-3.623]}$. Analysis of variance (ANOVA) was performed on the Ct values also to compare the mean Enovin mRNA expression levels in normal versus diseased tissues.

FIGS. 25 and 26 show the mean Enovin mRNA copy numbers (±SD; n=3) in diseased versus control tissues. Statistical analysis showed a significant increase in the Enovin expression level in the periventricular white matter of patients with multiple sclerosis (p=0.013). The internal GAPD control showed no significant difference (p=0.79). Although the Enovin expression level in the periventricular white matter is quite low in normal tissue (270 copies per 100 ng total RNA on average versus 200,000 copies of GAPDH), the level is three times higher (825) in patients with multiple sclerosis.

Only one other diseased tissue showed a significant difference versus normal control; in breast ductal adenocarcinoma, the Enovin mRNA expression level is 6 times higher (6,000 versus 1,000; p 0.007), but the GAPDH control value is also significantly increased (165,000 versus 4,4000; p=0.03), probably representing a general increase in mRNA levels.

In conclusion, we have found Enovin mRNA levels to be upregulated in the periventricular white matter of patients with multiple sclerosis.

Use of phospho-specific antibody cell-based ELISA for screening of enovin mimetic on GFRc3/cP2.T receptor complex.

Method can also be used for identification of agonist or antagonist of other neurotrophin receptors, such as GFRα1, GFRα2, GFRα4, TrkA, TrkB and TrkC.

Assay

Using this assay we can identify agonist or antagonist compounds of neurotrophic growth factors by measuring the activation of key signalling kinases activated in the neurotrophic pathway or by measuring the activation of cRET receptor kinase. The activation is measured by detecting the amount of phosphorylated kinase or receptor kinase using phospho-specific antibodies. We will use NIH 3T3 cells expressing transiently or permanently TrkA, TrkB, TrkC, GFRa1/cRET, GFRa2/cRET, GFRa3/cRET or GFRa4/cRET.

The activation of p42/p44 MAP kinase, PKB kinase, c-jun, CREB, JNK/SAPK kinase and other kinases is detected using commercially available phospho-specific antibodies. In addition, cRET activation can be deleted. using phospho-specific cRET antibody.

The protocol used was as follows:

Plate NIH 3T3 cells in 96-wells in 10% calf serum, cells have to be 80% confluent before stimulation.

Next day, replace medium with serum-free medium and starve cells for 18-24 h.

After starvation stimulate cells with compounds and neurotrophic factors as positive control (10 ng/ml for neurotrophic factors)

Fix cells with 4% formaldehyde in PBS at 4° C. for 20 min.

Wash cells 3× with 200 μl PB S/0.1% Triton for 5 min.

Quench the cells with 100 μl p 0.6% $H_2O_2$ in PBS/0.1% Triton for 20 min.

Wash cells 3× with 200 μl PBS/0.1% Triton for 5 min.

Block the cells with 100 μl. 10% foetal. calf serum in PBS/0.1% Triton for 60 min.

Incubate the cells with phosphospecific antibody in 50 μl 5% BSA//PBS/0.1% Triton, over night at 4° C. Antibody dilution should be experimentally determined, suggested range 1:100-1:250.

Wash cells 3× with 200 μl PBS/0.1% Triton for 5 min.

Incubate with secondary antibody HRP linked, dilution 1:100 in 50 μl 5% BSA/PBS/0.1% Triton, for 1 h at room temperature.

Wash cells 3× with 200 μl PBS/0.1% Triton for 5 min.

Dissolve 1 tablet of OPD (Sigma) in 25 ml buffer (3.65 g citric acid-$H_2O$ and 5.9 g $Na_2HPO_4$-$2H_2O$ in 0.5l$H_2O$ pH 5.6) and add 12.5 μl $H_2O_2$ Add 50 μl to each well and incubate for 15 min on shaker (200 rpm), covered with aluminium foil.

Stop the reaction with 25 μl $H_2SO_4$.

Measure $OD_{490-650}$ on the ELISA reader.

Mesencephalic Dopaminergic Neuronal Culture

Neuronal. Culture

Neuronal cultures were prepared from the ventral mesencephalon of foetal rat by enzymatic and mechanical dispersion. The tissue was collected, washed in ice-cold $Ca^{2+}$- and $Mg^{2+}$-free phosphate buffered saline containing 0.6% glucose (PBSG) and incubated for 30 min with PBSG containing 0.1% trypsin at 37° C. The cell suspension was plated at a density of 2.5 $10^5$ cells/$cm^2$ onto 96 well NUNC tissue culture plates. In advance, culture plates were coated with poly-L-ornithine and CDM containing 10% foetal calf serum. The cultures were maintained in chemically defined medium (CDM), composed of a 1:1 mixture of Dulbecco's Modified Eagles medium and F12 Nutrient supplemented with glucose (0.6%), glutamine (2 mM), sodium bicarbonate (3 mM), HEPES (5 mM), insulin (25 μg/ml), human transferrin (100 μg/ml), putrescine (60 μg/mil), sodium selenite (30 nM), streptomycin (100 μg/ml) and penicillin (100 IU/ml).

Treatment with Neurotrophic Factors

Neurotrophins were dissolved in 0.5% bovine serum albumin as a stock. Neurotrophins were added 3 h after initial plating and after 5 days in culture. The same amount of 0.5% bovine serum albumin was added to the control wells.

High-Affinity Dopamine Uptake

Dopamine uptake was measured after 10 days. For the uptake, cells were washed twice with pre-warmed PBS supplemented with glucose (5 mM), ascorbic acid (100 mM) and pargyline (100 mM) and pre-incubated for 10 min with the same solution. The pre-incubation solution was replaced with the same solution containing 50 nM [$^3H$]DA and incubation continued for 15 min at 37° C. Uptake was stopped by 3 rapid washes with ice-cold PBS. The accumulated [$^3H$] dopamine was released by incubating with acidified ethanol for 30 min at room temperature. Radioactivity was determined after addition of 4 ml of scintillation liquid (Packard ultima gold MV) using Packard scintillation counter. Non-specific uptake was determined by adding 20 μM cocaine.

TABLE 4

Effect of enovin on [$^3H$] dopamine uptake

| Treatment | Percent control [$^3H$] dopamine uptake | n |
|---|---|---|
| control | 100 | 5 |
| enovin 300 ng/ml | 111 | 4 |
| enovin 1000 ng/ml | 127 | 5 |
| enovin 2000 ng/ml | 152 | 5 |
| enovin 4000 ng/ml | 161 | 1 |
| enovin 10000 ng/ml | 165 | 2 |

Cells were grown for 10 days in the presence or absence of enovin. Untreated controls were set as 100%. Results are obtained in 1-5 independent experiments.

References

Altschul, S. F., Gish, W, Miller, W., Myers, E. W. & Lipruan, D. J. (1990) Basic local alignment search tool, *J. Mol. Biol.* 215, 403-410.

Angrist, M., Bolk, S., Halushk H., Lapchak, P. A. & Chakravarti, A. (1996) Germline mutations in glial cell line-derived neurotrophic factor (GDNF) and RET in a Hirschsprung disease patient. *Nature Genetics* 14, 341-344.

Baloh, R. H Tansey, M. G., Golden, J. P., Creedon, D. J., Heuckeroth, R. O., Reck, C. L., Zimonjic, D. B., N. C. Popescu, N. C., Johnson, E. M. & Milbrandt, J. (1997) TrnR2, a novel receptor that mediates neurturin and GDNF signaling through Ret. *Neuron* 18, 793-802.

Baloh, R. H., Gorodinsky, A., Golden, J. P., Tansey, M. G., Keck, C. L., Popescu, N. C., Johnson, E. M. & Milbrandt, J. (1998) GFRα3 is an orphan member of the GDNF/neurturin/persephin receptor family. *Proc. Natl. Acad. Sci. USA* 95, 5801-5806.

Barr, P. J. (1991) Mammalian subtilisins: the long-sought dibasic processing endoproteases. *Cell.* 66,1-3.

Beck, K. Valverde, J., Alexi, T., Poulsen, K., Moffat, B., Vandlen, R A., Rosenthal, A. & Hefti, F. (1995) Mesencephalic dopaminergic neurons protected by GDNF from axotomy-induced degeneration in the adult brain. *Nature* 373, 339-341.

Bilang-Bleuel, A., Revah, F., Colin, P., Locquet, I. Robert J. J., Mallet, J. & Horellou, P. (1997) Intrastriatal injection of an adenoviral vector expressing ghial-cell-line-derived neurotrophic factor prevents dopamiriergic neuron degeneration and behavioral impairment in a rat model of Parkinson disease. *Proc. Natl. Acad. Sci. USA* 94, 8818-8823.

Buj-Bello, A., Buchman, V. L., Horton, A., Rosenthal, A. & Davies A. M. (1995) GDNF is an age-specific survival factor for sensory and autonomic neurons. *Neuron* 15, 821-828.

Buj-Bello, A., Adu, J., Piñon, L. G. P., Horton, A., Thompson, J., Rosenthal, A., Chinchetru, M., Buchman, V. L. & Davies, A. M. (1997) Neurturin responsiveness requires a GPI-linked receptor and the Ret receptor tyrosine kinase. Nature 387, 721-724.

Choi-Lundberg, D. L., Lin, Q., Chang, Y. N., Chiang, Y. L., Hay, C. M., Mohajeri, H., Davidson, B. L. & Bohn, M. C. (1997) Dopaminergic neurons protected from degeneration by GDNF gene therapy. *Science.* 275, 838-841.

Creedon, D. J., Tansey, M. G., Baloh, R H, Osborne, P. A., Lampe, P. A., Fahrner, T. J., Heuckeroth, R. O., Milbrandt, J. & Johnson, E. M. (1997) Neurturin shares receptors and signal transduction pathways with glial cell line-derived neurotrophic factor in sympathetic neurons. Proc. Natl. Acad. Sci. USA 94, 7018-7023.

Durbec, P., Marcos-Gutierrez, C. V., Kilkenny, C., Grigoriou, H., Wartiowaara, K Suvanto, P., Smith, D., Ponder, B., Costantini, F., Saarma, M., Sariola, H. & Pachnis, v. (1996) GDNF signalling through the RET receptor tyrosine kinase. *Nature* 381, 789-793.

Edery, P., Lyonnet, S Mulligan, L. M., Pelet, A., Dow, E., Abel L., Holder S., Nihoul-Fekete, C., Ponder, B. A. & Murinich, A. (1994) Mutations of the RET proto-oncogene in Hirschsprung's disease. *Nature* 367, 378-380.

Gash, D. M., Zhang, Z., Ovadia, A., Cass, W. A., Yi, A., Simmerman, L., Russell, D., Martin, D., Lapchak, P. A., Collins, F., Hoffer, B. J. & Gerhardt, G. A. (1996) Functional recovery in parkinsonian monkeys treated with GDNF. *Nature* 380, 252-255.

GFRα Nomenclature Committee (1997) Nomenclature of GPI-linked receptors for the GDNF ligand family. *Neuron* 19, 485. 25

Hakim A "Ischemic penumbra: the therapeutic window." Neurology. 1998 September; 51 (3 Suppl 3):S44-6.

Henderson, C. E., Phillips, H. S., Pollock, R. A., Davies, A. M., Lemeulle, C., Armanini, M., Simmons, L., Moffet, B., Vandlen, R. A., Koliatsos, V. E. & Rosenthal, A. (1994) GDNF: a potent survival factor for motoneurons present in peripheral nerve and muscle. *Science* 266, 1062-1064.

Heng, H. H. Q., Squire, J. & Tsui, L.-C. (1992) High resolution mapping of mammalian genes by in situ hybridization to free chromatin. Proc. Natl. Acad. Sci. USA 89, 9509-9513.

Heng, R. H. Q. & Tsui, L.-C. (1993) Modes of DAPI banding and simultaneous in situ hybridization. Chromosoma 102, 325-332.

Heuckeroth, R. O., Kotzbauer, P., Copeland, N. G., Gilbert, D. J., Jenkins, N. A., Zimonjic, D. B., Popescu, N. C., Johnson, E. M. & Milbrandt, J. (1997) Neurturin, a novel neurotrophic factor, is localized to mouse chromosome 17 and human chromosome 19 p13.3. *Genomics* 44, 137-140.

Jing, S., Wen, D., Yu, Y., Holst, P. L., Luo, Y., Fang, M., Tamir, R., Antonio, L., Hu, Z., Cupples, R., Louis, J.-C., Hu, S., Altrock, B. W. & Fox, G. M. (1996) GDNF-induced activation of the ret protein tyrosine kinase is mediated by GDNFRα, a novel receptor for GDNF. *Cell* 85, 1113-1124.

Jing, S., Yu, Y., Fang, M., Hu, Z., Holst, P. L., Boone, T., Delaney, J., Schultz, H., Zhou, R. & Fox, G. M. (1997) GFRα and GFRα-3 are two new receptors for ligands of the GDNF family. *J. Biol. Chem.* 272, 33111-33117.

Kingsley, D. M. (1994) The TGF-beta superfamily: new members, new receptors, and new genetic tests of function in different organisms. *Genes & Development* 8, 133-146.

Klein, R. D., Sherman, D., Ho, W.-H., Stone, D., Bennett, G. L., Moffat, B., Vandlen, R., Simmons, L., Gu, Q., Hongo, J.-A Devaux, B., Poulsen, K., Armanini, M., Nozaki, C., Asai, N., Goddard, A., Phillips, H., Henderson, C. E., Takahashi, M. & Rosenthal, A. (1997) A GPI-linked protein that interacts with Ret to form a candidate neurturin receptor. *Nature* 387, 717-721.

Kotzbauer, P. T., Lampe, P. A., Heuckeroth, R. O., Golden, J. P Creedon, D. J., Johnson, E. M. & Milbrandt, J. (1996) Neurturin, a relative of glial-cell-line-derived neurotrophic factor. *Nature* 384, 467-470.

Lin, L.-F. H., Doherty, D. H., Lile, J. D., Bektesh, S. & Collins, F. (1993) GDNF: a glial cell line-derived neurotrophic factor for midbrain dopaininergic neurons-.*Science* 260, 1130-1132.

Mandel, R. J., Spratt, S. K., Snyder, R. O. & Leff, S. E. (1997) Midbrain injection of recombinant adeno associated virus encoding rat glial cell line-derived neurotrophic factor protects nigral neurons in a progressive 6-hydroxydopamine-induced degeneration model of Parkinson's disease in rats. *Proc. Natl. Acad. Sd. USA* 94,140S3-14088.

Marsden et al "The causes of Parkinson's disease are being unraveled and rational neuroprotective therapy is close to reality." Ann Neurol. 1998 September; 44(3 Suppl 1):S189-96

Masure, S., Cik, M., Pangalos, M. N Bonaventure, P Verhasselt, P., Lesage, A. S., Leysen, J. E. & Gordon R. D. (1998) Molecular cloning, expression and tissue distribution of glial-cell-line-derived neurotrophic factor family receptor α-3 (GFRα-3). Eur. J. Blochem. 251, 622-630.

Matsushita, N., Fujita, Y., Tanaka, M., Nagatsu, T. & Kiuchi, K. (1997) Cloning and structural organization of the gene encoding the mouse glial cell line-derived neurotrophic factor, GDNF. Gene 203, 149-157.

Milbrandt, J., de Sauvage, F. J., Fahrner, T. J., Baloh, R. H., Leitner, M. L., Tansey, M. G., Lampe, P. A., Heuckeroth, R. O., Kotzbauer, P. T., Simburger, K. S., Golden, J. P Davies, J. A., Vejsada, R., Kate, A. C., Hynes, M., Sherman, D., Nishimura, M., Wang, L. C., Vandlen, R. Moffat, B., Klein, R. D., Poulsen, K., Gray, C., Garces, A., Henderson, C. E., Phillips, H. S. & Johnson, E. M. Jr. (1998) Persephin, a novel neurotrophic factor related to GDNF and neurturin. *Neuron* 20, 245-253.

Moore, M. W., Klein, R. D., Farinas, I., Sauer, H., Armanini, M., Phillips, H., Reichardt, L. F., Ryan, A. M., Carver-Moore, K. & Rosenthal, A. (1996) Renal and neuronal abnormalities in mice lacking GDNF. Nature 382, 76-79.

Mount, H. T., Dean, D. O., Alberch, J., Dreyfus, C. F. & Black, I. B. (1995) Glial cell line-derived neurotrophic factor promotes the survival and morphologic differentiation of Purkinje cells. *Proc. Natl. Acad. Sci. USA* 92, 9092-9096.

Nagy Z et al "The cell division cycle and the pathophysiology of Alzheimer's disease." Neuroscience. 1998 December; 87 (4):731-9.

Naveilhan, F., Baudet, C., Mikaels, A., Shen, L., Westphal, H. & Ernfors, P. (1998) Expression and regulation of GFRα3, a glial cell line-derived neurotrophic factor family receptor. *Proc. Natl. Acad. Sci. USA* 95, 1295-1300.

Nuydens R, Dispersyn G, Van den Kieboorn C, De Jong M, 20 Connors R, Ramaekers F, Borgers M, Geerts H "Bcl-2 protects neuronal cells against taxol-induced apoptosis by inducing mutli-nucleation", submitted Oppenheim, R. W., Houenou, L. J., Johnson, J. E., Lin, L. F., Li, L., Lo, A. C., Newsome, A. L., Prevette, D. M. & Wang, S. (1995) Developing motor neurons rescued from programmed and axotoiny-induced cell death by GDNF. *Nature* 373, 344-346.

Pichel, J. G., Shen, L., Sheng, H. Z., Granholm, A. C., Drago, J., Grinberg, A., Lee, E. J., Huan S. P., Saarma, N., Hoffer, B. J., Sariola, H. & Westphal, H (1996) Defects in enteric innervation and kidney development in mice lacking GDNF. *Nature* 382, 73-76.

Romeo, G., Ronchetto, P., Luo, Y., Barone, V., Seri, M., Ceccherini, I., Pasini, B., Bocciardi, R., Lerone, M., Kaarianen, H. et al. (1994) Point mutations affecting the tyrosine kinase domain of the RET proto-oncogene in Hirschsprung's disease. *Nature* 367, 377378.

Sanchez, M. P., Silos-Santiago, I., Frisen, J., He, B., Lira, S & Barbacid, M. (1996) Renal agenesis and the absence of enteric neurons in mice lacking GDNF. *Nature* 0.382, 70-73.

Sanicola, M., Hession, C., Worley, D., Carmillo, P., Ehrenfels, C., Walus, L., Robinson, S., Jaworski, G., Wei, H., Tizard, R., Whitty, A., Pepinsky, R. B. & Cate, R. L. (1997) Glial cell line-derived neurotrophic factor-dependent RET activation can be mediated by two different cell-surface accessory proteins. Proc. Natl. Acad. Sci. USA 94, 6238-6243.

Smirnova et al "Thrombin is an extracellular signal that activates intracellular death protease pathways inducing apoptosis in model motor neurons". J. Neurobiol. 1998 July; 36(1):64-80.

Srinivisan et al "Serum from patients with type 2 diabetes with neuropathy induces complement-independent, calcium-dependent apoptosis in cultured neuronal cells." J Clin Invest. 1998 Oct. 1; 102(7):1454-62

Steger C "An unbiased detector of curvilinear structures" *IEEE Transactions on pattern analysis and machine intelligence,* 20, 2, 113-125 (1998)

Suvanto, P Wartiovaara, K., Lindahl, H., Aruimäe, U., Moshnyakov, H., Horelli-Kuitunen, N., Airaksinen, M. S., Palotie, A., Sariola, H. & Saarma, M. (1997) Cloning, mRNA distribution and chromosomal .localisation of the gene for glial cell line-derived neurotrophic factor receptor B, a homologue to GDNFRα. *Human Mol. Genet.* 6, 1267-1273.

Tomac, A., Lindqvist, E., Lin, L. F., Ogren, S. O., Young, D., Hoffer, B. J. & Olson, L. (1995) Protection and repair of the nigrostriatal dopaminergic system by GDNF in vivo. *Nature* 373, 335-339.

Treanor, J. J. S., Goodman, L., de Sauvage, F., Stone, D. H., Poulsen, K. T., Beck, C. D., Gray, C., Armanini, M. P., Pollock, R. A., Hefti, F., Phillips, H. S., Goddard, A., Moore, M. W., Buj-Bello, A., Davies, A. M., Asai, N., Takahashi, H., Vandlen, R., Henderson, C. E. & Rosenthal, A. (1996) Characterization of a multicomponent receptor for GDNF. *Nature* 382, 80-83.

Trupp, H., Arenas, E., Fainzilber, M., Nilsson, A. S., Sieber, B. A., Grigoriou, M., Kilkenny, C., SalazarGrueso, E., Pachnis, V., Arumäe, U., Sariola, H., Saarma, M. & Ibanez, C. F. (1996) Functional receptor for GDNF encoded by the c-ret proto-oncogene. *Nature* 381, 785-788.

Wellington et al "Toward understanding the molecular pathology of Huntington's disease." Brain Pathol. 1997 July; 7(3):979-1002.

Widenfalk, J., Nosrat, C Tomac, A., Westphal, H., Hoffer, B. & Olson, L. (1997) Neurturin and glial cell line-derived neurotrophic factor receptorB (GDNFR-α), novel proteins related to GDNF and GDNFR-α with specific cellular patterns of expression suggesting roles in the developing and adult nervous system and in peripheral organs. *J. Neurosci.* 17, 8506-8519.

Widenfalk, J., Tomac, A., Lindqvist, B., Hoffer, B. & Olson, L. (1998) GFRα-3 a protein related to GFRα-1, is expressed in developing peripheral neurons and ensheathing cells. *Eur. J. Neurosci.* 10, 1508-1517.

Worby, C. A., Vega, Q. C., Zhao, Y., Chao, H. H.-J., Seasholtz, A. F. & Dixon, J. E. (1996) Glial cell line derived neurotrophic factor signals through the RET receptor and activates nitogen-activated protein kinase. *J. Biol. Chem.* 271, 23619-23622.

Worby, C. A., Vega, Q. C., Chao, H. H. J., Seasholtz, A. F., Thompson, R. C. & Dixon J. E. (1998) Identification and characterization of GFRα-3, a novel co-receptor belonging to the glial cell line-derived neurotrophic receptor family. *J. Blol. chem.* 273, 3502-3508.

Ian, Q., Matheson, C. & Lopez, O. T. (1995) In vivo neurotrophic effects of GDNF on neonatal and adult facial motor neurons. *Nature* 373, 341-344.

List of Abbreviations
BLAST basic local alignment search tool
bp base pairs
5cDNA complementary DNA
CNS central nervous system
EST expressed sequence taq
EVN enovin
GDNF glial cell-line derivedneurotrophic factor
GFRα GDNF family receptor α
GPI glycosyl phosphatidyl inositol
MTC multiple tissue cDNA
NTN neurturin
PCR polymerase chain reaction
PNS peripheral nervous system
PSP persephin
RT-PCR reverse transcription PCR
TGFB transforming growth factor
FISH fluorescent in situ hybridisation
MTN multiple tissue northern
NGF nerve growth factor
SPR surface plasinon resonance

The invention claimed is:

1. An isolated neurotrophic growth factor polypeptide with neurotrophic activity comprising:
   (a) seven conserved cysteine residues at positions 16, 43, 47, 80, 81, 109, and 111 when the seven cysteine residues are aligned with the seven cysteines within SEQ. ID. NO.3;
   (b) amino acid residues as follows: C at position 16, L at position 18, V at position 25, L at position 28, G at position 29, L at position 30, G at position 31, E at position 36, F at position 40, R at position 41, F at position 42, C at position 43, G at position 45, C at position 47, C at position 80, C at position 81, R at position 82, P at position 83, F at position 91, D at position 93, S at position 105, A at position 106, C at position 109 and C at position 111, each when numbered in alignment with SEQ. ID. NO.3;
   (c) an LGLG repeat, an FRFC motif, a QPCCRP motif, and a SATACGC motif; and
   (d) wherein the isolated neurotrophic growth factor polypeptide comprises at least 90% amino acid homology to residues 1-113 of SEQ. ID. NO. 3, and wherein the isolated neurotrophic growth factor polypeptide has neurotrophic activity.

2. The neurotrophic growth factor polypeptide of claim 1, wherein the neurotrophic growth factor polypeptide has a C-terminal amino acid sequence as set forth in residues 80-113 of SEQ. ID. NO.3.

3. The neurotrophic growth factor polypeptide of claim 1, wherein the neurotrophic growth factor polypeptide has a C-terminal amino acid sequence as set forth in residues 49-113 of SEQ. ID. NO.3.

4. A composition comprising the neurotrophic growth factor polypeptide of claim 1 and a pharmaceutically acceptable carrier.

5. The neurotrophic growth factor polypeptide of claim 1 comprising at least 95% amino acid homology to SEQ ID NO. 3.

* * * * *